US011173269B2

(12) United States Patent
Sims et al.

(10) Patent No.: US 11,173,269 B2
(45) Date of Patent: Nov. 16, 2021

(54) ADAPTOR FOR RESPIRATORY ASSISTANCE SYSTEMS

(71) Applicant: FISHER & PAYKEL HEALTHCARE LIMITED, Auckland (NZ)

(72) Inventors: David John Sims, Auckland (NZ); David Robert Kemps, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 343 days.

(21) Appl. No.: 16/323,724

(22) PCT Filed: Aug. 15, 2017

(86) PCT No.: PCT/NZ2017/050109
§ 371 (c)(1),
(2) Date: Feb. 6, 2019

(87) PCT Pub. No.: WO2018/034574
PCT Pub. Date: Feb. 22, 2018

(65) Prior Publication Data
US 2019/0167937 A1    Jun. 6, 2019

Related U.S. Application Data

(60) Provisional application No. 62/375,405, filed on Aug. 15, 2016, provisional application No. 62/427,796, filed on Nov. 29, 2016.

(51) Int. Cl.
*A61M 16/06*       (2006.01)
*A61M 16/08*       (2006.01)
(Continued)

(52) U.S. Cl.
CPC .... *A61M 16/0672* (2014.02); *A61M 16/0683* (2013.01); *A61M 16/0688* (2014.02);
(Continued)

(58) Field of Classification Search
CPC .. A61M 16/00; A61M 16/0463; A61M 16/06; A61M 16/0666; A61M 16/0672;
(Continued)

(56) References Cited

U.S. PATENT DOCUMENTS

2003/0047185 A1* 3/2003 Olsen ................ A61M 16/0633
128/203.22
2005/0229926 A1   10/2005 Fink et al.
(Continued)

FOREIGN PATENT DOCUMENTS

GB         2465358 A  * 5/2010  ........ A61M 16/1075
WO    WO-2014116122 A1 * 7/2014  ........ A61M 16/0858
(Continued)

OTHER PUBLICATIONS

International Search Report and Written Opinion in PCT Application PCT/NZ2017/050109 dated Nov. 14, 2017 in 18 pages.
(Continued)

*Primary Examiner* — Joseph D. Boecker
(74) *Attorney, Agent, or Firm* — Knobbe, Martens, Olson & Bear, LLP

(57) ABSTRACT

An adaptor for a respiratory assistance system delivers aerosols to a patient. The adaptor is lightweight with a small footprint to increase patient comfort. The adaptor has a nozzle and a sealing mechanism to maintain pressure therein regardless of whether the nozzle is inserted into the adaptor. The adaptor is configured to connect to medical tubing and a medicament delivery device.

18 Claims, 75 Drawing Sheets

Figure 1:
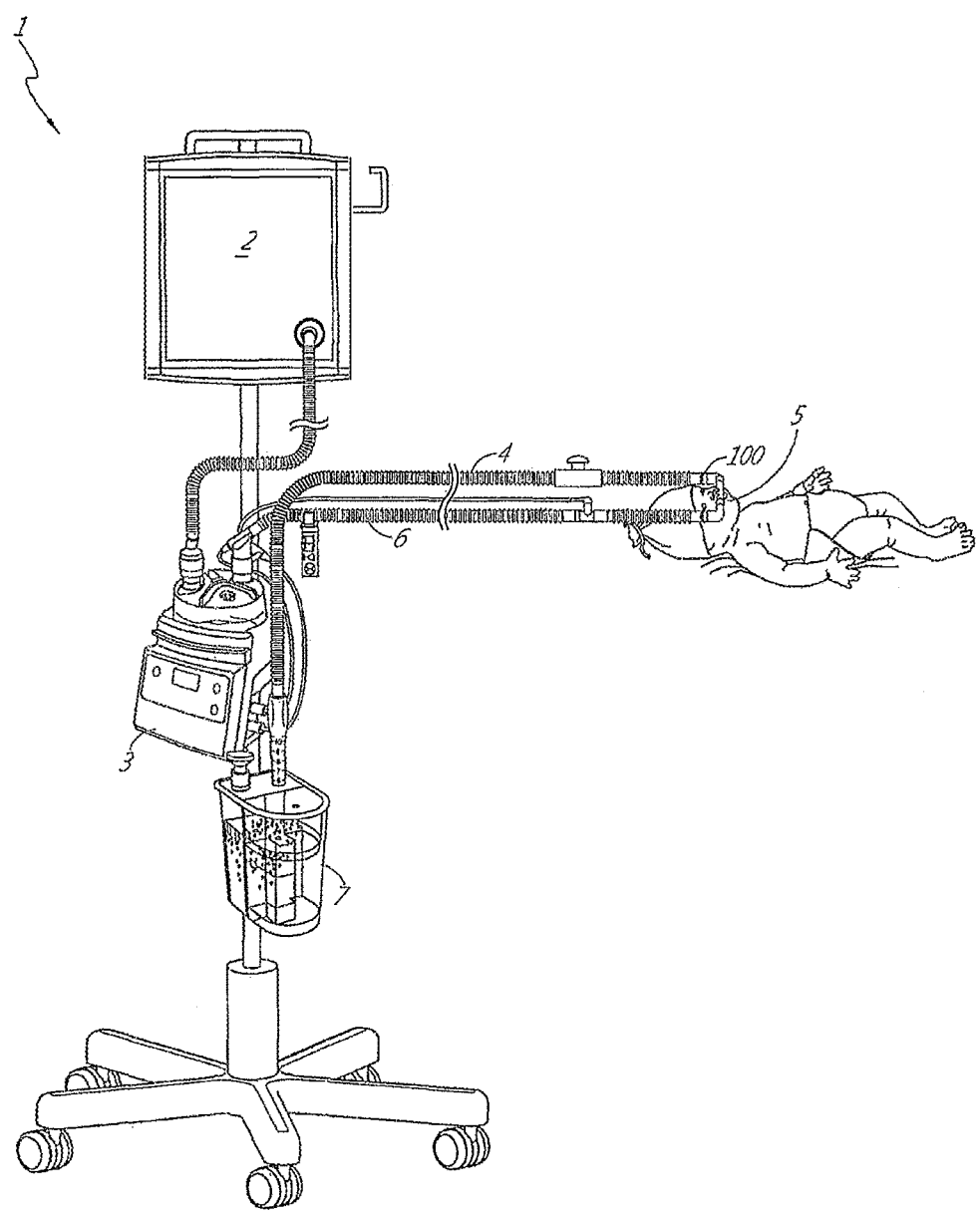

(51) Int. Cl.
  *A61M 16/14* (2006.01)
  *A61M 11/00* (2006.01)
  *A61M 15/00* (2006.01)
  *A61M 16/00* (2006.01)
  *A61M 16/16* (2006.01)

(52) U.S. Cl.
  CPC .... *A61M 16/0816* (2013.01); *A61M 16/0858* (2014.02); *A61M 16/14* (2013.01); *A61M 11/00* (2013.01); *A61M 15/009* (2013.01); *A61M 16/06* (2013.01); *A61M 16/0666* (2013.01); *A61M 16/16* (2013.01); *A61M 2016/0027* (2013.01); *A61M 2202/0488* (2013.01); *A61M 2205/3348* (2013.01); *A61M 2240/00* (2013.01)

(58) Field of Classification Search
  CPC .......... A61M 16/0683; A61M 16/0816; A61M 16/14; A61M 16/147; A61M 2016/0027; A61M 2202/0488; A61M 11/00; A61M 15/009
  See application file for complete search history.

(56) References Cited

U.S. PATENT DOCUMENTS

| | | | |
|---|---|---|---|
| 2008/0264412 A1* | 10/2008 | Meyer | A61M 15/009 128/200.22 |
| 2012/0017901 A1* | 1/2012 | Mainusch | A61M 16/0644 128/203.12 |
| 2013/0146053 A1 | 6/2013 | Mazela et al. | |
| 2014/0000626 A1 | 1/2014 | O'Connor et al. | |
| 2014/0158123 A1 | 6/2014 | Mazela et al. | |
| 2018/0043126 A1* | 2/2018 | Kemps | A61M 11/04 |
| 2020/0368483 A1* | 11/2020 | Duffy | A61M 16/0816 |

FOREIGN PATENT DOCUMENTS

| | | |
|---|---|---|
| WO | WO 2015/057083 | 4/2015 |
| WO | WO 2016/159784 | 10/2016 |
| WO | WO 2018/034574 | 2/2018 |

OTHER PUBLICATIONS

International Preliminary Report on Patentablity in PCT Application PCT/NZ2017/050109 dated Feb. 19, 2019 in 10 pages.

* cited by examiner

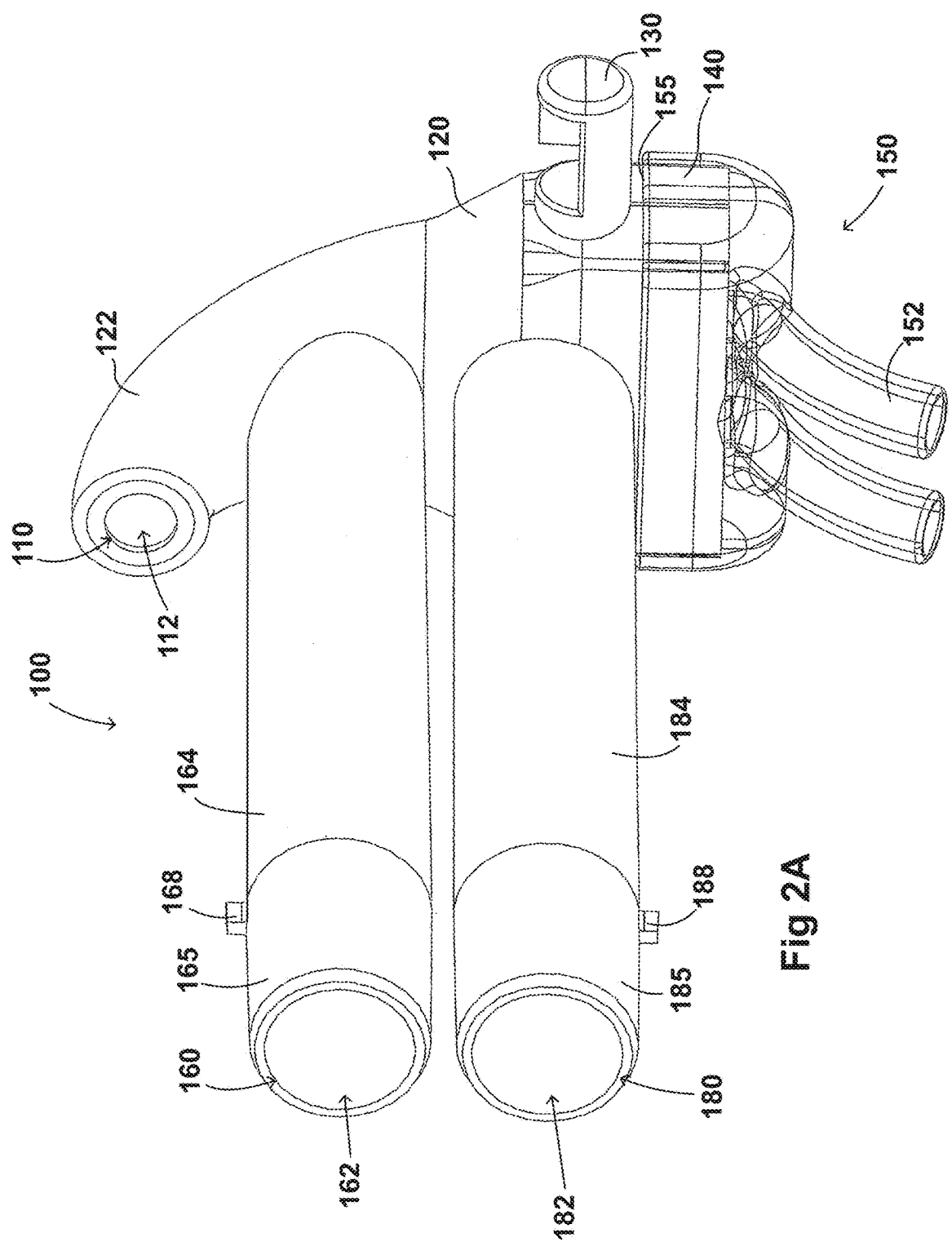

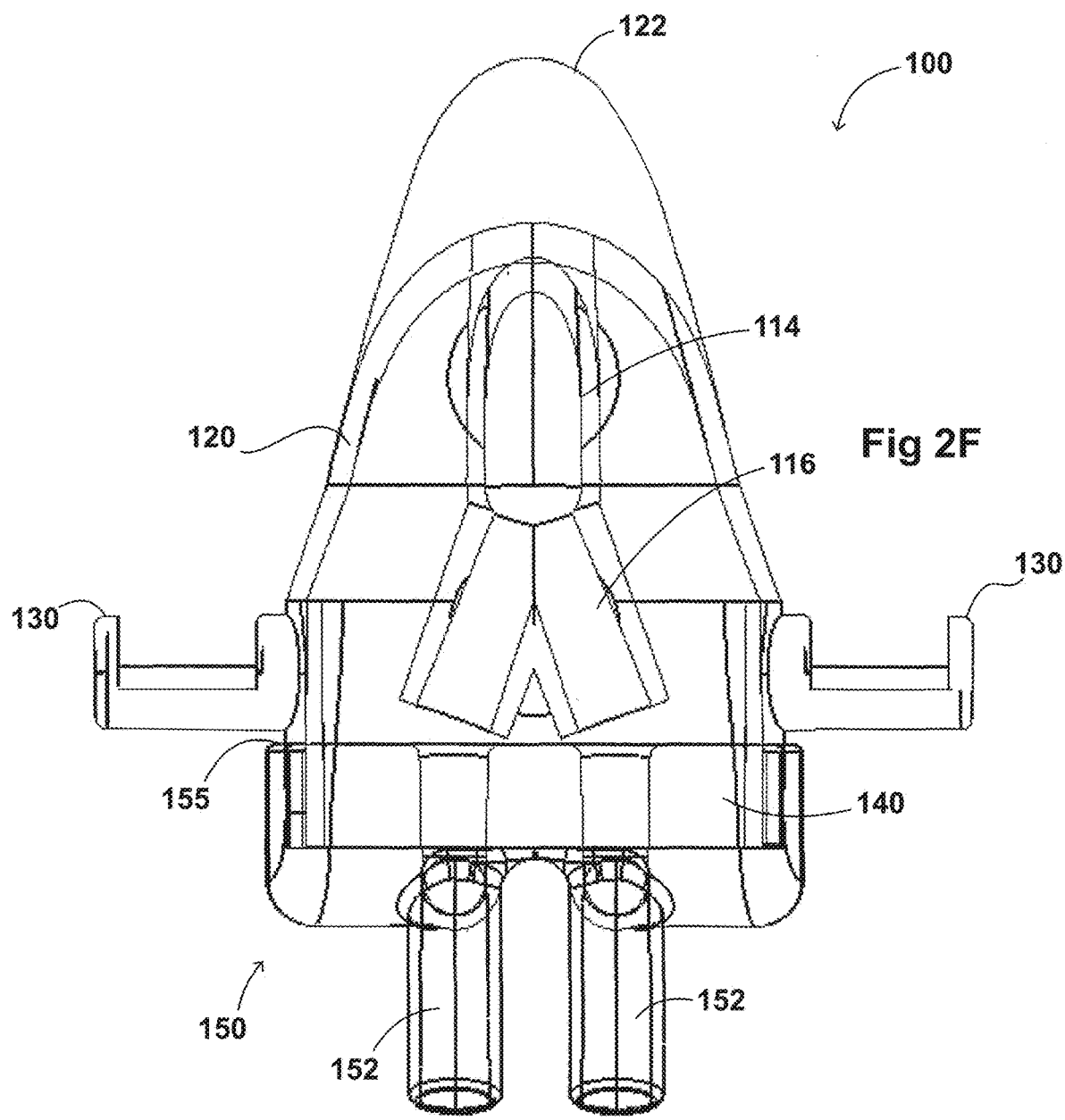

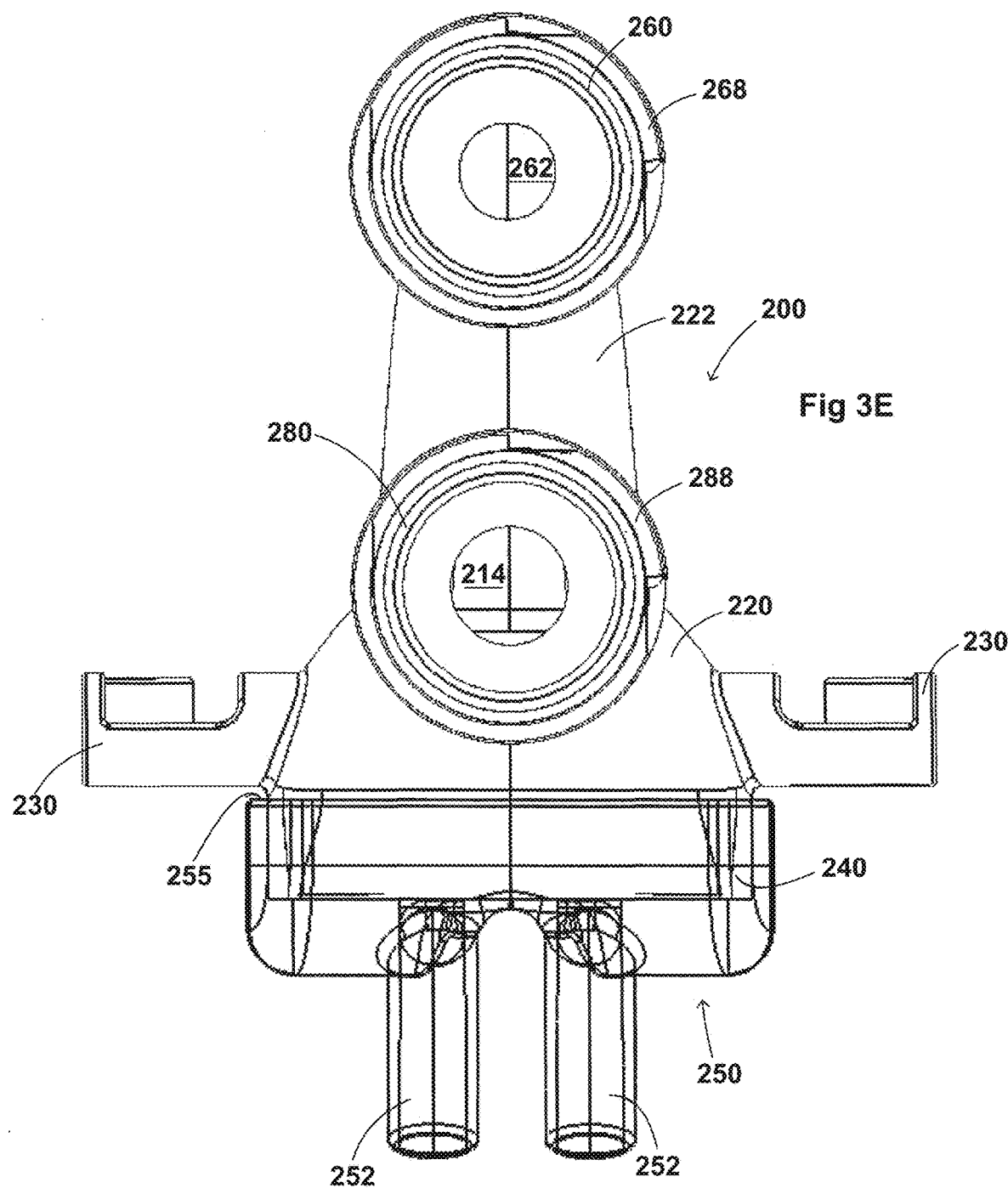

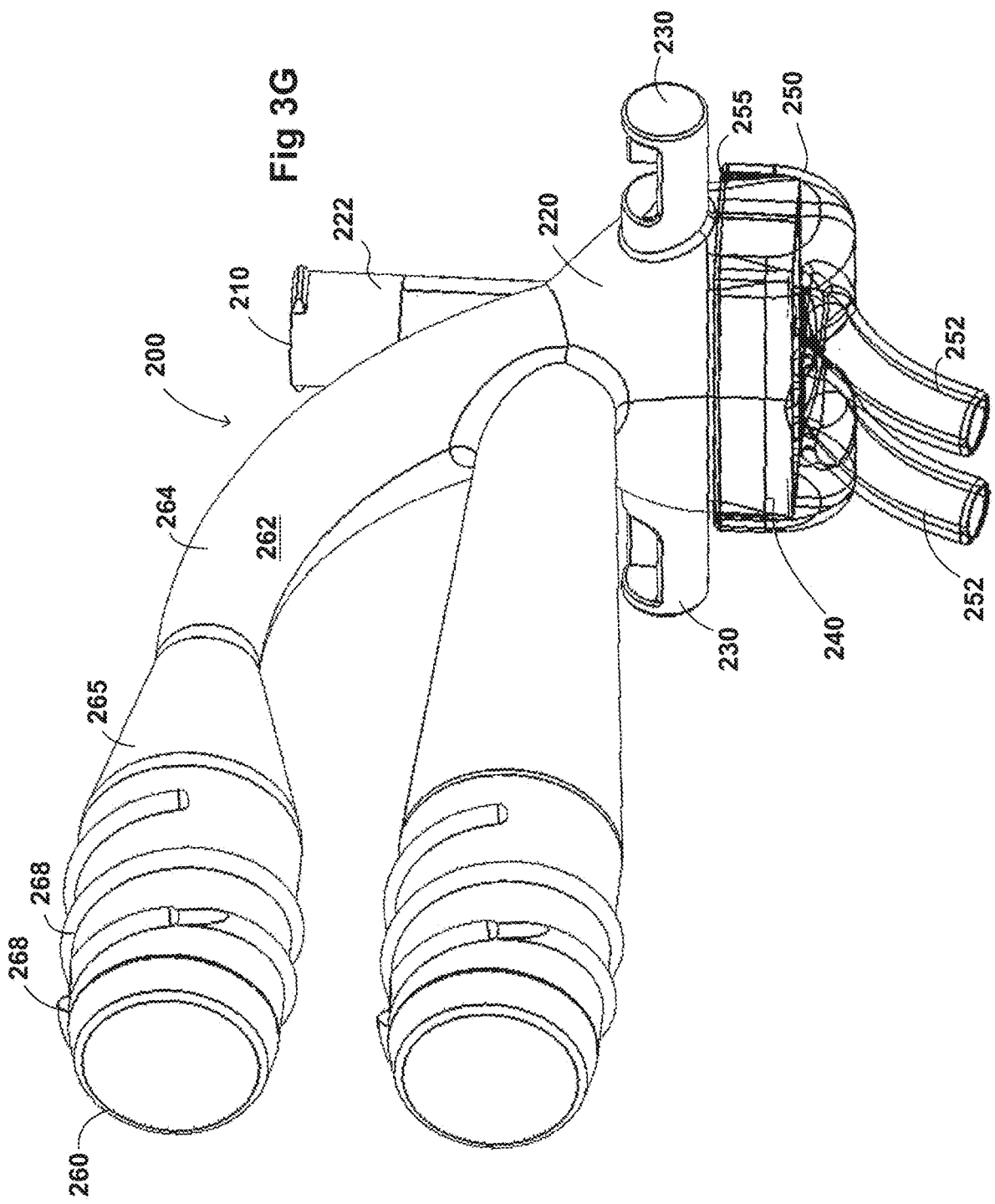

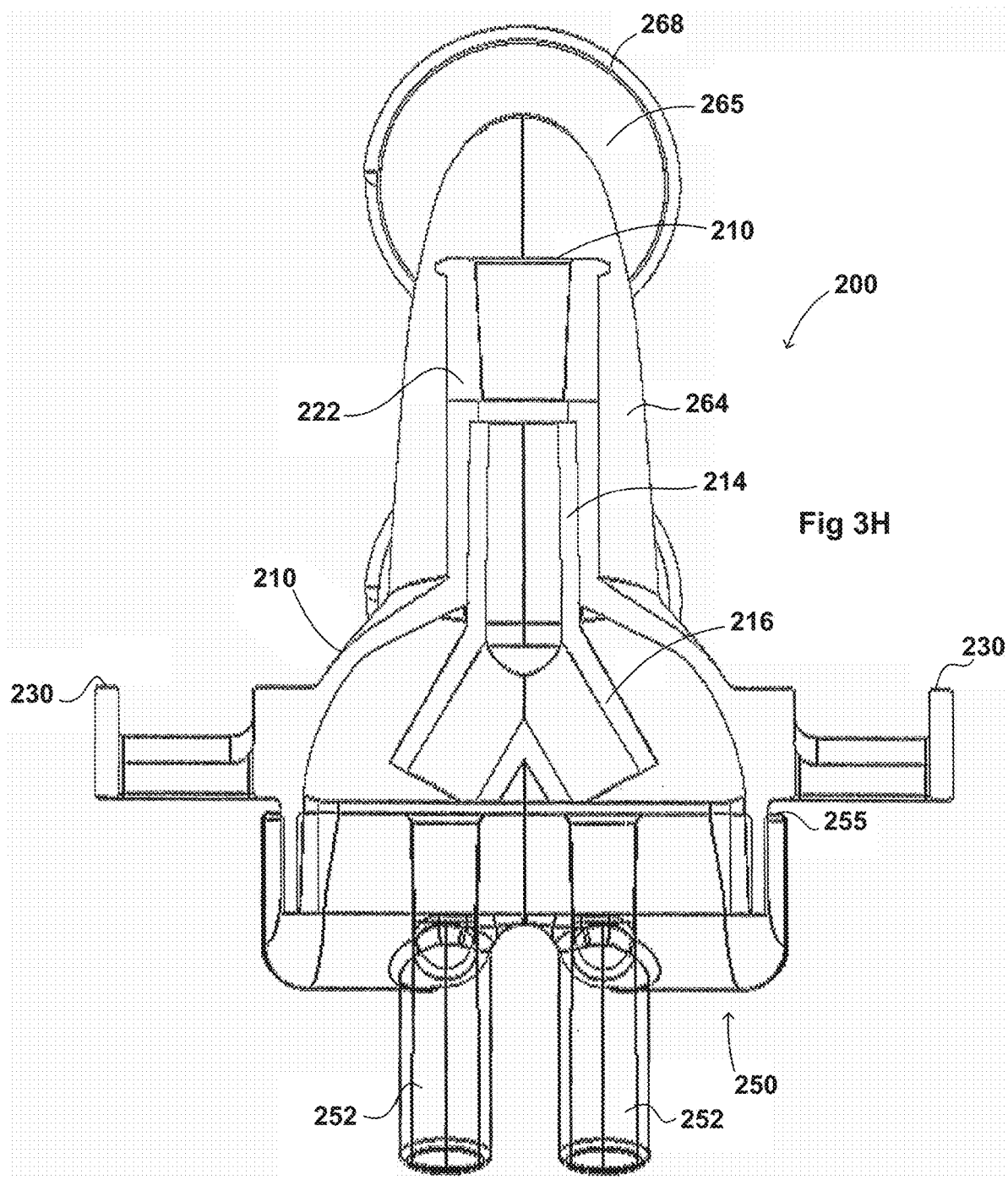

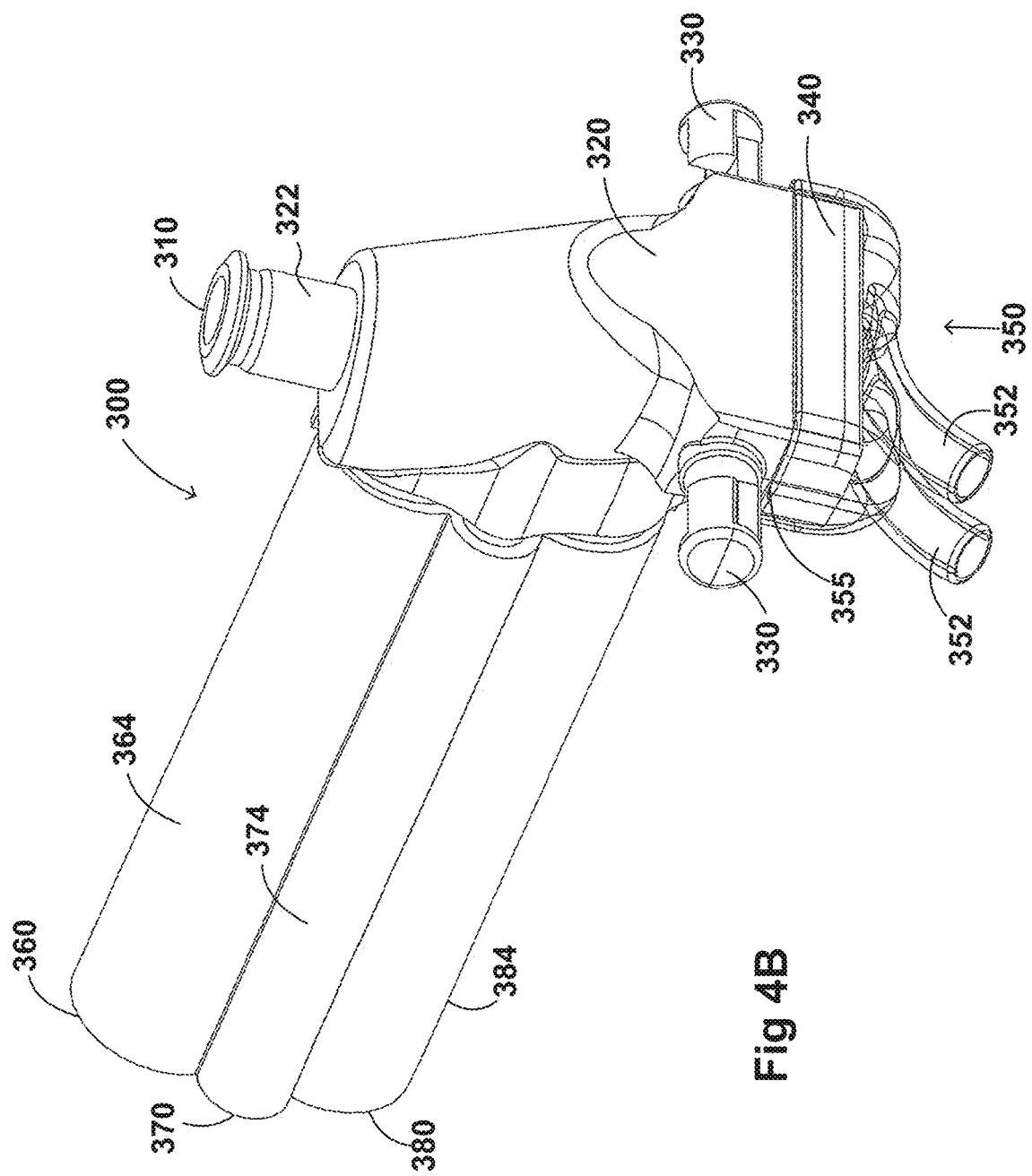

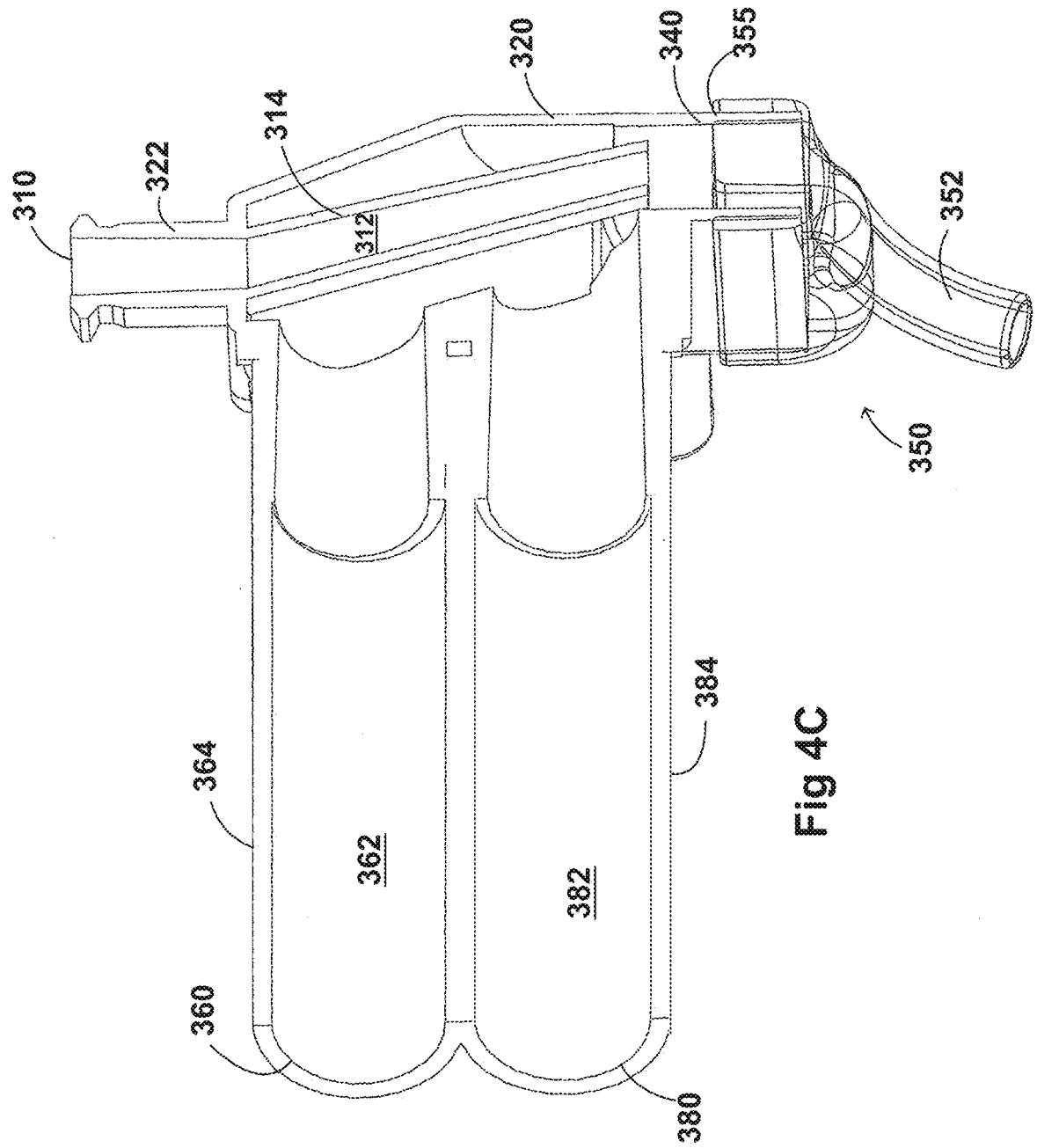

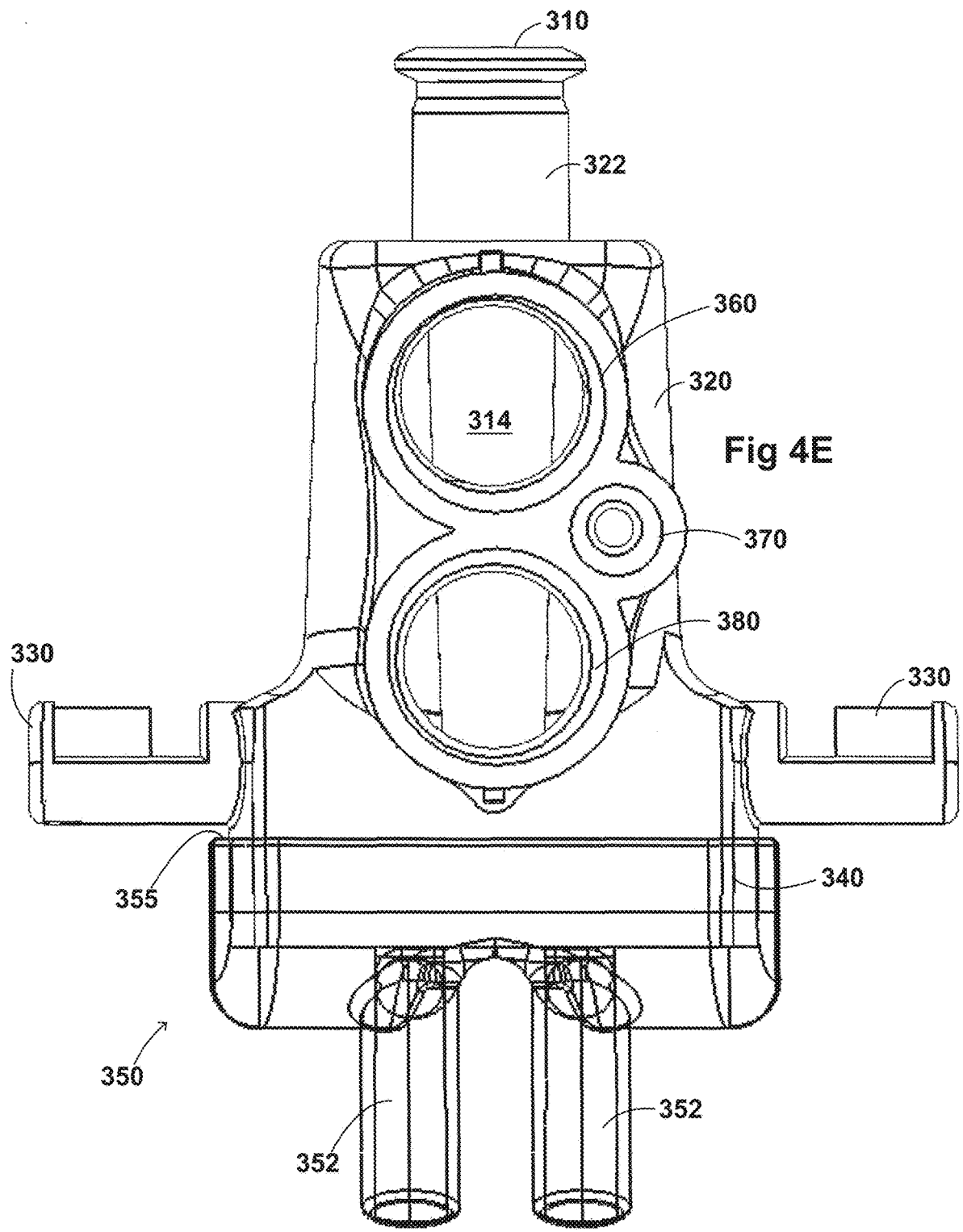

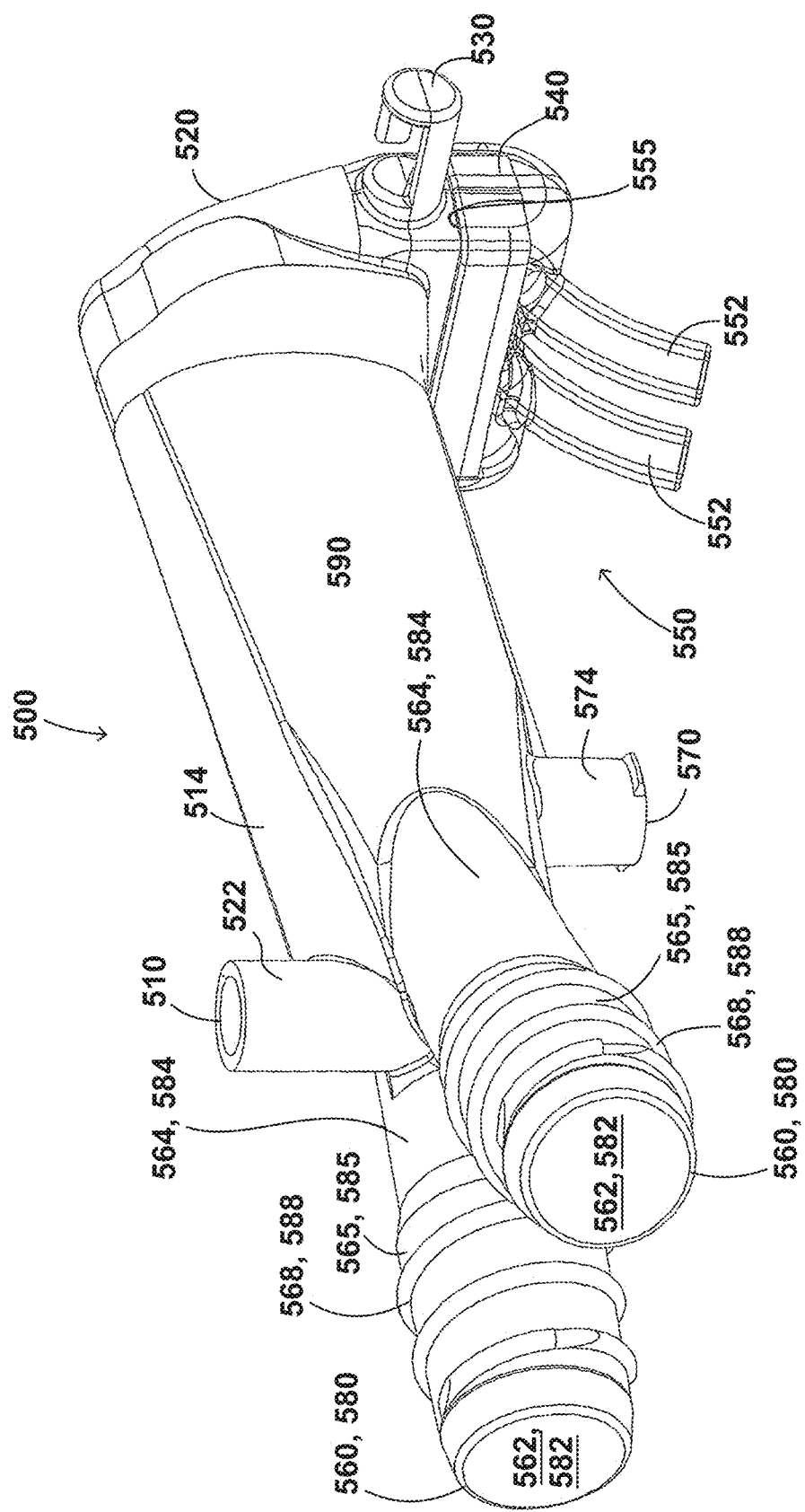

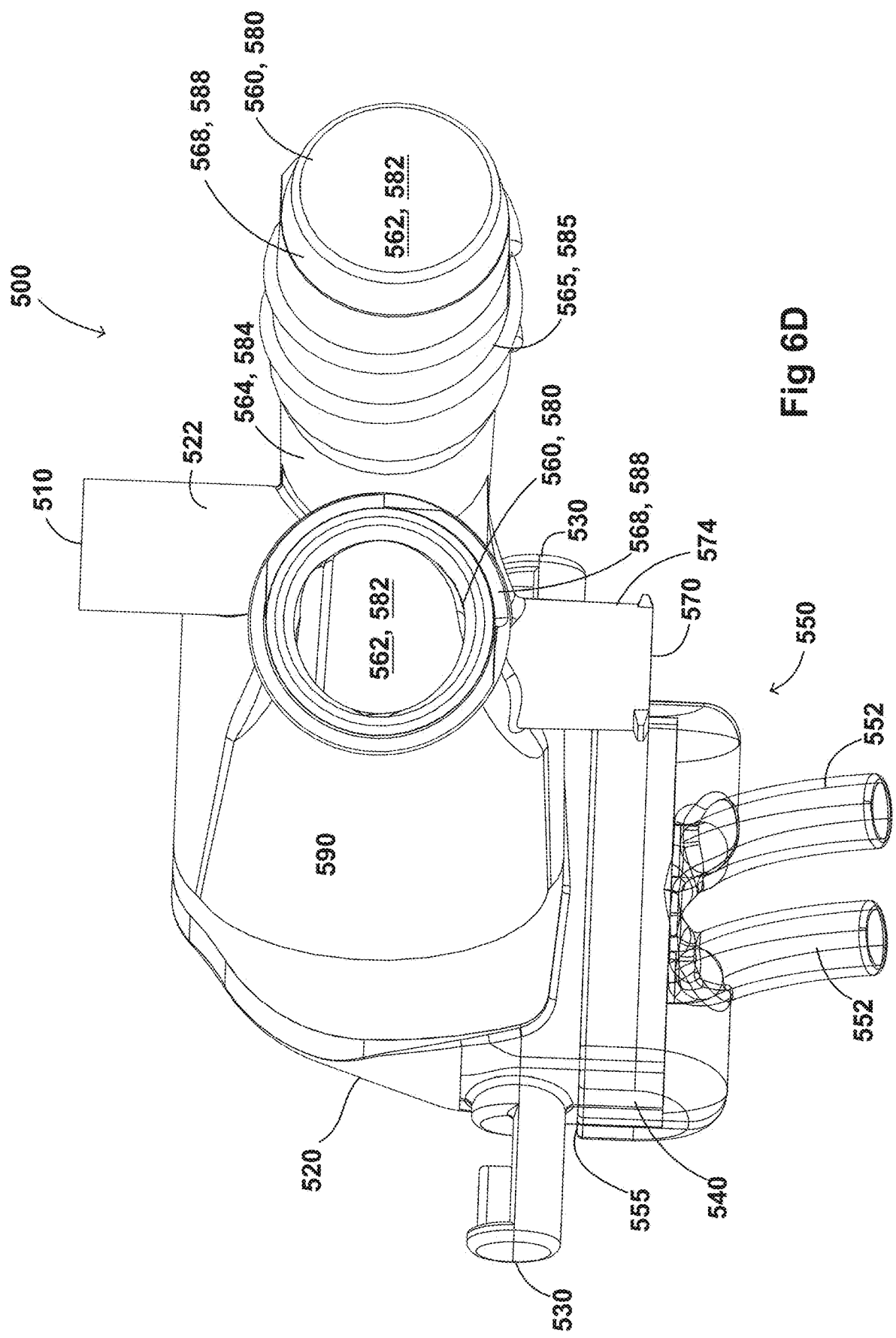

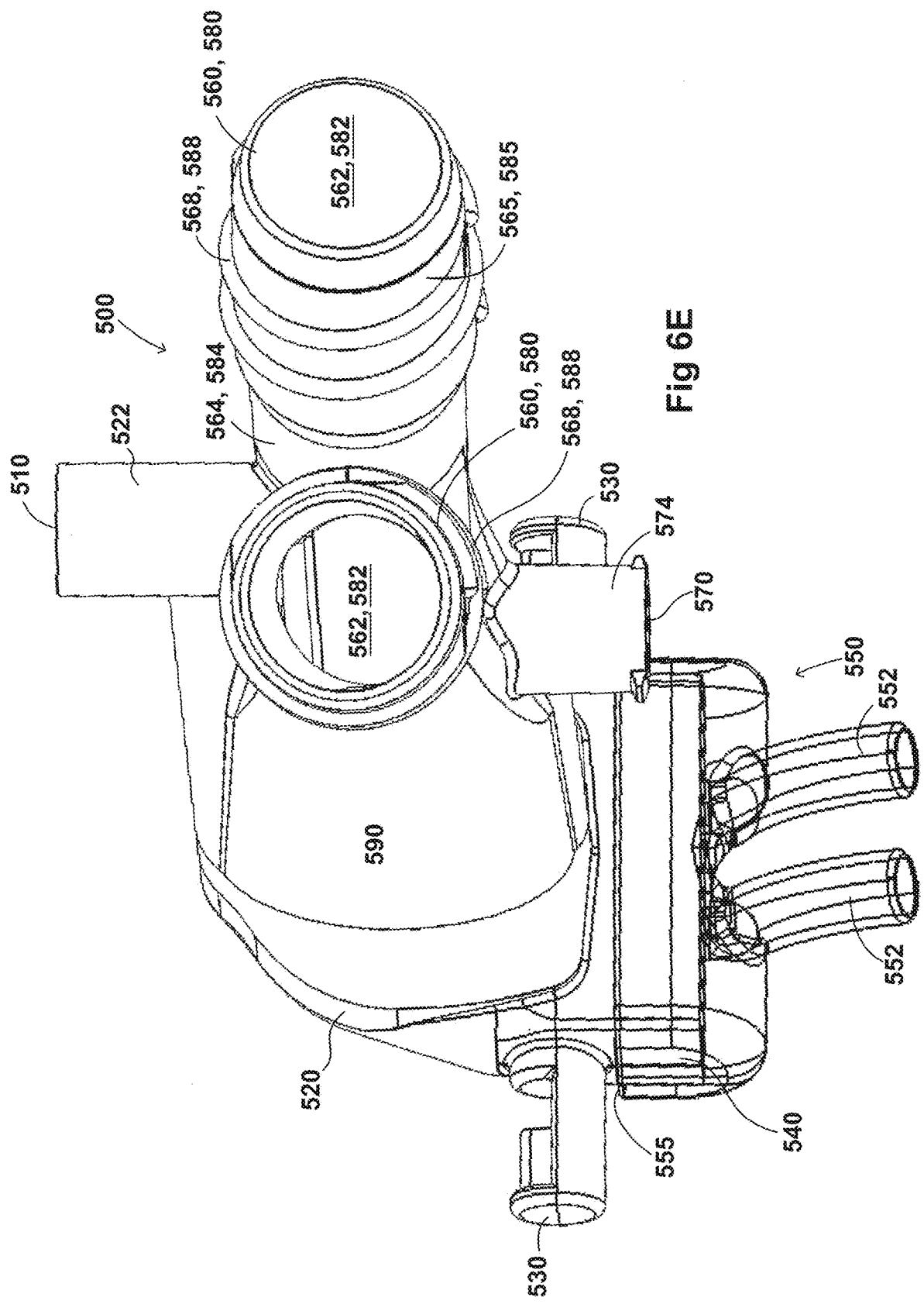

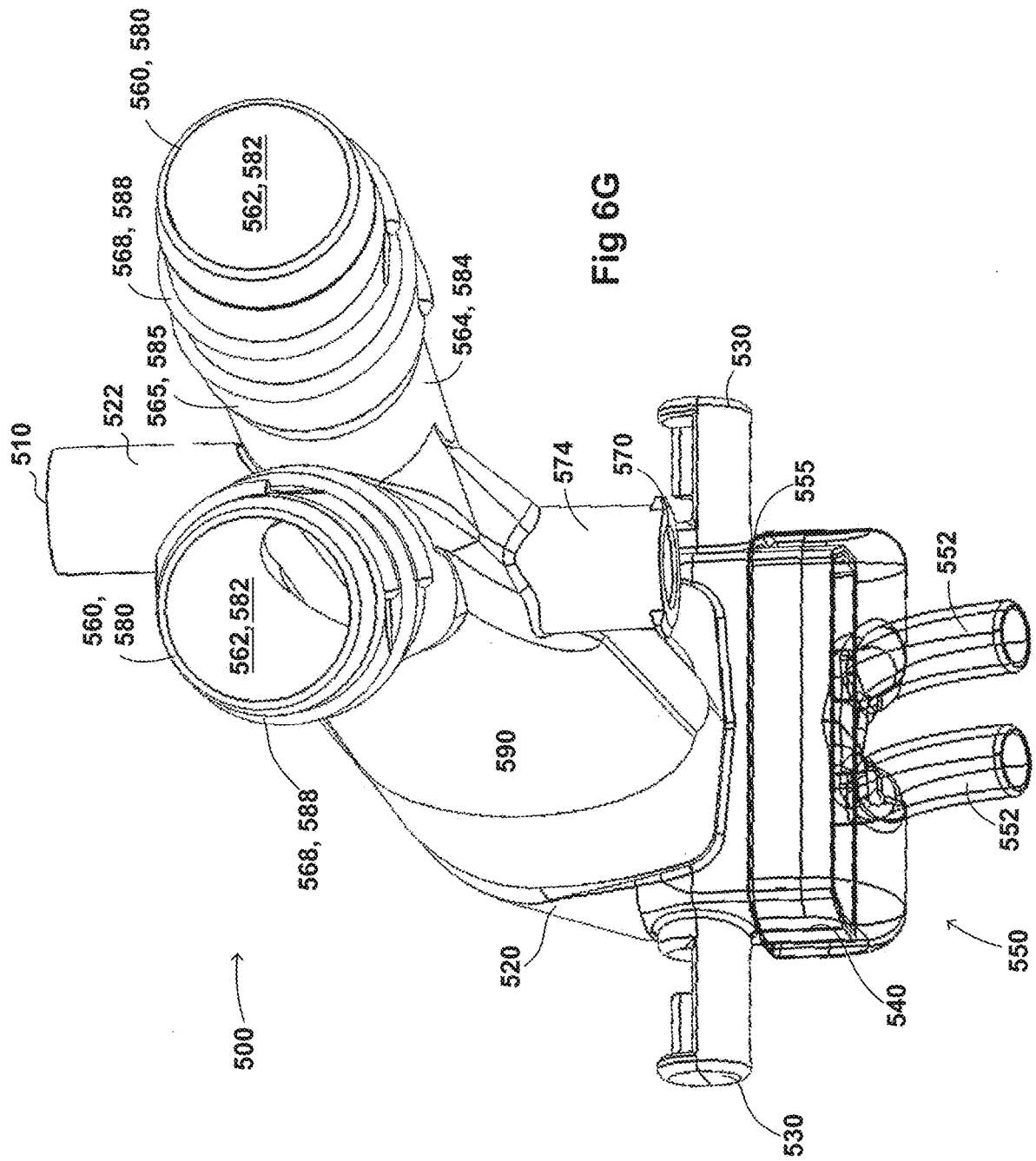

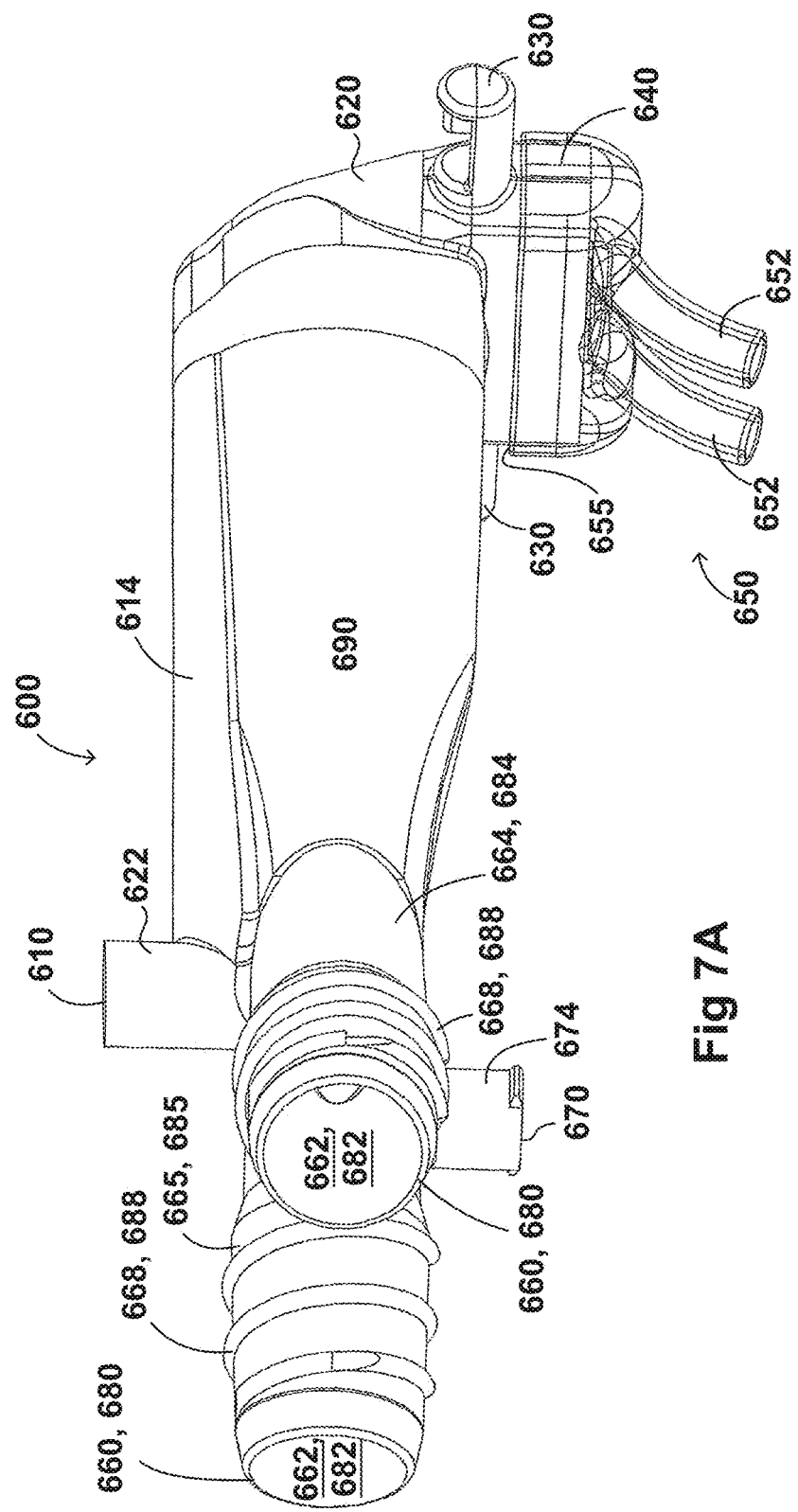

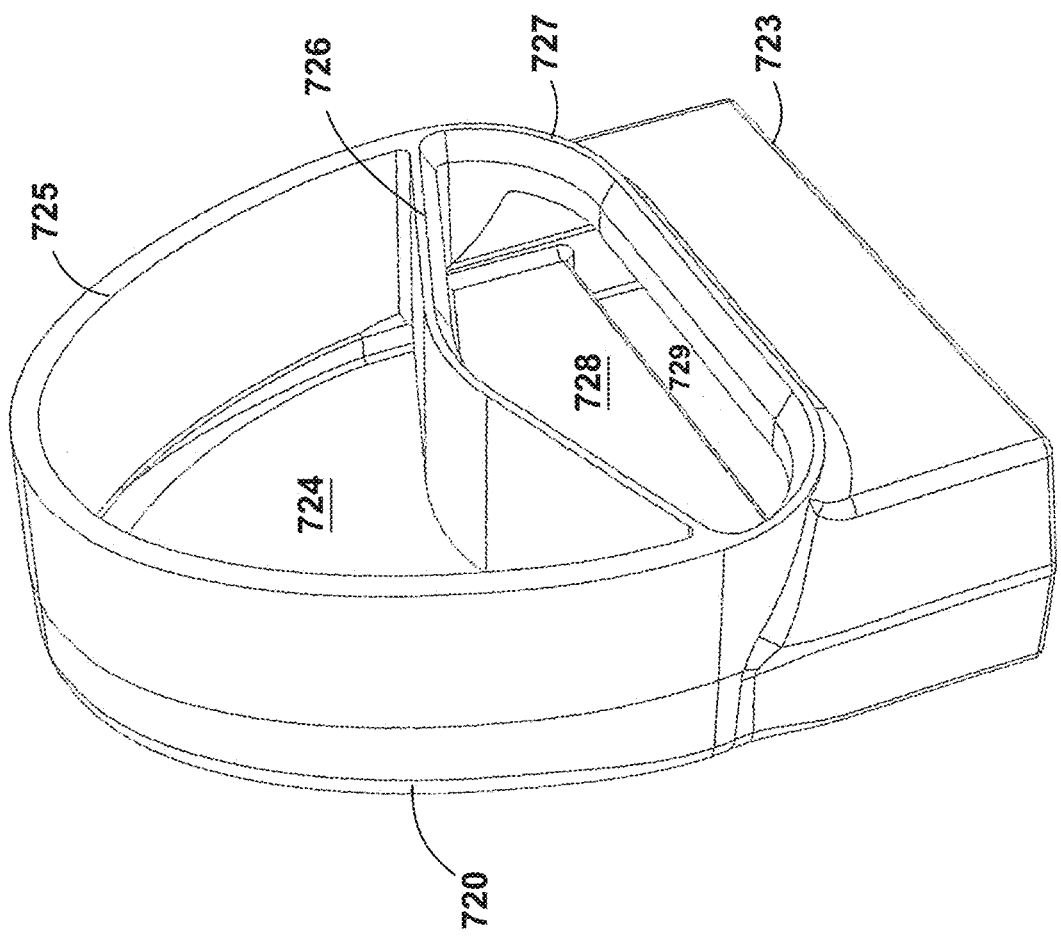

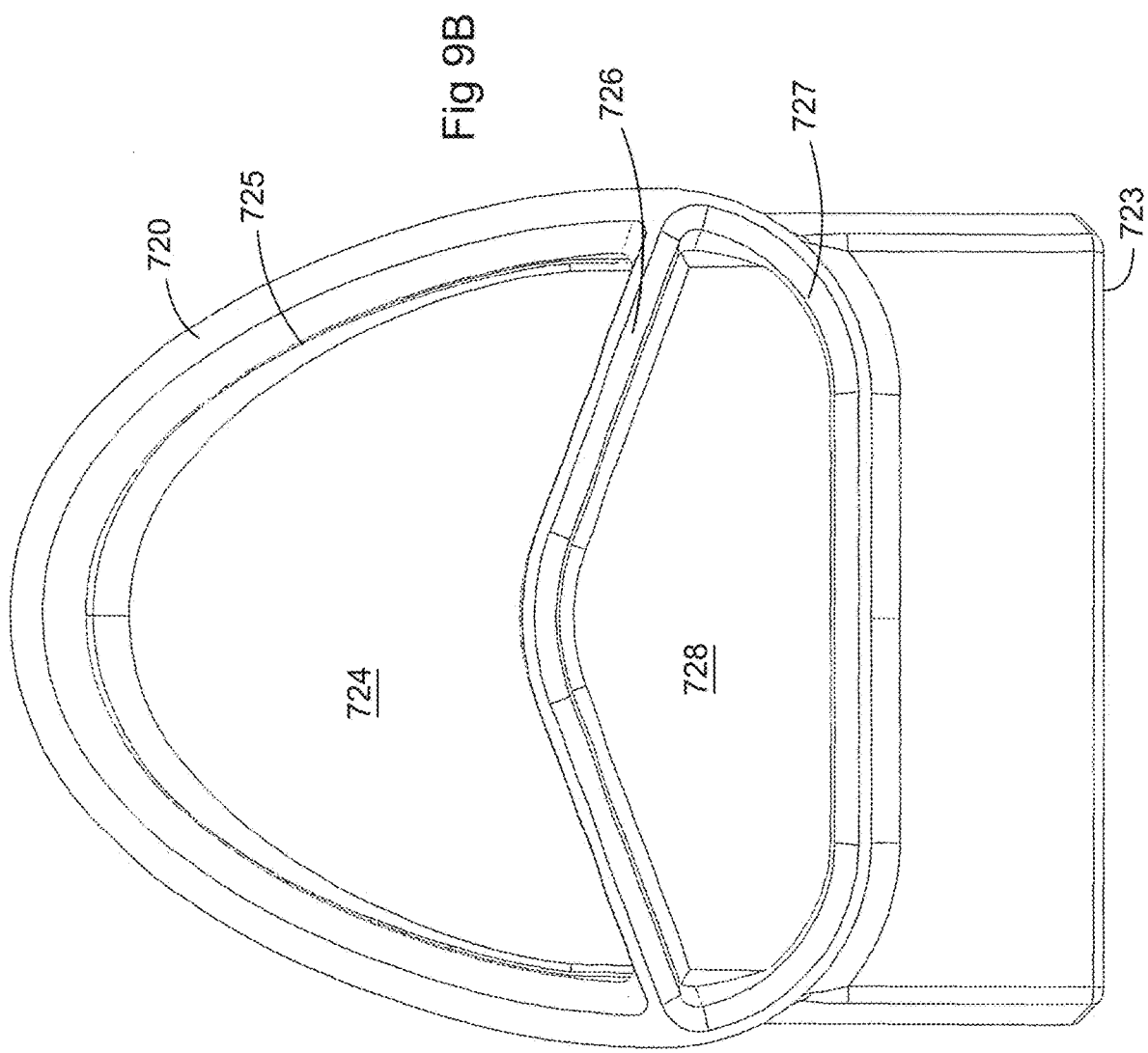

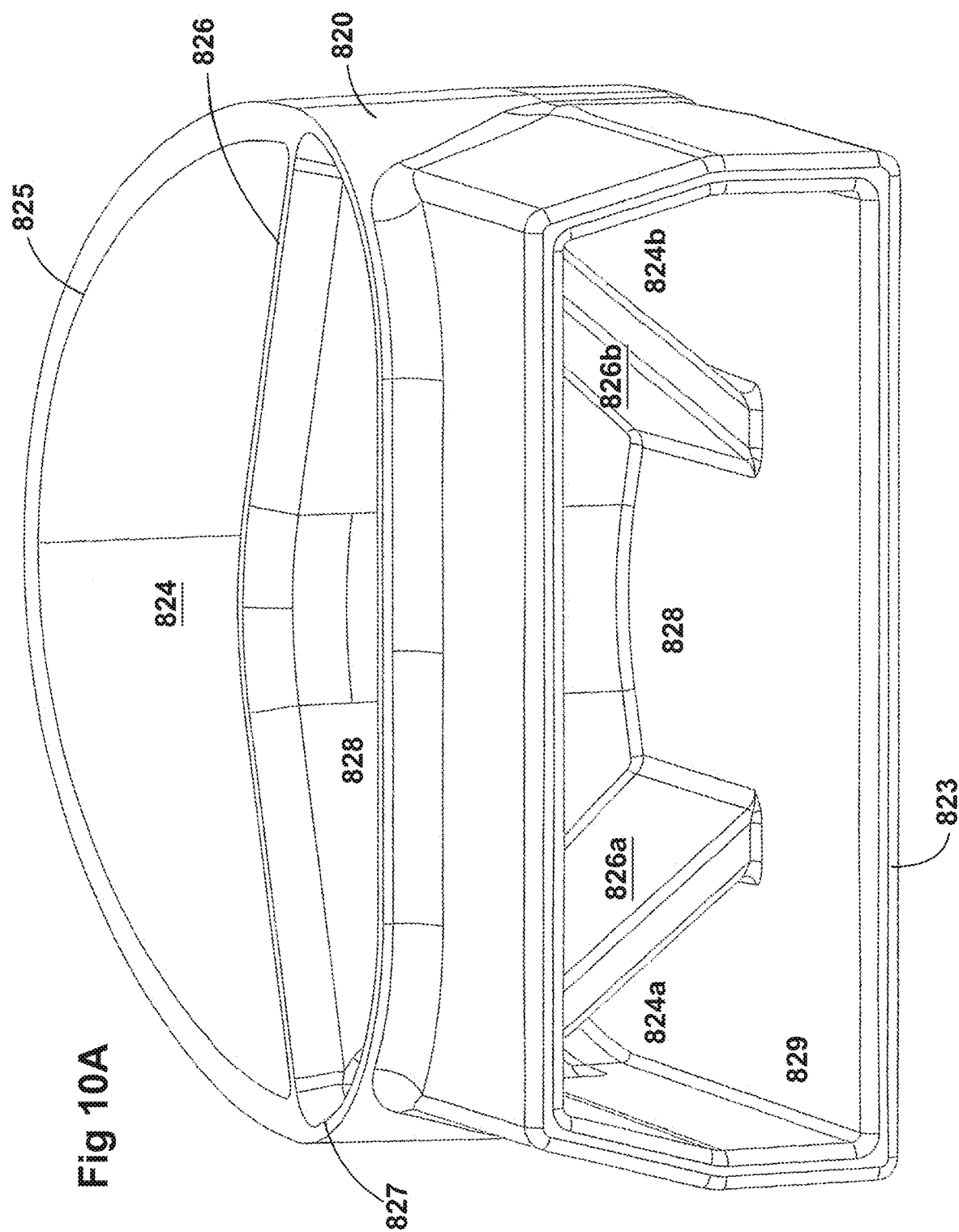

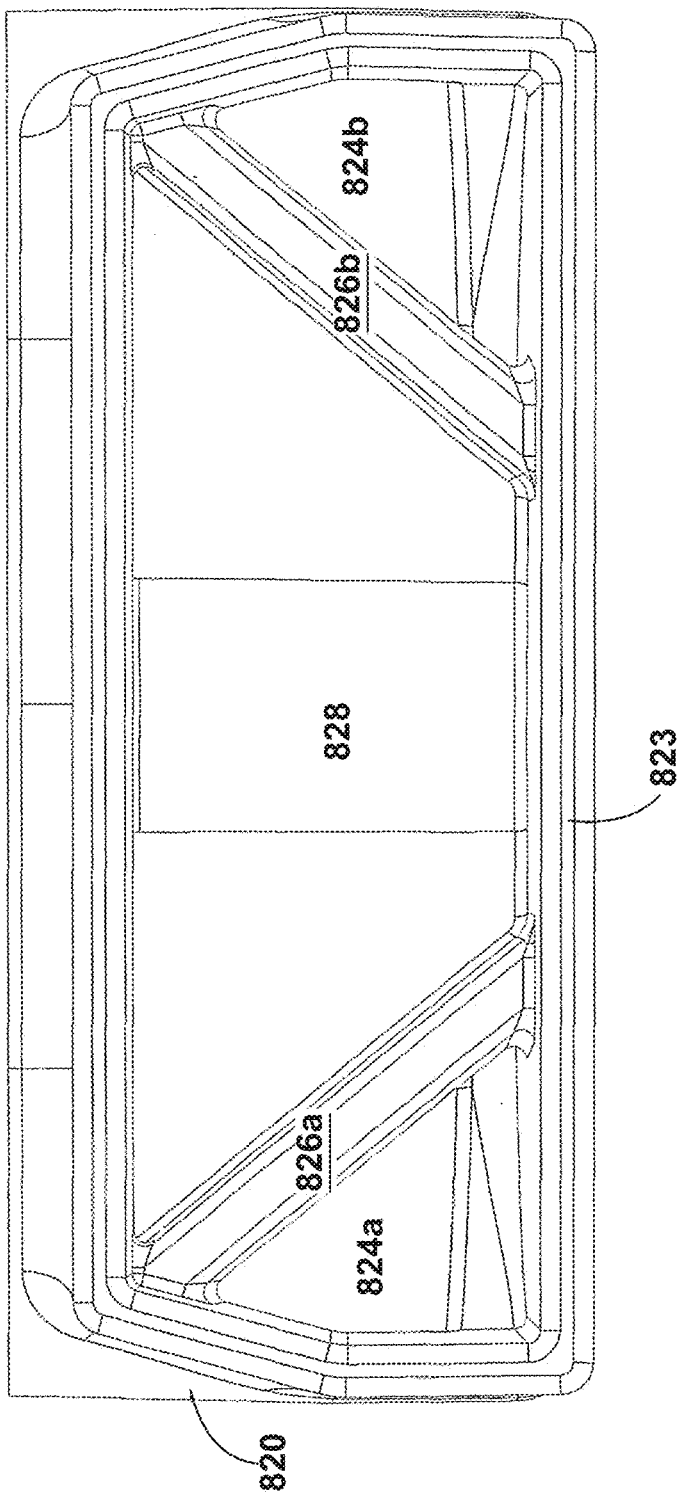

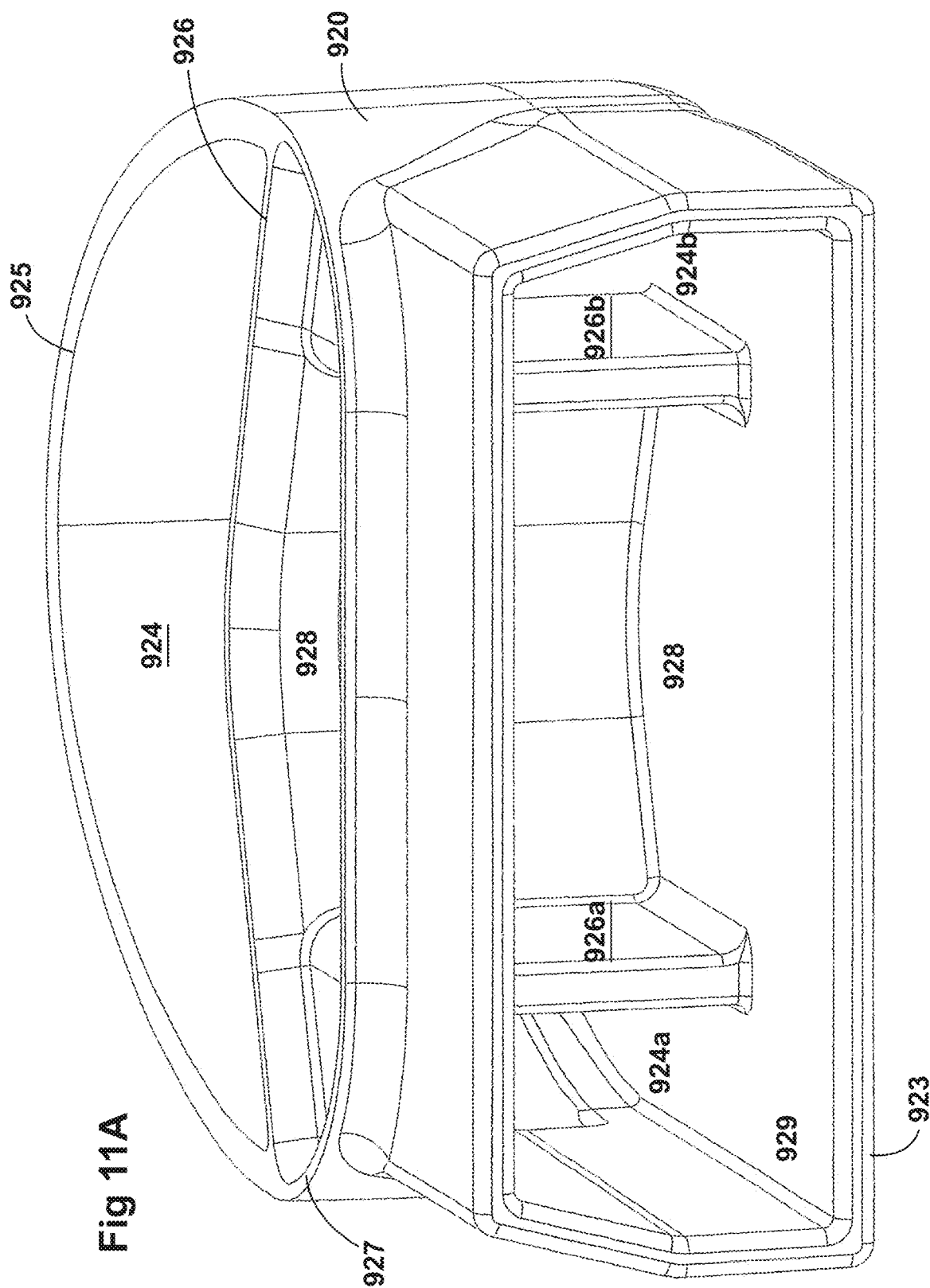

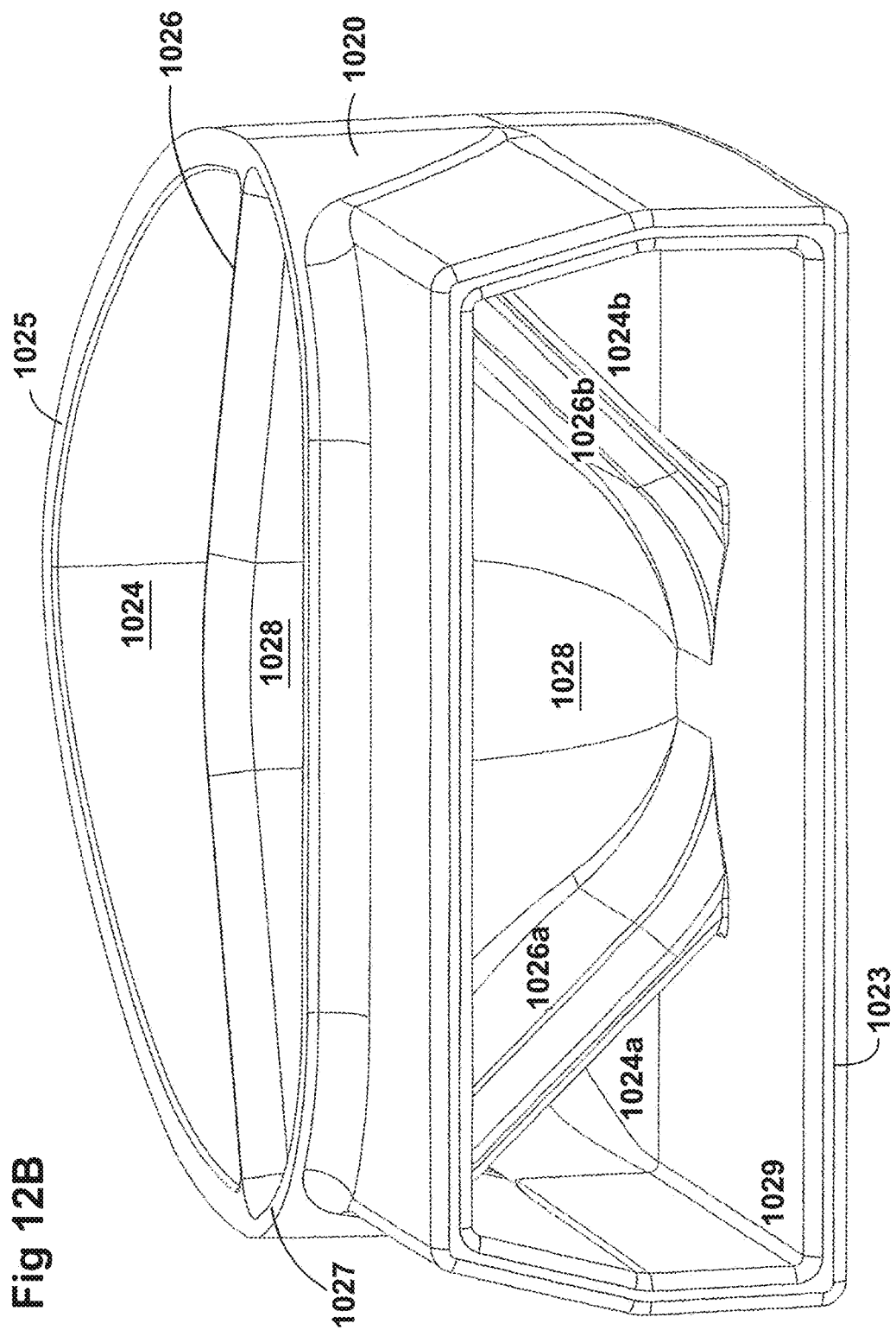

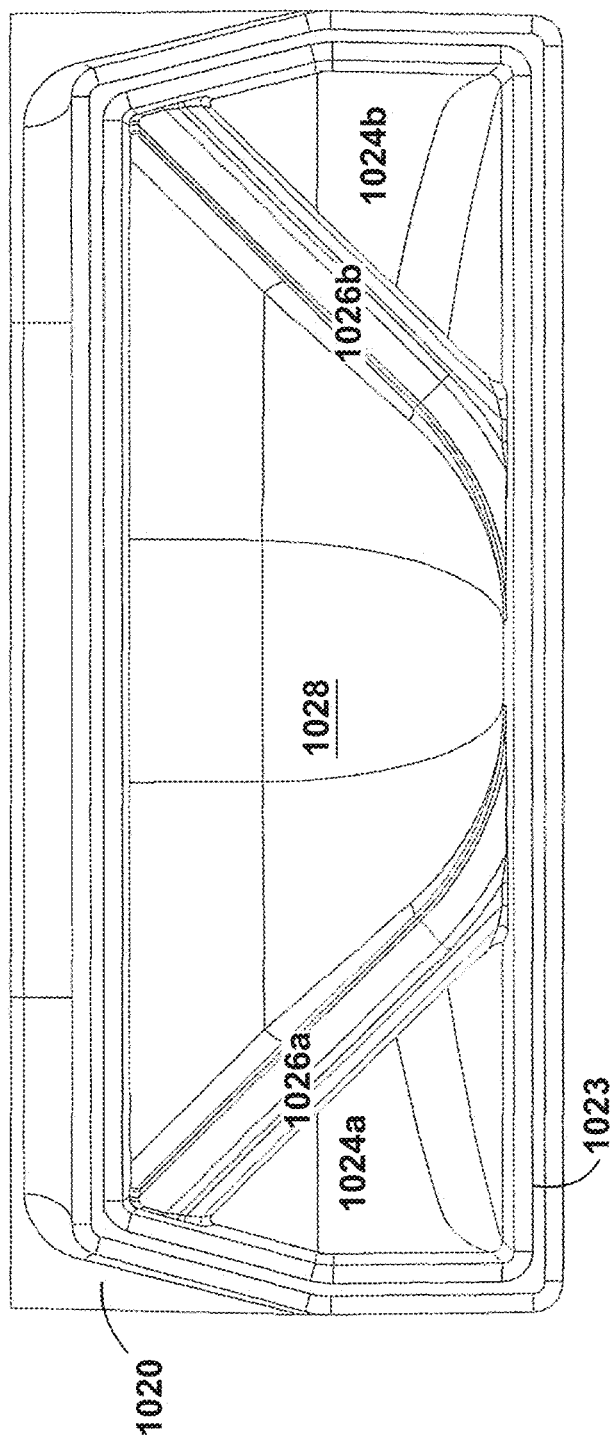

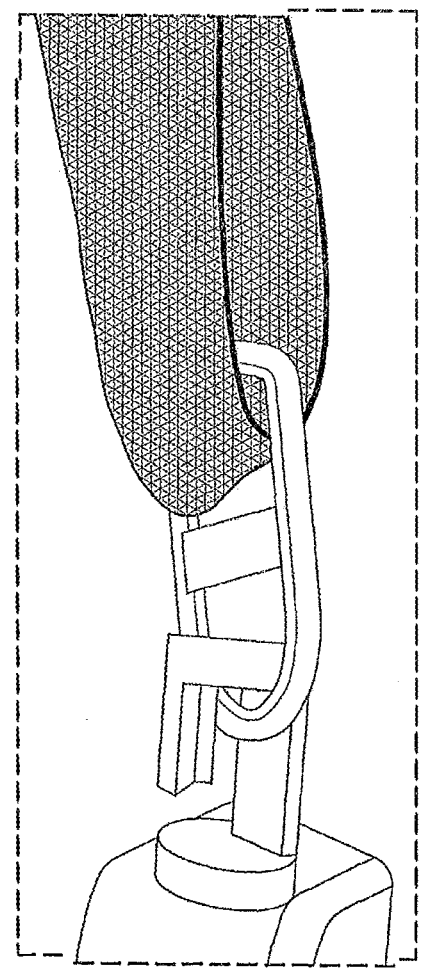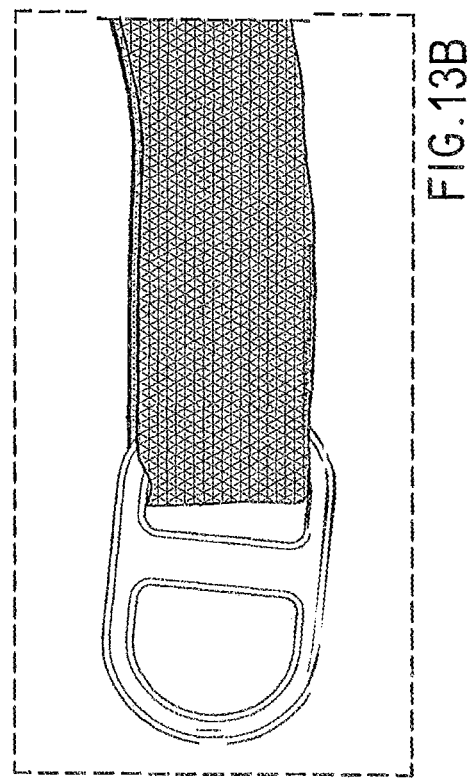

ADAPTOR FOR RESPIRATORY ASSISTANCE SYSTEMS

INCORPORATION BY REFERENCE TO ANY PRIORITY APPLICATIONS

This application is a U.S. National Phase application of PCT Application No. PCT/NZ2017/050109, filed Aug. 15, 2017, which claims priority from provisional patent applications U.S. Provisional Application No. 62/427,796 and U.S. Provisional Application No. 62/375,405, the entire contents of each of which are hereby incorporated by reference.

FIELD OF THE DISCLOSURE

The present disclosure generally relates to delivering medical gases to a patient. More particularly, the present disclosure relates to an adaptor or patient interface or both configured to couple with a respiratory assistance system to deliver medical gases to an infant.

BACKGROUND

Gases delivery adaptors are configured to couple between a medical apparatus and a patient interface to aid with the delivery of gases or aerosolised substances.

Respiratory systems may deliver conditioned gases to a patient. Gases are heated and humidified prior to delivery to mimic the transformation of gases that occurs as they travel from the nose to the lungs in a healthy individual. This improves airway defence and gases exchange in the lungs when compared with the delivery of cold, dry gases to a patient. Medicament delivery devices, for example, nebulisers, capillary aerosol generators or metered dose inhalers (MDIs) couple with respiratory systems to deliver medicaments, such as aerosols, dry powders or aerosolised surfactant to a patient during respiratory treatment. Adaptors are used to couple medicament delivery devices with respiratory systems.

Bubble Continuous Positive Airway Pressure (CPAP) is a therapy that can provide respiratory support to infants. This includes maintaining the functional residual capacity of the lungs, which can help to prevent the airways from closing and maintains the energy reserves of infants without requiring invasive ventilation. Gases delivered to patients via a bubble CPAP system may be heated and humidified, which minimises airway drying and inflammation, while improving secretion clearance and ventilation. As a result, use of a conditioned bubble CPAP system may reduce the time an infant is hospitalised. Bubble CPAP therapy can be delivered using a patient interface, such as a mask, or nasal prongs. Aerosols can be administered to a patient through the patient interface.

SUMMARY

A medical gases delivery adaptor is disclosed herein in various embodiments. The adaptor comprises a housing with an inlet port and an outlet port that couples with medical tubing. A patient interface couples with the housing to deliver gases to a patient. The housing can include a nozzle that is configured to fluidly couple with a medicament delivery device, and can be configured to deliver aerosolised gases, medicament or aerosolized surfactant or aerosolized drugs or aerosolized medicament to the patient.

For purposes of summarising the present disclosure, certain aspects, advantages and novel features of the disclosed apparatus and systems have been described herein. It is to be understood that not necessarily all such advantages may be achieved in accordance with any particular embodiment of the disclosure. Thus, the disclosed apparatus and systems may be embodied or carried out in a manner that achieves or optimises one advantage or group of advantages as taught herein without necessarily achieving other advantages as may be taught or suggested herein.

According to at least one aspect of the present disclosure, a respiratory system component can include one, some, or all of the following features, as well as other features described herein. The respiratory system component comprises a housing, an inlet port, and an outlet port. The housing comprises a first end and a second end. The housing defines a passageway between the first end and the second end. The inlet port is coupled with the housing. The inlet port is configured to couple with a first conduit. The outlet port is coupled with the housing. The outlet port is configured to couple with a second conduit. The first end of the housing can be fluidly connected to a nozzle. In some examples, the nozzle can deliver drug to the housing and to the patient. The second end of the housing can be configured to couple with a patient interface.

In some embodiments, the housing can optionally include at least one clip configured to facilitate attachment of a headgear to the respiratory system component. The respiratory system component can optionally include a coupling surface in fluid communication with the second end of the housing. The coupling surface can optionally be configured to receive the patient interface by a friction fit. The patient interface can optionally include nasal prongs or a nasal mask. The nozzle can optionally be configured to fluidly connect the passageway of the housing with a medicament delivery device.

In some embodiments, disclosed is an adaptor for medicament delivery comprising a tubular body, a housing, and a patient interface. In some embodiments, the tubular body has a first end and a second end and includes an inlet tube, an outlet tube, and a surfactant delivery tube. The inlet tube can include an inlet port at the first end and an outlet at the second end, wherein the inlet port is configured to be connected to an inspiratory conduit for receiving a flow of gases. The outlet tube can be adjacent to the inlet tube having an outlet port at the first end and an inlet at the second end, wherein the outlet port is configured to be connected to an expiratory conduit for dispensing the flow of gases. The surfactant delivery tube can be adjacent to a portion of at least one of the inlet tube and the outlet tube and can include an inlet port at the first end and an outlet at a second end, wherein the inlet port is configured to connect to a source of medicament. In some embodiments, the housing includes a first end and a second end, wherein the first end of the housing is attached to the second end of the tubular body. The patient interface can be configured to be connected to the second end of the housing, wherein the patient interface is in fluid communication with an airway of a patient.

In other embodiments, the adaptor can include a housing that is permanently attached to the tubular body. In other embodiments, the adaptor includes a tubular body and housing comprising a rigid plastic. In other embodiments, the adaptor includes a flow of medicament comprising an aerosolized surfactant.

In other embodiments, the adaptor has a housing that includes a divider to separate the flow of gases from a flow of medicament. In some embodiments, at least a portion of the housing of the adaptor is configured to allow the flow of gases to mix with the flow of medicament. In some embodiments, the adaptor includes a divider that comprises angled sidewalls. In some embodiments, the adaptor includes a divider that further comprises a rounded portion connecting the angled sidewalls to improve fluid flow around corners. In some embodiments, the adaptor includes a divider that is configured to provide a plurality of fluid entryways into an interior of an undivided portion of the housing. In some embodiments, the adaptor includes a divider that comprises straight walls to form rectangular fluid entryways to the interior of the undivided portion of the housing. In some embodiments, the adaptor includes a housing wherein a cross-section of a portion of the housing in fluid communication with the surfactant delivery tube is greater than a cross-section of a portion of the housing in fluid communication with the inlet tube and the outlet tube, and wherein the greater cross-section of the portion of the housing in fluid communication with the surfactant delivery tube is configured to reduce deposition of medicament within the surfactant delivery tube.

In other embodiments, the adaptor includes a patient interface comprising a pair of prongs. In some embodiments, the adaptor includes nasal prongs that are sized to fit the nares of the patient. In some embodiments, the adaptor includes a patient interface that is configured to interchangeably attach to a plurality of different nasal prong sizes. In some embodiments, the adaptor includes a patient interface that is press-fit onto the second end of the housing. In some embodiments, the adaptor comprises a patient interface that is removably connected to the second end of the housing.

In other embodiments, the adaptor comprises a tubular body that further comprises a pressure port connected to a pressure sensor, wherein the pressure sensor is configured to measure air pressure flowing through the pressure port. In other embodiments, the adaptor comprises a tubular body that further comprises a pressure tube connected to the housing. In other embodiments, the adaptor comprises a pressure port and an inlet port of the surfactant delivery tube that are on opposing sides of the adaptor. In other embodiments, the adaptor comprises a tubular body having an elongated oval cross-section.

In other embodiments, the adaptor comprises an inlet port having threading to connect to an inspiratory conduit, and an outlet port having threading to connect to an expiratory conduit. In some embodiments, the adaptor comprises an inlet port and an outlet port wherein a portion of the inlet port and the outlet port are tapered. In some embodiments, the adaptor comprises an inlet port and outlet port that are tapered to 15 mm or 22 mm.

In other embodiments, the adaptor can further comprise at least one clip connectable to an interface stabilization mechanism. In some embodiments, the adaptor includes an interface stabilization mechanism that comprises headgear.

In other embodiments, the adaptor comprises a retaining system comprising a two-part releasable attachment system comprising an interface patch and a dermal patch. In some embodiments, the adaptor comprises a two-part releasable attachment system that is foldable. In some embodiments, the adaptor comprises a two-part releasable attachment system that is configured to retain at least one of a surfactant tube, a pressure sensor line, and a feeding tube. In some embodiments, the adaptor comprises a two-part releasable attachment system that comprises a dynamic interface having a hinge configured to conform the dynamic interface to the shape of the face of the patient, and wherein the dynamic interface is configured to maintain the position of the prongs on the face of the patient by minimizing movement of the prongs.

In other embodiments, the adaptor further comprises a foam block configured to stabilize the adaptor on the face of the patient. In other embodiments, the adaptor is configured such that the bias air flow path through the adaptor occurs upstream from the flow of medicament.

In the above disclosed embodiments, surfactant (e.g. medicament) can be delivered to the air flow path after the exchange of air from the inlet lumen and the outlet lumen ensures less dilution of the surfactant to the infant as well as reducing the deposition of the surfactant on the interior of the adaptor. In some examples, the inside of the housing can include a divider that divides the housing to provide a housing airflow entrance fluidly connected to a housing airflow pathway and a housing surfactant entrance fluidly connected to a housing surfactant pathway. The housing airflow pathway is configured to fluidly connect with both the inlet lumen and the outlet lumen. Similarly, the housing surfactant lumen can be configured to fluidly connect with the surfactant pathway. As discussed above, this can allow surfactant to flow from the surfactant pathway into the housing surfactant pathway without mixing with the inspiratory air from the inlet lumen.

In some embodiments, disclosed is an adaptor for medicament delivery comprising a tubular body, a housing, and a patient interface. In some embodiments the tubular body includes a first end and a second end, wherein the tubular body can include an inlet tube and an outlet tube. The inlet tube can include an inlet port at the first end and an outlet at the second end, wherein the inlet port is configured to be connected to an inspiratory conduit for receiving a flow of gases. The outlet tube can be adjacent to the inlet tube having an outlet port at the first end and an inlet at the second end, wherein the outlet port is configured to be connected to an expiratory conduit for dispensing the flow of gases. In some embodiments, the housing includes a first end and a second end, wherein the first end of the housing is attached to the second end of the tubular body. In some embodiments, the housing comprises a surfactant delivery tube wherein the surfactant delivery tube comprises an inlet port configured to connect to a source of medicament and a bifurcated outlet. The bifurcated outlet can be configured to deliver medicament to the nares of a patient. In some embodiments, the patient interface can be configured to be connected to the second end of the housing, wherein the patient interface is in fluid communication with an airway of a patient.

In other embodiments, the adaptor can include a housing that is permanently attached to the tubular body. In other embodiments, the adaptor includes a tubular body and housing comprising a rigid plastic. In other embodiments, the adaptor includes a flow of medicament comprising an aerosolized surfactant.

In other embodiments, the adaptor includes a patient interface comprising a pair of prongs. In some embodiments, the adaptor includes nasal prongs that are sized to fit the nares of the patient. In some embodiments, the adaptor includes a patient interface that is configured to interchangeably attach to a plurality of different nasal prong sizes. In some embodiments, the adaptor includes a patient interface that is press-fit onto the second end of the housing. In some embodiments, the adaptor comprises a patient interface that is removably connected to the second end of the housing.

In other embodiments, the adaptor comprises a tubular body that further comprises a pressure port connected to a pressure sensor, wherein the pressure sensor is configured to measure air pressure flowing through the pressure port. In other embodiments, the adaptor comprises a tubular body that further comprises a pressure tube connected to the housing. In other embodiments, the adaptor comprises a pressure port and an inlet port of the surfactant delivery tube that are on opposing sides of the adaptor. In other embodiments, the adaptor comprises a tubular body having an elongated oval cross-section.

In other embodiments, the adaptor comprises an inlet port having threading to connect to an inspiratory conduit, and an outlet port having threading to connect to an expiratory conduit. In some embodiments, the adaptor comprises an inlet port and an outlet port wherein a portion of the inlet port and the outlet port are tapered. In some embodiments, the adaptor comprises an inlet port and outlet port that are tapered to 15 mm or 22 mm.

In other embodiments, the adaptor can further comprise at least one clip connectable to an interface stabilization mechanism. In some embodiments, the adaptor includes an interface stabilization mechanism that comprises headgear.

In other embodiments, the adaptor comprises a retaining system comprising a two-part releasable attachment system comprising an interface patch and a dermal patch. In some embodiments, the adaptor comprises a two-part releasable attachment system that is foldable. In some embodiments, the adaptor comprises a two-part releasable attachment system that is configured to retain at least one of a surfactant tube, a pressure sensor line, and a feeding tube. In some embodiments, the adaptor comprises a two-part releasable attachment system that comprises a dynamic interface having a hinge configured to conform the dynamic interface to the shape of the face of the patient, and wherein the dynamic interface is configured to maintain the position of the prongs on the face of the patient by minimizing movement of the prongs.

In other embodiments, the adaptor further comprises a foam block configured to stabilize the adaptor on the face of the patient. In other embodiments, the adaptor is configured such that the bias air flow path through the adaptor occurs upstream from the flow of medicament.

In the above disclosed embodiments, the adaptor can include an integrated nozzle that is configured to connect with an external device to provide a fluid connection with the inside of the housing. In some examples, the nozzle can be disposed about another conduit to isolate and restrict the mixing of the aerosolized material (for example, a drug) with the air flow coming through the inlet tube. For example, the nozzle can be disposed about a surfactant tube. The surfactant tube can be configured to be fluidly connected to the respiratory assistance system to allow the delivery of a substance, such as an aerosolized surfactant, to the housing and to the patient through the patient interface. In some examples, the surfactant tube can have a bifurcated portion that allows the surfactant tube to be fluidly connected to both nostril lumens of the nasal prongs so as to allow medicament to be delivered through both nostrils of the patient.

BRIEF DESCRIPTION OF THE DRAWINGS

These and other features, aspects and advantages of the present disclosure will be described with reference to the following drawings, which are illustrative but should not be limiting of the present disclosure.

FIG. 1 illustrates an example respiratory system.

FIGS. 2A-2F illustrate a plurality of views of an adaptor for a respiratory system according to an embodiment of the disclosure.

FIG. 2G illustrates an enlarged view of an embodiment of the surfactant tube that can be found in the adaptor of FIGS. 2A-2F that guide air flow into the nostril lumens of the patient interface and into the patient.

FIGS. 3A-3H illustrate a plurality of views of an adaptor for a respiratory system according to another embodiment of the disclosure.

FIGS. 4A-4G illustrate a plurality of views of an adaptor for a respiratory system according to another embodiment of the disclosure.

FIGS. 5A-5G illustrate a plurality of views of an adaptor for a respiratory system according to another embodiment of the disclosure.

FIGS. 6A-6I illustrate a plurality of views of an adaptor for a respiratory system according to another embodiment of the disclosure.

FIGS. 7A-7G illustrate a plurality of views of an adaptor for a respiratory system according to another embodiment of the disclosure.

FIGS. 8A-8F illustrate a plurality of views of an adaptor for a respiratory system according to another embodiment of the disclosure.

FIGS. 9A-9E illustrate a plurality of views of the housing of the respiratory system of FIGS. 8A-8F.

FIGS. 10A-10C illustrate a plurality of views of a housing of an adaptor for a respiratory system according to another embodiment of the disclosure.

FIGS. 11A-11C illustrate a plurality of views of a housing of an adaptor for a respiratory system according to another embodiment of the disclosure.

FIGS. 12A-12D illustrate a plurality of views of a housing of an adaptor for a respiratory system according to another embodiment of the disclosure.

FIGS. 13A-13B illustrate an embodiment of a removable attachment for an interface stabilising mechanism.

FIGS. 14A-14D illustrate an embodiment of an attachment mechanism for securing a user interface and/or user interface tubing to a patient.

FIGS. 15A-15C illustrate an embodiment of an attachment mechanism comprising a dynamic interface.

FIGS. 16A-16C illustrate another embodiment of the attachment mechanism comprising a dynamic interface.

FIG. 17 illustrates another embodiment of the attachment mechanism comprising a dynamic interface.

FIG. 18 illustrates an embodiment of a securement system comprising a two-part releasable attachment or connection arrangement.

FIG. 19 illustrates another embodiment of the securement system comprising a two-part releasable attachment or connection arrangement.

FIG. 20 illustrates another embodiment of the securement system comprising a two-part releasable attachment or connection arrangement.

FIGS. 21A-21B illustrate an embodiment of a fixation structure configured to secure the pressure lumen and/or surfactant lumen to the face of the patient.

DETAILED DESCRIPTION

FIG. 1 illustrates an example of a respiratory assistance system 1 configured to provide respiratory gases to a patient. In the illustrated embodiment, the patient is an infant; however the patient could also be an adult or a child. The respiratory assistance system 1 can include a gases source 2 that supplies gases to a humidification apparatus 3. The humidification apparatus 3 can condition the gases before passing them via an inspiratory tube 6 to a patient by a patient interface 5. In some examples, the patient interface 5 can be nasal prongs or a nasal mask. In some embodiments, the patient interface 5 may be configured to be sealingly positioned on the face of the patient. Upon exhalation of the patient, the gases are passed through an expiratory tube 4 to a pressure regulating device 7. In some embodiments, the pressure regulating device 7 is a ventilator or bubbler. The patient interface 5 couples to the inspiratory tube 6 and to the expiratory tube 4 using an adaptor 100. Alternative respiratory assistance systems can include a single tube, for example inspiratory tube 6, which can allow exhalation to occur through the patient interface 5 and/or the adaptor 100. Thus, the adaptor 100 can couple the patient interface 5 to the single tube system.

Prior art adaptors configured to deliver aerosols to a patient are bulky and heavy in use and may cause discomfort to the patient. As a result, such adaptors are often only temporarily coupled to the patient during aerosol treatment. This results in high user effort to install and then to remove these adaptors, which can impact the treatment delivered to the patient. Other prior art adaptors provide poor sealing mechanisms between the adaptor and the coupling region of a medicament delivery device, which causes significant pressure losses in the system.

FIGS. 2A-2F, 3A-3H, 4A-4G, 5A-5G, 6A-6I, and 7A-7G illustrate example embodiments of adaptors that address many of the disadvantages of existing adaptors. The disclosed adaptors can include features that allow it to remain in place during the use of the medical system. Thus, the adaptor may not require removal following aerosol treatment of the patient. For example, the adaptor can form an integral part of the patient interface 5. This can include, for example, a continuous positive airway pressure (CPAP) interface and/or may include features that enable delivery of medicament via the integrated adaptor.

In the aforementioned embodiments the adaptor can include a housing that is fluidly connected to a plurality of conduits to provide fluid flow, such as air, and the delivery of aerosolized surfactants to the patient through the patient interface. In addition to the housing, the adaptor can include an inlet port, an outlet port, a surfactant port, and a coupling surface for engaging a patient interface. In some embodiments, the adaptor can also include a pressure tube with a pressure port and a pressure lumen that is fluidly connected to the housing.

In some embodiments, the adaptor can include an integrated nozzle that is configured to connect with an external device to provide a fluid connection with the inside of the housing. In some examples, the nozzle can be disposed about another conduit to isolate and restrict the mixing of the aerosolized material (for example, a drug) with the air flow coming through the inlet tube. For example, the nozzle can be disposed about a surfactant tube. The surfactant tube can be configured to be fluidly connected to the respiratory assistance system to allow the delivery of a substance, such as an aerosolized surfactant, to the housing and to the patient through the patient interface. In some examples, the surfactant tube can have a bifurcated portion that allows the surfactant tube to be fluidly connected to both nostril lumens of the nasal prongs so as to allow medicament to be delivered through both nostrils of the patient.

As will be discussed in more detail below, in the embodiments illustrated in FIGS. 2A-2F, 3A-3H, 4A-4G, 5A-5G, 6A-6I, and 7A-7G, the body of the adaptor can be divided into a plurality of compartments. The plurality of compartments within the adaptor can reduce premixing of the medicament received through the surfactant port and the inspiratory gases through the inlet lumen and reduce dilution of the drug by the outgoing gases through the outlet port. In some examples, the arrangement of the conduits within the adaptor can help to maximize gas flow to the patient. For example, inspiratory gases can enter the adaptor through the inlet port and flow through the inlet lumen and into the housing. There, the gases can mix with the medicament delivered from the bifurcated portion surfactant tube near the opening of the nostril lumens. The expiratory gases can then exit the patient interface and move around the surfactant tube, flow through the outlet lumen, and exit the adaptor from the outlet port.

FIGS. 8A-8F, 9A-9E, 10A-10C, 11A-11C, and 12A-12D illustrate another embodiment of adaptors that also address many of the disadvantages of existing adaptors. As with the adaptors illustrated in FIGS. 2A-2F, 3A-3H, 4A-4G, 5A-5G, 6A-6I, and 7A-7G, the adaptors in FIGS. 8A-8F, 9A-9E, 10A-10C, 11A-11C, and 12A-12D similarly can include features that allow it to remain in place during the use of the medical system. Thus, the adaptor may not require removal following aerosol treatment of the patient. For example, the adaptor can form an integral part of the patient interface 5. This can include, for example, a continuous positive airway pressure (CPAP) interface and/or may include features that enable delivery of medicament via the integrated adaptor.

In the aforementioned embodiments, the adaptors are similar to the adaptors disclosed in FIGS. 2A-2F, 3A-3H, 4A-4G, 5A-5G, 6A-6I, and 7A-7G. In some examples, the adaptors can include a housing that is fluidly connected to a plurality of conduits to provide fluid flow, such as air, and the delivery of aerosolized surfactants to the patient through the patient interface. In addition to the housing, the adaptor can include an inlet port, an outlet port, a surfactant port, and a coupling surface for engaging a patient interface. In some embodiments, the adaptor can also include a pressure tube with a pressure port and a pressure lumen that is fluidly connected to the housing.

The adaptors illustrated in FIGS. 8A-8F, 9A-9E, 10A-10C, 11A-11C, and 12A-12D can have a housing that is configured to keep the surfactant flow path out of the bias flow path such that the inlet lumen and outlet lumen are fluidly connected before surfactant is delivered to the air flow path. Delivering surfactant to the air flow path after the exchange or in parallel to the bias flow of air from the inlet lumen and the outlet lumen ensures less dilution of the surfactant to the infant as well as reducing the deposition of the surfactant on the interior of the adaptor.

In some examples, the inside of the housing can include a divider that divides the housing to provide a housing airflow entrance fluidly connected to a housing airflow pathway and a housing surfactant entrance fluidly connected to a housing surfactant pathway. The housing airflow pathway is configured to fluidly connect with both the inlet lumen and the outlet lumen. Similarly, the housing surfactant lumen can be configured to fluidly connect with the surfactant pathway. As discussed above, this can allow surfactant to flow from the surfactant pathway into the housing surfactant pathway without mixing with the inspiratory air from the inlet lumen.

The divider can provide two separate compartments for the inspiratory/expiratory airflow and the surfactant flow. The housing, near the housing exit, includes an undivided portion that allows the inspiratory air from the inlet lumen to mix with the surfactant from the surfactant lumen before being delivered to the patient. The divider goes through a turn section but the turn portion includes rounded edges to reduce aerosolized surfactant deposition at the turn. The housing airflow pathway provides inspiratory airflow into the undivided portion to allow mixing of inspiratory airflow and aerosolized surfactant.

Existing respiratory assistance systems 1 require a user to remove the patient interface temporarily to replace it with a medicament delivery interface, following which the patient interface is restored to the patient. This configuration may cause patient discomfort and may reduce the efficacy of the treatment. As a result, a patient may be more likely to undergo invasive procedures, due to disturbances during treatment.

In some examples, the adaptor can be integrated with the patient interface 5. Integration of the adaptor and the patient interface can reduce the number of steps a user is expected to perform to install and remove the adaptor, improving the usability of the system. Use of the adaptor throughout the treatment duration can reduce the likelihood of complications during treatment, and reduces the number of disturbances during the treatment.

In some examples, the adaptor can have an optimised construction that allows it to maintain a small footprint which can increase patient comfort. In some examples, the small footprint of the adaptor can allow the adaptor to provide aerosolized therapy while still retaining the size and weight of a normal CPAP interface. This interface can allow the adaptor to have similar usability as other CPAP interfaces.

In some examples, the adaptor is configured such that it is not bulky or heavy for the patient, and thus may be perceived to be less obstructive. To increase patient comfort, the size of the adaptor can be reduced to limit the amount the adaptor covers/blocks the patient's face from view In other examples, patient comfort can be increased by reducing the weight of the adaptor 100. For example, the adaptor and patient interface 5 can be configured such that it does not weigh more than any baby for whom the device could be configured for use (e.g. preterm baby). In some examples, the weight of the adaptor and patient interface 5 can weigh approximately 100-500 grams. In other examples, the adaptor and patient interface 5 can weigh less than 100 grams or more than 500 grams. In other examples, the adaptor and patient interface 5 can weigh between 15-30 grams. In other examples, the adaptor and interface 150 can weigh 15 grams, 16 grams, 17 grams, 18 grams, 19 grams, 20 grams, 21 grams, 22 grams, 23 grams, 24 grams, 25 grams, 26 grams, 27 grams, 28 grams, 29 grams, or 30 grams.

Use of an integrated system to deliver gases to a patient can improve usability and reduce patient discomfort. For example, the adaptor can be designed to deliver sufficient gases to the patient in normal use. Thus, the adaptor can remain in place during the ventilation of the patient. Although the present disclosure describes an adaptor for use with a respiratory system, embodiments of the adaptor may be used with other medical systems, for example, a surgical system such as for laparoscopic or open surgery.

Figure 2B:
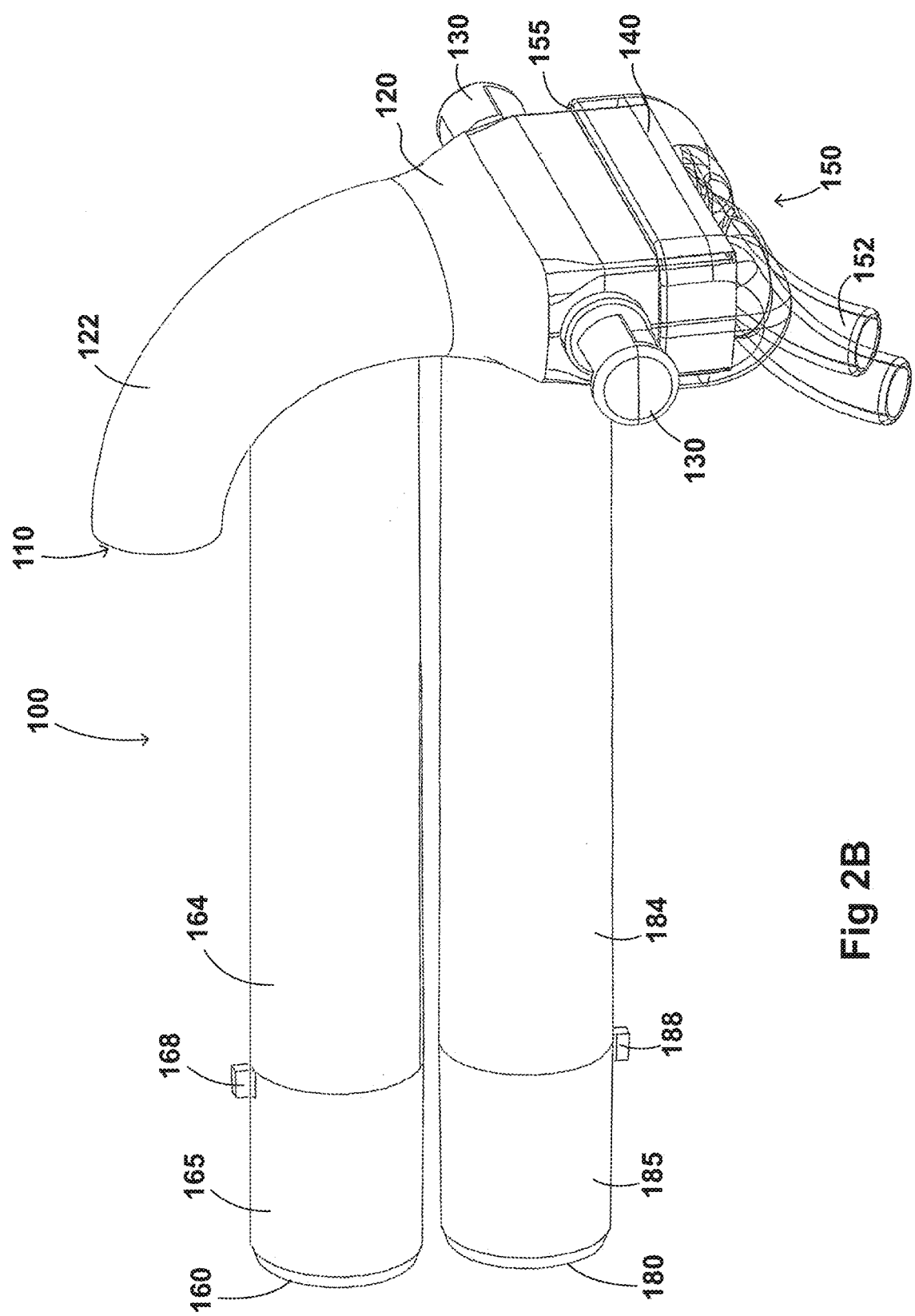
Figure 2C:
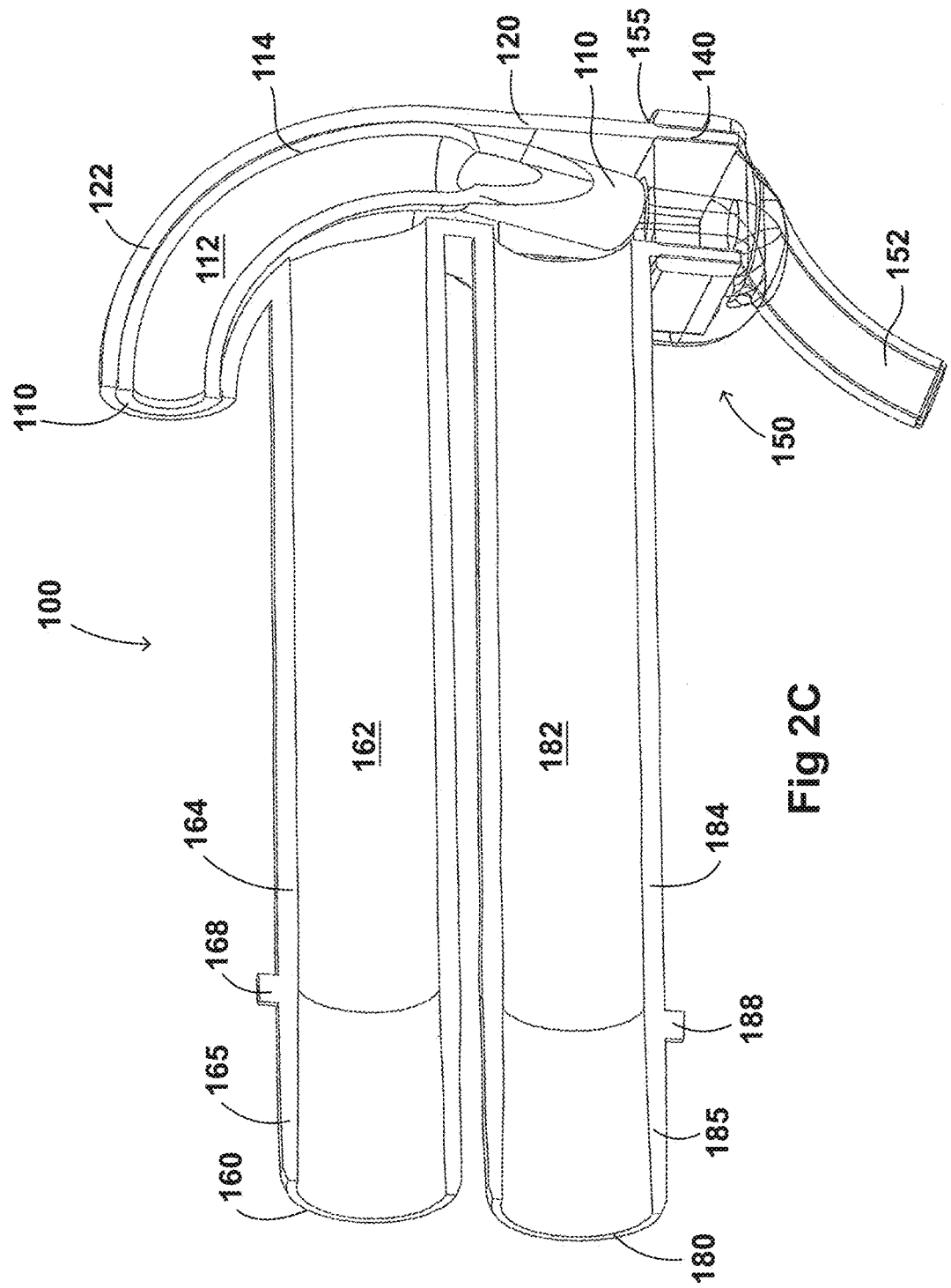
Figure 2D:
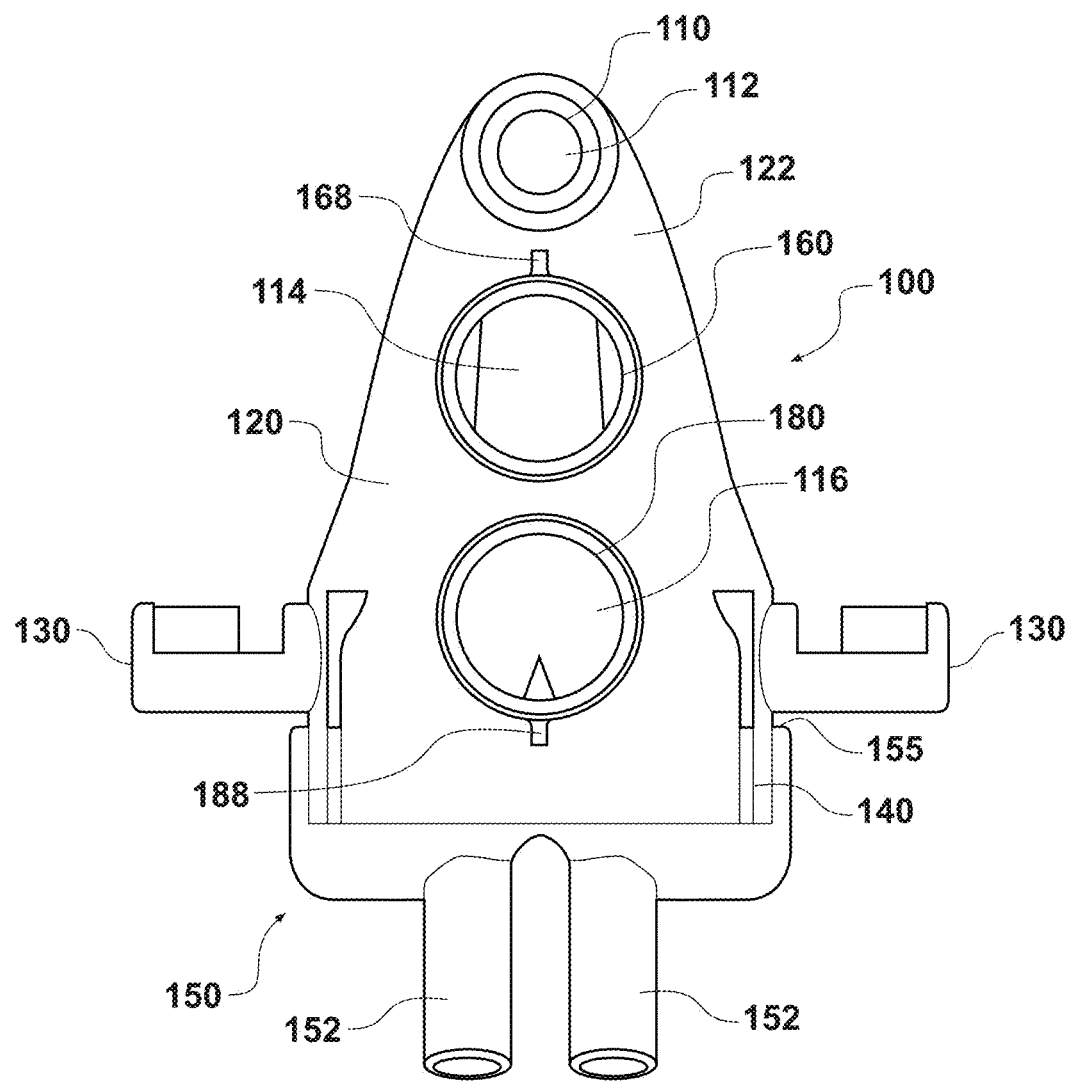
Figure 2E:
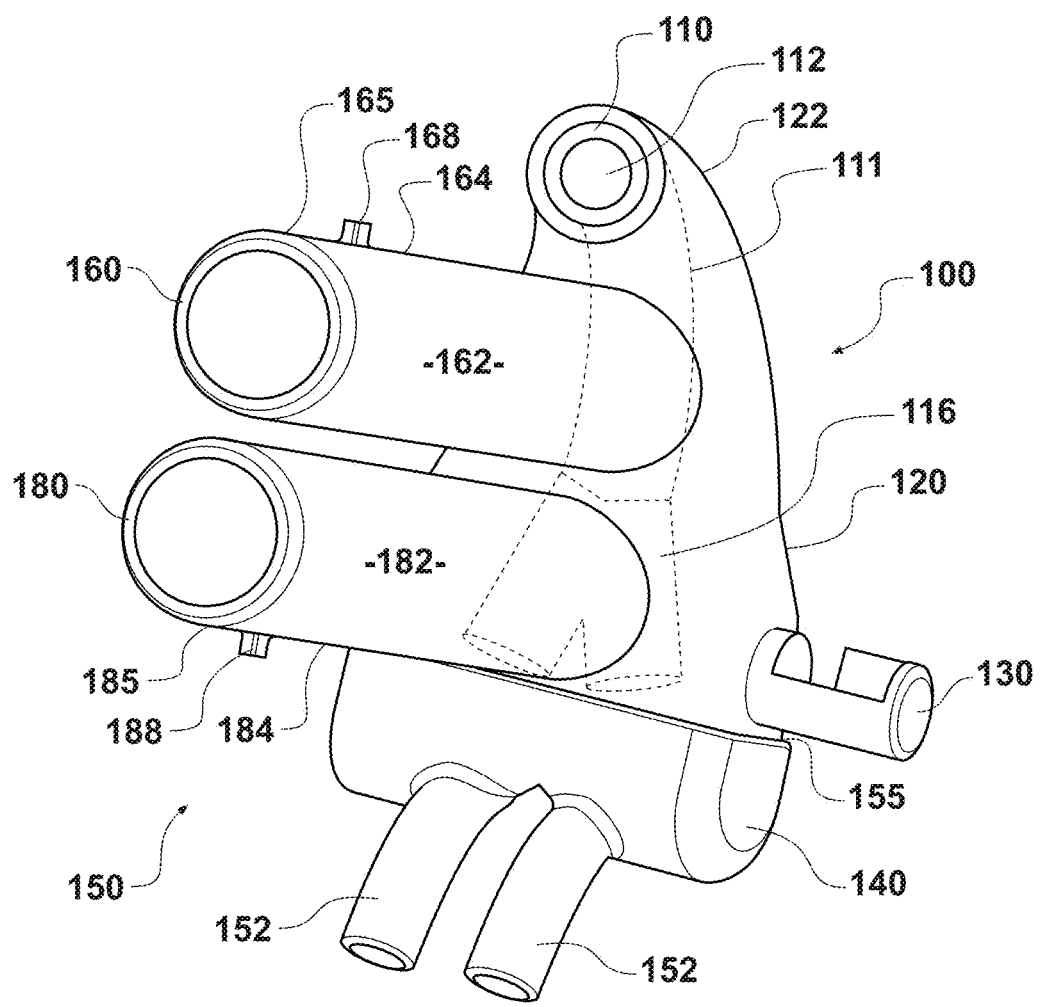

Turning first to FIGS. 2A and 2B, illustrated is an embodiment of the adaptor 100. The adaptor 100 can include a housing 120 that is fluidly connected to a plurality of conduits to provide fluid flow, such as air, and the delivery of aerosolized surfactants to the patient through the patient interface 150. The adaptor 100 can include a housing 120, a plurality of clips 130, an inlet port 160, an outlet port 180, a surfactant port 110, and a coupling surface 140 for engaging a patient interface 150.

In some examples, the housing 120 can include a substantially hollow cylindrical body. The shape of the housing 120 can be optimised to reduce resistance to flow within the housing 120. In some examples, the housing 120 can comprise different shapes, for example, rectangular, square, hexagonal, or semi-circular. In some embodiments, the shape of the housing 120 can minimize volume within the housing 120. This can reduce dead space—therefore reducing the build-up of carbon dioxide within the housing 120. The housing 120 can be compact so as to reduce the weight and bulk of the housing 120 and improve patient comfort. As mentioned above, and discussed in more detail below, the housing 120 can be configured to both receive gases through an inspiratory tube and aid the exit of gases through an expiratory tube.

The housing 120 can include a coupling surface 140 at an end of the housing 120 that is proximate to the patient. As illustrated in FIGS. 2A-2B, the coupling surface 140 can be rectangular in cross-section. The coupling surface 140 can include a first end that is fluidly connected with the housing 120 and a second end that is configured to couple with the patient interface 150. The second end of the coupling surface 140 can allow fluid communication between the housing 120 and the patient interface 150. In some embodiments, a partial barrier can exist between the housing 120 and the first end of the coupling surface 140. An orifice can thus maintain fluid communication between the housing 120 and the patient interface 150. The orifice can direct the flow of gases toward the patient interface 150. In some examples, the orifice can control the pressure of the gas flow as it enters the patient interface 150.

In some embodiments, the patient interface 150 can be configured to removably couple with the coupling surface 140. In some examples, the patient interface 150 can be coupled with the coupling surface 140 using adhesives or mechanical mechanisms such as snap-fit mechanisms. In some embodiments, the patient interface 150 can be permanently attached to the coupling surface 140 using adhesives, snap-fit mechanisms, or welding techniques. In some embodiments, the coupling between the patient interface 150 and the coupling surface 140 can have a friction fit. FIGS. 2A-2F illustrate a patient interface 150 that is transparent so as to allow the engagement between the coupling surface 140 and the patient interface 150 to be visualized. The patient interface 150 can include a substantially hollow complementary region 155 that is configured to receive the coupling surface 140. As will be described in more detail below, an embodiment of the complementary region of the patient interface can be visualized in FIG. 2G. In some embodiments, the coupling surface 140 can be configured to receive the complementary region 155 of the patient interface 150. In some embodiments, the patient interface 150 can be permanently coupled with the adaptor 100. This can provide a fully integrated adaptor, which may improve the usability of the adaptor 100.

As illustrated in FIGS. 2A-2B, in some examples, the patient interface 150 can include nasal prongs 152. In some embodiments, the patient interface 150 can include respiratory interfaces such as, but not limited to, a nasal mask, oral mask, combined nasal and oral mask, tracheal mask, or nasal pillows. In some embodiments, the adaptor 100 can be adapted for use in a surgical application. The patient interface 150 can include a diffuser, trocar, or catheter.

In some embodiments, the adaptor 100 can include a retention system, which may comprise clips 130 that are positioned on first and second sides of the housing 120. As illustrated in FIGS. 2A-2B, the first and second sides of the coupling surface 140 can be substantially perpendicular to the first and second ends of the coupling surface 140. In some embodiments, the clips 130 can be configured to be mobile clips. For example, the clip 130 can be positioned on a slidable and/or rotatable bar or cord. In this way, the position of the clips 130 can be rotated or altered to simplify the attachment of the patient stabilising mechanism to the adaptor 100. In some embodiments, the clips 130 can be configured to permanently attach to an interface stabilising mechanism.

Figure 7B:
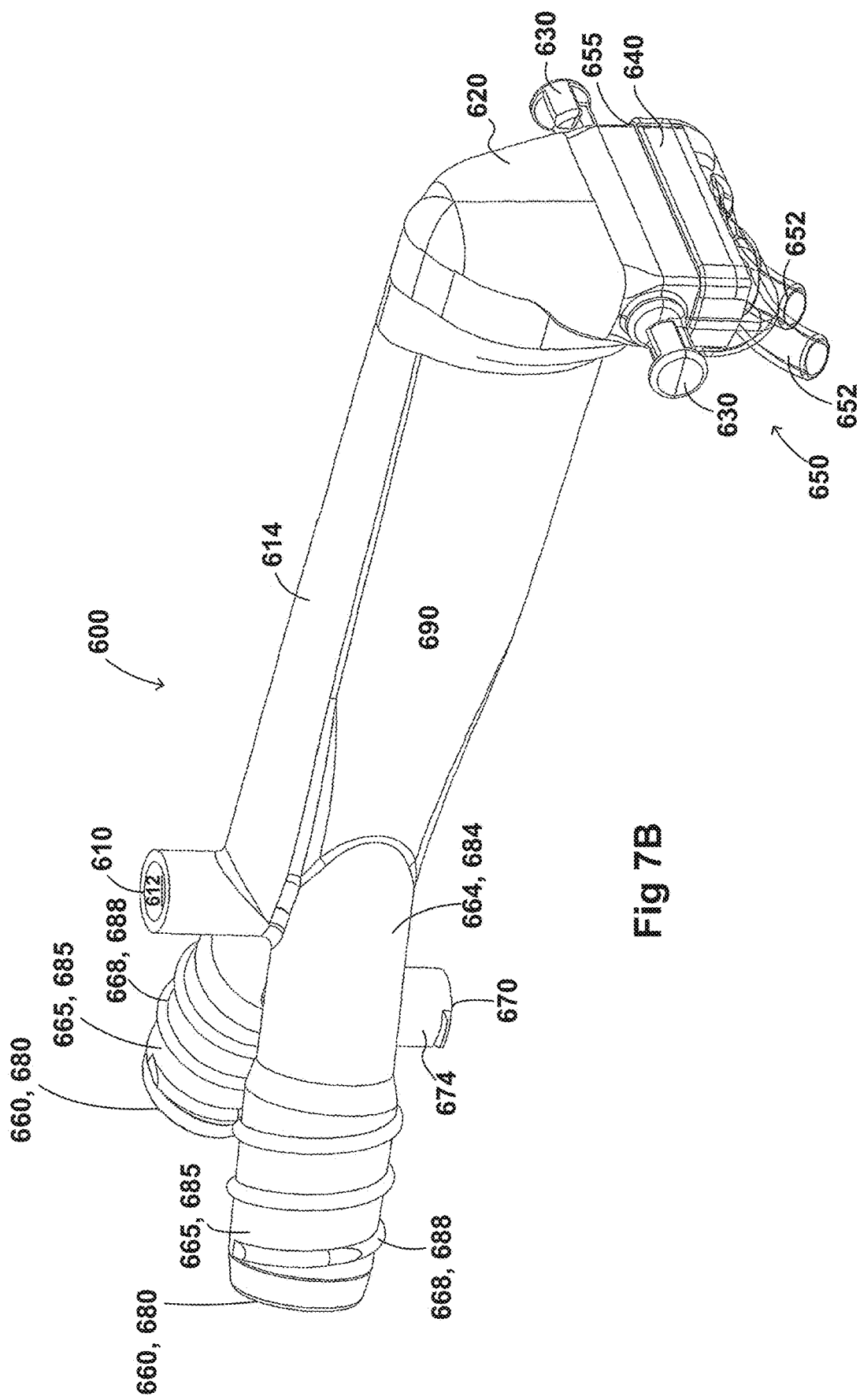
Figure 7C:
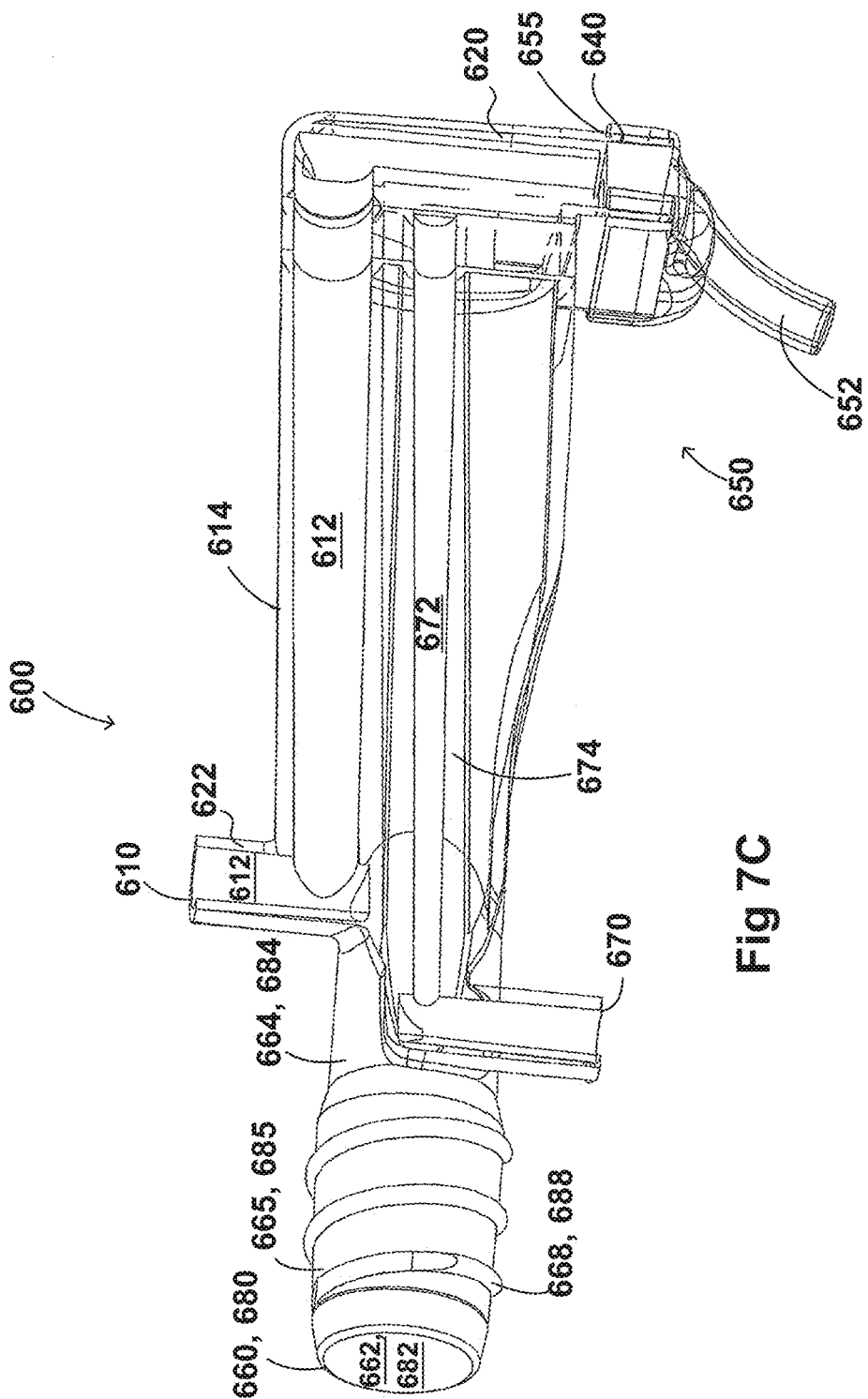
Figure 7D:
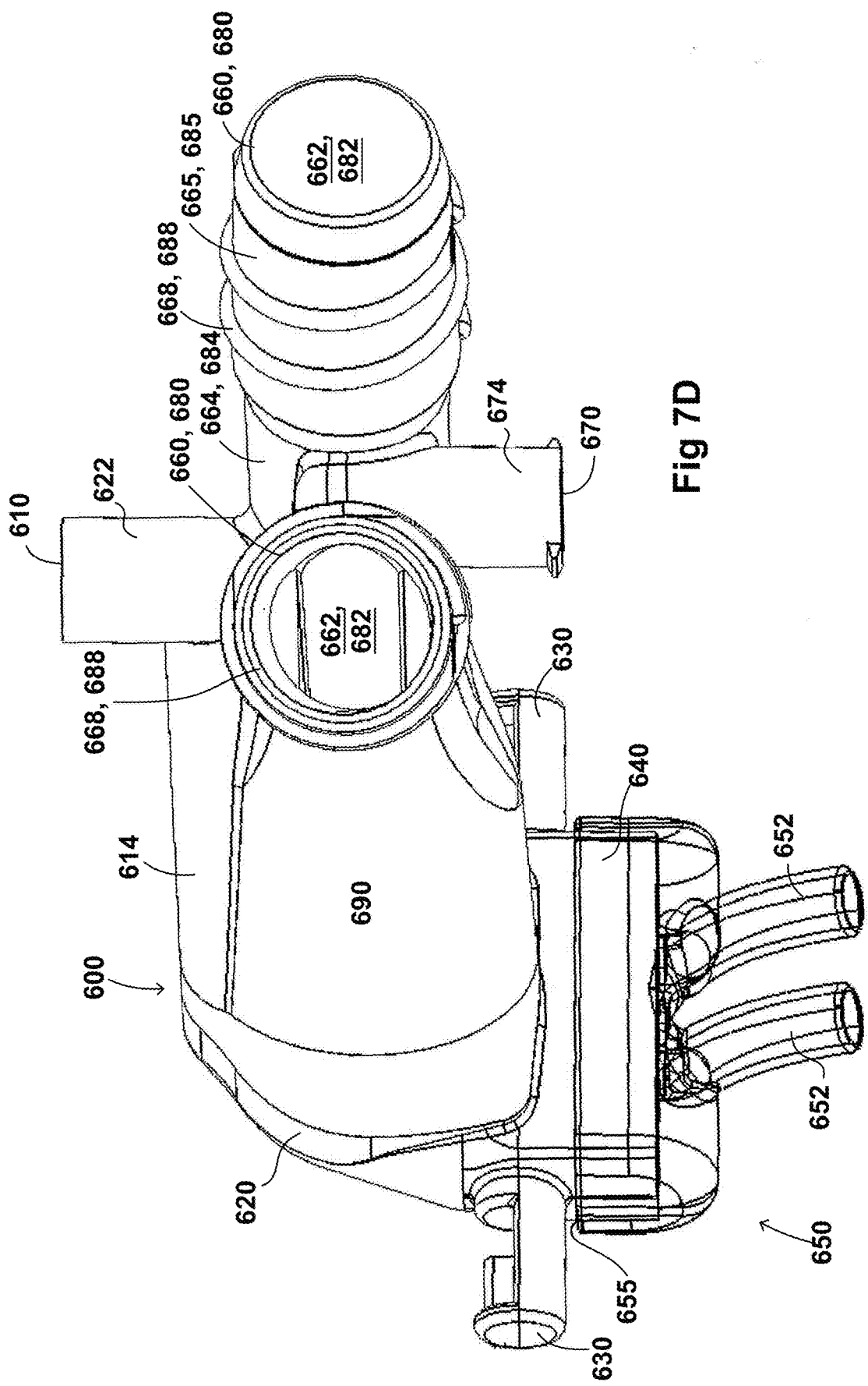
Figure 7E:
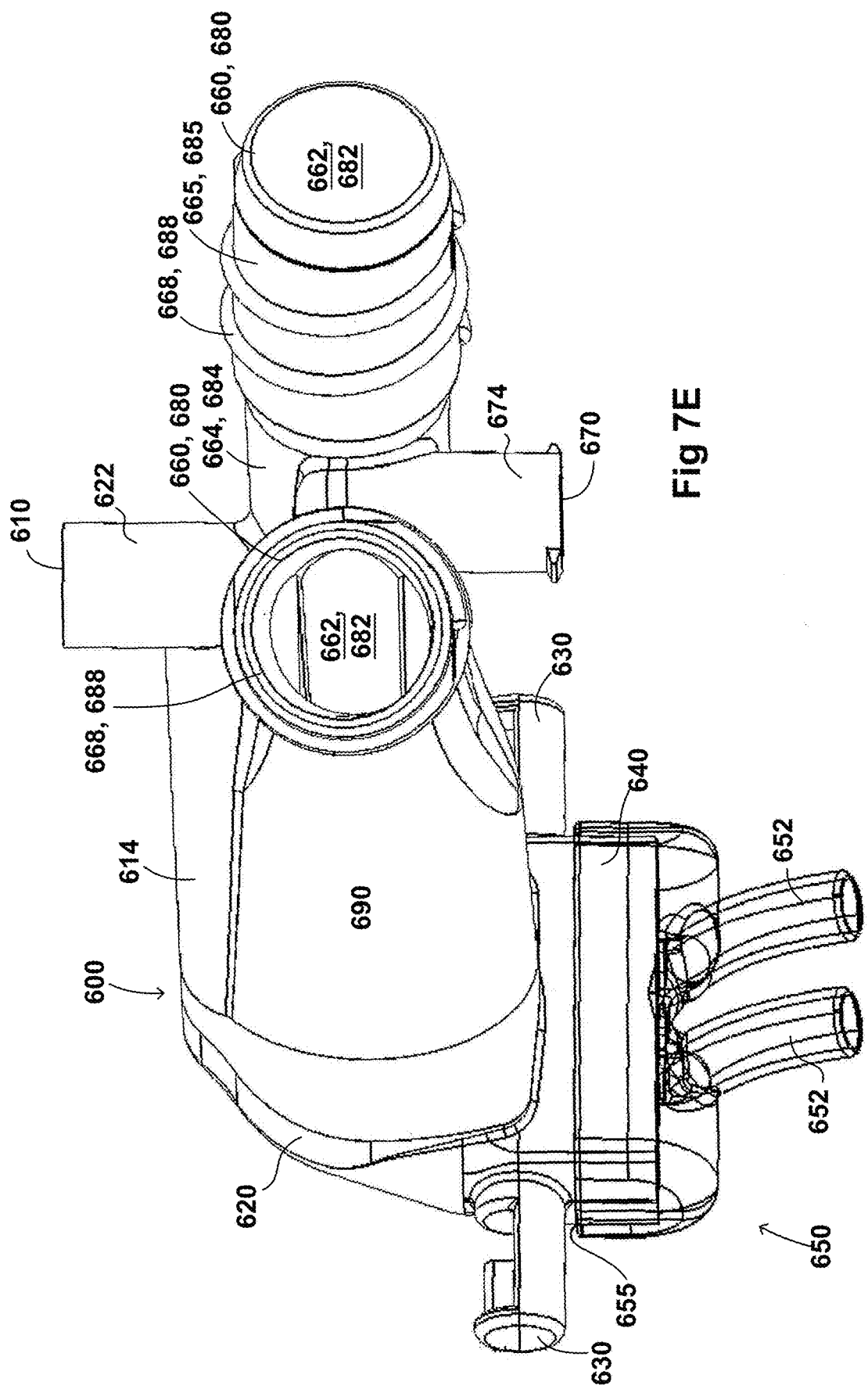
Figure 7F:
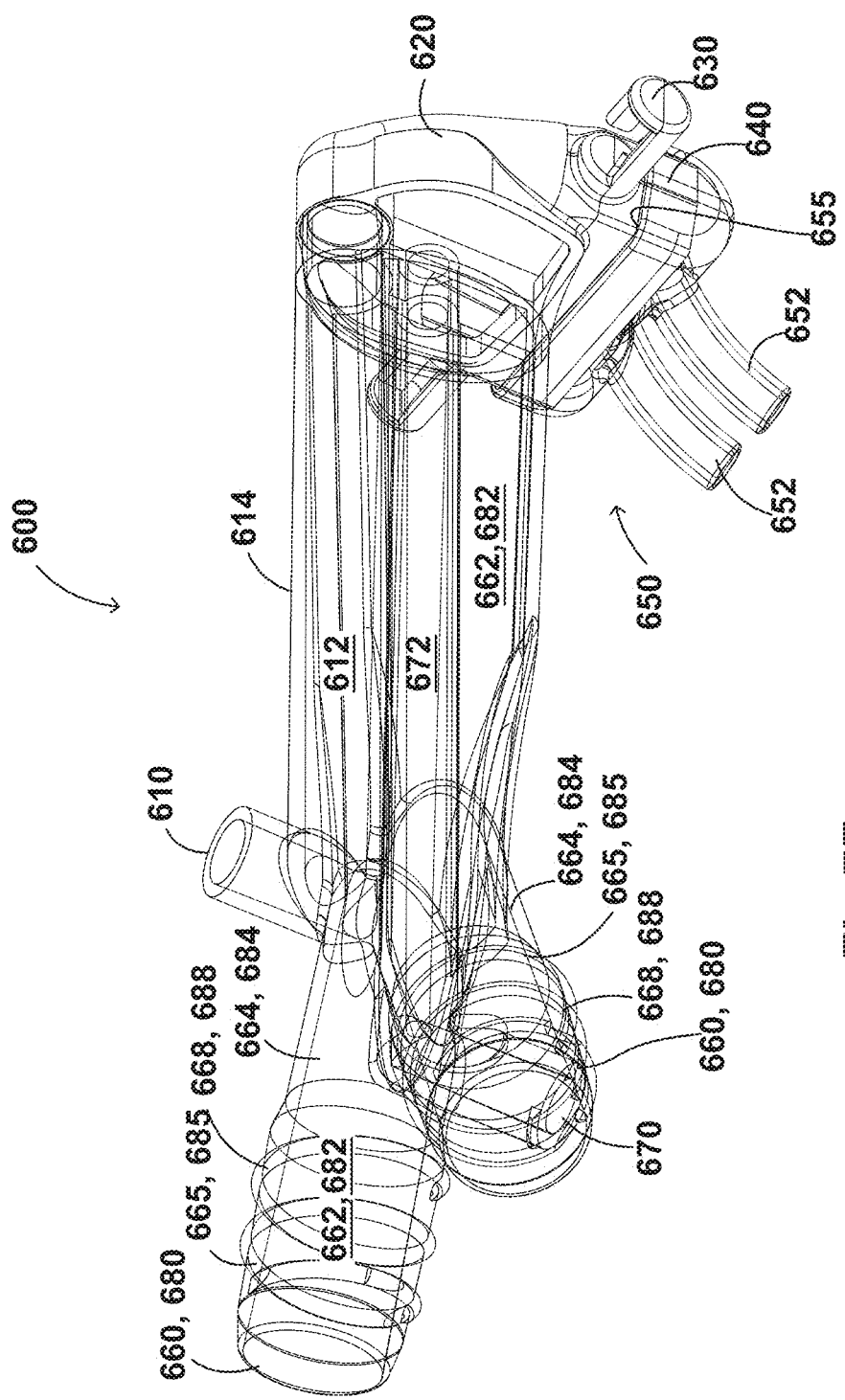
Figure 7G:
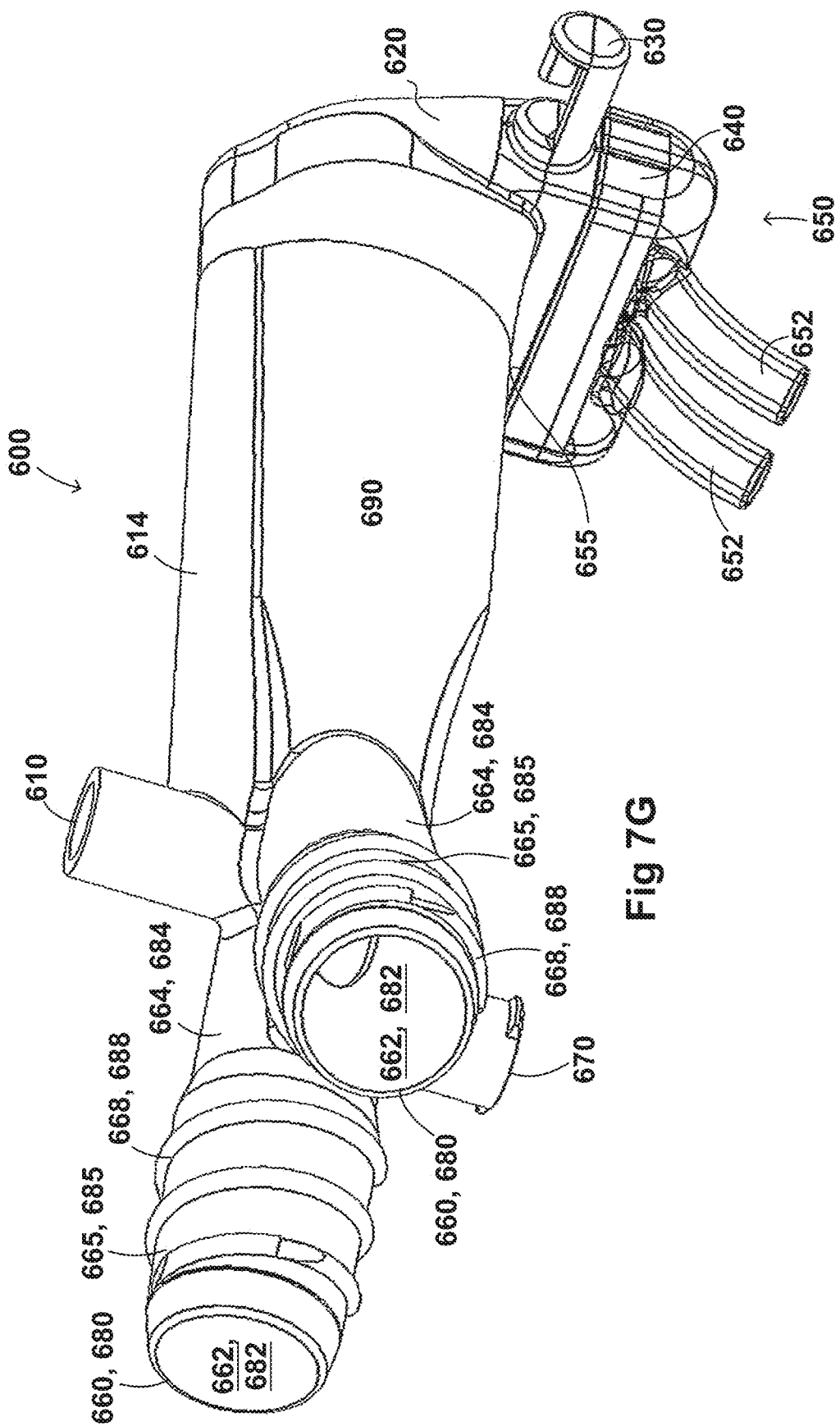

In some examples, the clips 130 can engage a removable attachment that is attached to an interface stabilising mechanism, such as headgear or a hat or bonnet. In some examples, the removable attachment is a loop. In some embodiments, the removable attachment is a clipping mechanism. An example of the removable attachment is illustrated in FIGS. 13A and 13B. As illustrated in FIG. 13A, the clip 130 can hook onto a loop of the removable attachment. The removable attachment can be looped onto a length of fabric that is attached to a portion of the interface stabilising mechanism. FIG. 7B illustrates the removable attachment of the interface stabilising mechanism.

In some embodiments, as illustrated in FIGS. 13A-13B, the clips 130 can comprise C-shaped protrusions. In some embodiments, the clips 130 can be L-shaped protrusions, clipping mechanisms, adhesives, or a hook and loop mechanism. The clips 130 can be configured to attach to the interface stabilising mechanism in a simple yet effective mechanism. This can enable the patient interface 150 to be positioned correctly and stably on the patient.

In some embodiments, the retention system can be a two-part releasable attachment mechanism. Several such two-part releasable attachment mechanisms are described in the Applicants' U.S. application Ser. No. 13/880,036, filed on Oct. 18, 2011 and PCT App. No. PCT/NZ2016/050041, filed on Mar. 16, 2016 each hereby incorporated by reference.

Figure 14A:
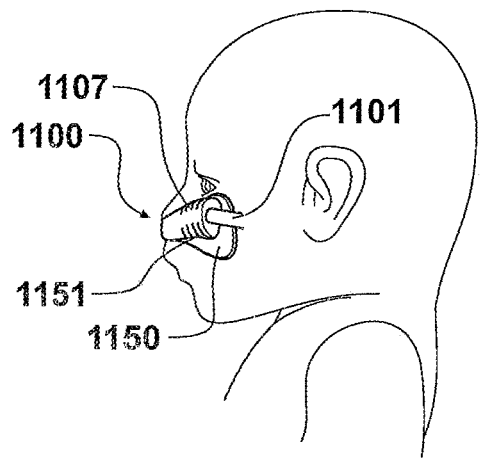

An example of the attachment mechanism of Applicant's U.S. application Ser. No. 13/880,036 is hereby reproduced as FIGS. 14A-14D. The attachment mechanism can be configured for securing a user interface and/or user interface tubing to a patient as illustrated in FIG. 14A. The attachment mechanism 1100 is illustrated supporting a nasal cannula on an infant's face, but can be adapted to support the disclosed adaptor of the present application using the same principles, such as by including an extension portion attachable to a patch instead of clips 130.

In some embodiments, the attachment mechanism provides for a generally more rapid and improved or simplified ease of installation of a user interface into an operational position on a user. Further, these benefits may also contribute to improved or simplified ease of application of alternative user interfaces or removal of a user interface from a user when cycling a user between different therapies (such as gas treatments, e.g. CPAP or high-flow applications). In various embodiments provided by the attachment mechanism, such an attachment mechanism may provide for quick location of an interface to a user, and may provide for the secured positioning of the interface.

In some embodiments, the ease with which a user interface may be positioned for a user is particularly useful. Providing a system whereby a carer (e.g. nurse) is able to apply the securement system with a single hand, particularly where the interface user is an infant, can be particularly advantageous.

Figure 14B:
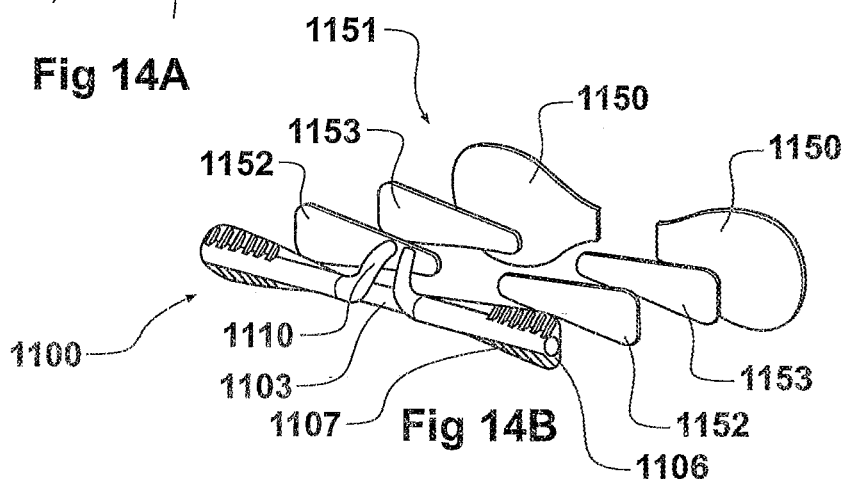

In addition, in another embodiment, the attachment mechanism provides for a first level of securement of a user interface to a user. For example, such a first level of securement may be that as shown by FIGS. 14A-14B. Where a user requires additional or heightened security of user interface positioning or securement, a secondary level of interface securement can be utilized. Such an additional level may include application of an over patch, such as that provided, for example, by patch 1260 illustrated in FIGS. 14D-14E. Such a patch 1260 may be an adhesive patch and can be installed over the top of the user interface and/or tubing and adhered to a portion of the dermal patch 1150 (FIG. 14B).

The attachment mechanism 1100 comprises a two-part releasable attachment or connection arrangement 1151. The releasable connection arrangement 1151 acts between a pair of patches that are affixed to the patient and the user interface respectively.

The first patch can be a dermal patch 1150 that is adhered or otherwise attached to the patient's skin. The dermal patch can have a user side that faces the user's skin and an interface side that faces the user interface. The user side of the dermal patch 1150 may be attached to the skin of a user by a dermatologically sensitive adhesive, such as a hydrocolloid. The user interface side of the dermal patch can be provided with the first part 1153 of the two-part releasable attachment or connection system 1151.

The second patch can be a user interface patch 1152. The user interface patch 1152 can also have a patient side and an interface side. The patient side of the user interface patch 1152 can be disposed adjacent the dermal patch when the attachment mechanism 1100 is engaged. The complimentary second part of the two-part releasable attachment or connection system 1153 can be affixed to the patient side of the user interface patch 1152, so that the respective parts of the two-part releasable attachment or connection system 1151 are easily engagable when the patches 1150, 1152 are brought together. The interface side of the user interface patch 1152 can be affixed to the user interface. The user interface patch may be integrated with or suitably adhered to the user interface.

In some examples, a part or corner of the user interface patch 1152 may include a region that does not attach to the dermal patch 1150. The general purpose of this can be to allow a region (or tab) that can be more easily gripped by a user or carer for removing or detaching the interface from the dermal patch.

The two-part releasable attachment or connection arrangement 1151 may comprise a hook and loop material (such as Velcro™), a magnet or an array of magnets disposed on the respective patches with the poles suitably arranged, an adhesive arrangement that is activated when the patches are urged together or another suitable releasable suitable coupling. The interface side of the dermal patch 1150 may have one of a hook or a loop material, and the patient side of the user interface patch 1152 may have the other of the hook or loop material, such that the dermal and user interface patches are releasably attachable or connectable to each other.

When a hook and loop material is referenced, a hook and loop material can mean any one of a wide variety of area type mechanical fasteners. For example, the Velcro™ product range can include hook and loop product where the hook component includes upstanding nylon hooks (formed as cut loops through a woven backing web) which engage with any complimentary loop pile material. The Velcro™ range can also include extruded hook products, typically of a smaller size and which mate with "fluffy" non-woven fiber backing materials. These hook materials are designed to work with a range of loop substrates and in some cases, these hook materials act as loop substrates as well. Other similar systems include the Dual-Lock™ reclosable fastener system from 3M of St Paul, Minn. USA. The common feature of these releasable fastening systems is that they engage at any part of the contact between the two parts of the system. Precise alignment of individual connectors is not required because a multitude of connectors are distributed across the area of the product. A wide range of releasable fastener systems within this field may be used in the releasable attachment mechanism for providing releasable attachment between the dermal patch and the user interface.

The first part of the two-part releasable attachment or connection system may be adhered to the user interface side of the dermal patch with a suitable adhesive and occupy up to 100% or less than about 90%, or about 85%, or about 75%, or about 60% or about 50% or about 40% or about 30% or about 20% or about 10% of the interface side surface area of the dermal patch. In some embodiments, the dermal patch 1150 is a generally planar pad having a thickness much less than both its width and its length. In some embodiments, the pad has an overall oval shape, but may take other shapes.

The pad can also include a first part 1153 of the two-part releasable attachment mechanism 1151. In some embodiments, the construction of the dermal patch is such that the first part 553 of the releasable attachment mechanism comprises a substrate and multitude of fastener elements (with effective hooks, effective loops or other elements) provided across the area of the substrate. The substrate is secured to the body of the dermal patch. In some embodiments, the substrate is secured by adhesive or by direct bonding during forming of the dermal patch.

In some embodiments, the substrate can be smaller in area than the dermal patch and is located on the dermal patch so that it does not reach any edge of the dermal patch. In this way, the edge of the substrate can be spread from the edge of the dermal patch all around the perimeter of the substrate.

In some embodiments, the substrate for the first part of the two-part releasable attachment system can be flexible such that the plane of the substrate may bend to follow a surface that is curved in one direction. However, the substrate is typically not also stretchable to be able to follow a surface curved in two orthogonal directions. However, the pad is of the dermal patch may be stretchable and conformable to surfaces curved in more than one direction such as may be required to conform to the contours of the location of placement on the patient. According to some embodiments, this difficulty is alleviated by providing a first part 1153 of the two-part releasable mechanism in a form wherein the portion of substrate is divided by at least one slit or at least one slot into regions such that that different parts of the substrate portion may bend independently and thus the overall form of the substrate portion may deform to substantially match a surface curved in two directions. This will be the case even though the substrate portion is only curved in one direction at any individual location on the substrate portion.

Figure 14C:
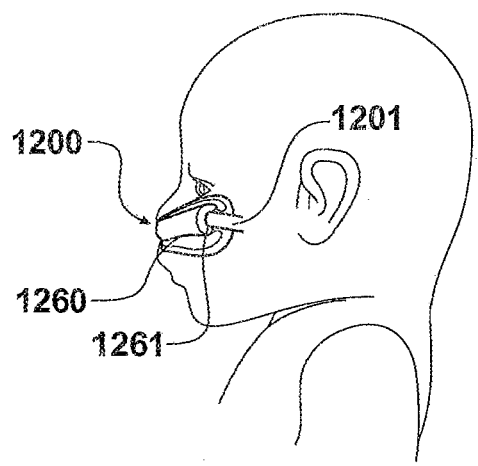
Figure 14D:
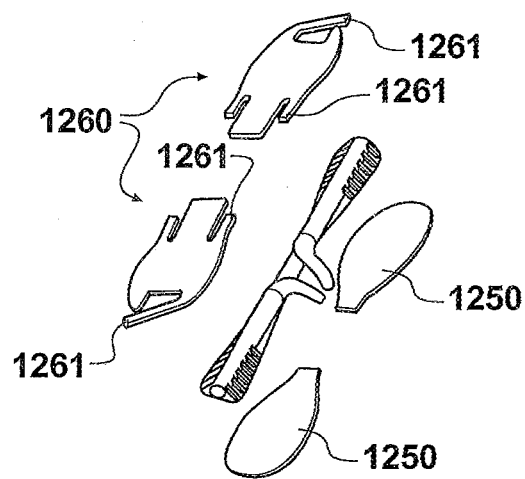

Another embodiment of the attachment mechanism is illustrated in FIGS. 14C-14D. The attachment mechanism 1200 can comprise a dermal patch 1250 and a securing patch 1260. The securing patch 1260 can extend over the user interface and/or tubing and adheres to the dermal patch 1250 to secure the interface and/or tubing to the patient. The dermal patch 1250 can define a securement footprint that is attached to the patient and has a similar configuration to the corresponding dermal patch 1150 in the above described attachment mechanism. The user side of the dermal patch 1250 is configured to attach or adhere to the user's skin.

The securing patch 1260 can extend over the user interface and/or associated user interface tubing and affixes to the dermal patch 1250 to secure the user interface to the patient. The securing patch 1260 and the dermal patch 1250 can be configured so that the securing patch can be contained within or bounded by the securement footprint of the dermal patch when the securement system is applied to a patient with a suitable or compatible user interface. Containing the securing patch 1260 within the dermal patch 1250 securement footprint can reduce the likelihood of unnecessary contact with the patient's skin and the potential for irritation. Ideally, the dermal patch 1250 can have the same or a greater surface area than the securing patch 1260. The dermal patch 1250 may include one part of a two-part mechanical fastener system across its surface or parts of its surface, with the securing patch 1260 having the other part of the fastening system.

In this manner, the dermal patch can be sized to reduce the likelihood of the taping or any additional taping to extend onto the skin of the user. Avoiding or minimizing the application, or repeated application and removal, of adhesives to a user's skin is preferred. This embodiment beneficially reduces the likelihood of repeated application of adhesive, or adhesive tape, to a user's skin for the installation and placement of a user interface into an operational position. Adhesive tapes or other dermal adhesive patches (when repeatedly applied and remove), particularly for infants, create problems. Problems include, but are not limited to, skin irritation from adhesive chemicals (or adhesive removal chemicals, such as solvents) or tape materials (e.g. due to skin sensitivities), damage to user skin due to repeated application and removal of dermal patches or tapes for positioning or re-positioning of the interface for the user. Re-positioning may be required or adjustments may be needed where treatment therapies are being cycled (i.e. changed from one type of treatment to another, and then back again). Advantageously therefore, the described embodiments provide for a system of positioning or locating of a user interface for a user, yet reducing the likelihood of the problems associated with adhesive tapes attached to the users skin.

It should be appreciated there are a number of disadvantages and problems associated with the re-positioning of an interface, particularly an infant interface. Included is "snub nosing", epidermal abrasion, or dermal allergies from traditional taping techniques for application of user interfaces (e.g. nasal cannula) to users. Such problems are also incurred during the cycling of a user between different treatment options and, traditionally, the subsequent removal of headgear or tapes or user interfaces and then the installation of new equipment and user interfaces or interface positioning headgear or other gear. Therefore, provision of a securement system which, when applied to a user, is in a ready-to-receive mode for receiving a user interface is a useful step in progressing toward reducing the problems users have previously been faced with. Further, improving the ease of installation, both in terms of complexity as well as time and effort by a carer (e.g. nurse), is of further benefit.

The securement patch may be shaped or otherwise configured to accommodate geometric or other features of the user interface and/or associated user interface tubing. The illustrated securement patches can have a plurality of wings 1261 that accommodate the user interface tubing and increase the contact surface of the securing patch 1260 exposed to the dermal patch 1250. The securing patches illustrated in FIGS. 14F-14D each have a pair of wings arranged at one end of the patch. The wings 1261 can be configured to secure to the dermal patch on either side of a user interface and/or associated user interface tubing and reduce the potential for the securing patch 1260 to bunch about the interface and/or tubing.

The securement patch 1261 illustrated in FIG. 14D can also have a tube end wing 1261. The tube end wing 1261 can be configured to extend under the user interface tubing and affix to the dermal patch 1250 to link the ends of the securing patch 1260.

The above described embodiments of the attachment mechanisms can be used to secure tubing to any part of a patient's body. The embodiments illustrated in FIGS. 14A-14D are configured to attach a user interface to a patient's face, in particular, adjacent the user's upper lip and/or cheek. The illustrated securing systems can be adapted for neonatal applications.

The user side of the dermal patches 1150, 1250 can have a dermatologically sensitive adhesive (such as a hydrocolloid) that adheres the patch to a user's skin, so that application of the respective securing systems causes as little irritation as possible. The dermal patches 1150, 1250 can have sufficient surface areas to distribute the adhesive and interface retention forces over an adequate area of the user's face to reduce localized pressure build up.

The illustrated securement systems are particularly configured to receive and/or secure the disclosed adaptor and any necessary tubing, such as medicament delivery tubing or nasogastric tubing. The tubing may extend from one or both side(s) of the user's face. In some embodiments, the aforementioned disclosed patient interface and securement systems can include a dynamic interface to absorb the patient's facial movements. As will be disclosed, the dynamic interface dampens the effect of the baby's facial movements on the positioning of the patient interface about the patient's nose. An example of the dynamic interface is disclosed in Applicant's U.S. application Ser. No. 15/028,924, filed on Oct. 16, 2014, that is hereby incorporated by reference.

An example of the attachment mechanism of Applicant's U.S. application Ser. No. 15/028,924 is hereby reproduced as FIGS. 15A-15C, 16A-16C, and 17. In some embodiments, the dynamic interface can incorporate one or more hinges along the device that reacts to facial movements, both natural and forced, and external forces exerted on the interface. The hinges can minimise the effects of the facial movements and external forces on the fitment of the interface on the patient's face, particularly on the placement of the prongs in the patient's nares. As used herein, hinges refers generally to portions on the interface that are configured to bend in one or more directions. The hinges can be configured to bend in a predefined direction or directions, and in some embodiments the hinges can be restricted from bending in certain directions.

Figure 15A:
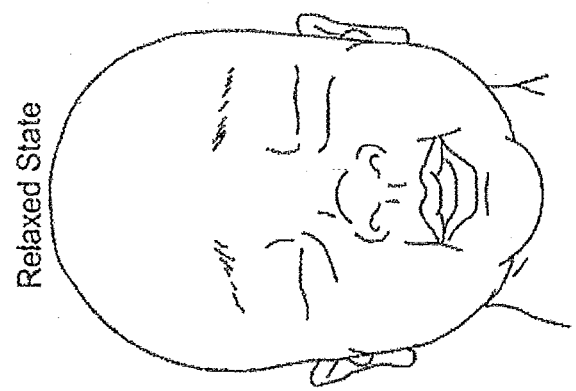
Figure 15B:
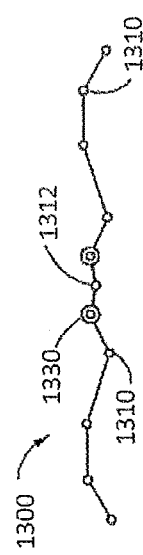
Figure 15C:

FIGS. 15A-15B illustrate an example of a relaxed facial shape of an infant and FIG. 15C illustrates a schematic of the geometric shape of a dynamic interface 1300 on a relaxed face. FIG. 15A is a front view of an infant's face and FIG. 15B is a bottom view of the infant's face. FIG. 15C is a bottom view of a dynamic interface. The dynamic interface 1300 can have one or more hinges 1310. Preferably, the dynamic interface has a center hinge 1312 disposed between the prongs 1330. As can be noticed by comparing FIGS. 4B and 4C, the plurality of hinges 1310 on the interface allows the interface 1300 to conform to the general contours of the patient's face.

Figure 16A:
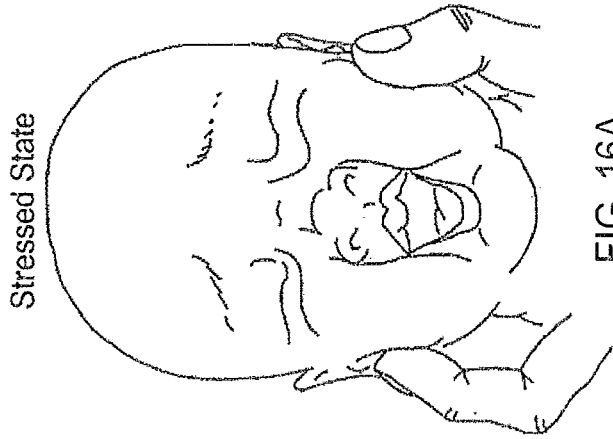
Figure 16B:
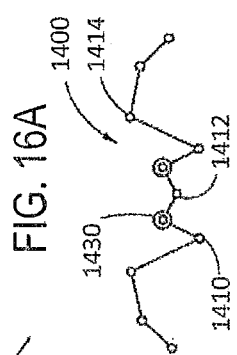
Figure 16C:

FIGS. 16A-B illustrates a front view and a bottom view, respectively, of an example of a stressed or squeezed facial shape of an infant. FIG. 16C illustrates a bottom view schematic of the geometric shape of a dynamic interface 1400 on a squeezed face. The squeezed face approximates, for example, the contortion of the face when patients lie on the side of their faces. As illustrated in FIG. 16C, the hinges 1410 help conform the interface 1400 to the shape of the contorted face and maintain the position of the prongs 1430 in the nares of the patient. The dynamic interface 1400 is particularly helpful in the case of infants who tend to exhibit exaggerated cheek movement.

Each hinge 1410 can be configured to react to an applied force in a predetermined fashion and different hinges can react differently depending on their position on the interface. For example, a hinge 1412 located in the region between the prongs 1430 may bend downward toward the lips and/or inward toward the face to form a concave shape when viewed from the front, while the hinges 1414 adjacent the cheeks of the patient may bend outward to form a convex shape around the cheeks. The hinge 1412 can resist movement outwards normal to the face and minimize the movement of the prongs 1430 out of the nares due to forces applied laterally on the device. In some situations, the bending of hinge 1412 can be limited by the patient's anatomy. For example, the inward bending of hinge 1412 can be limited by the philtrum of the patient, which can beneficially limit the displacement of the prongs 1430. The forces applied to the interface may act on the other hinges (e.g., hinges 1414 adjacent the cheeks) once the hinge 1412 reaches its limit. Combinations of hinge types and hinge locations can allow the designer to control how an interface will react in a variety of situations. A hinge may be designed to allow for 1, 2 or 3 degrees of motion in any predefined direction depending on its desired function. Advantageously, an inherently stable interface can be developed that keeps the prongs in the patients nares under various loading conditions.

Another example of a dynamic nasal interface 1500 is illustrated in FIG. 17C. Although the pictured interface is a nasal cannula, the hinging portions could be adapted to support the disclosed adaptor of the present application using the same principles, such as by including a hinging extension portion attachable to a patch as discussed above.

Figure 17:
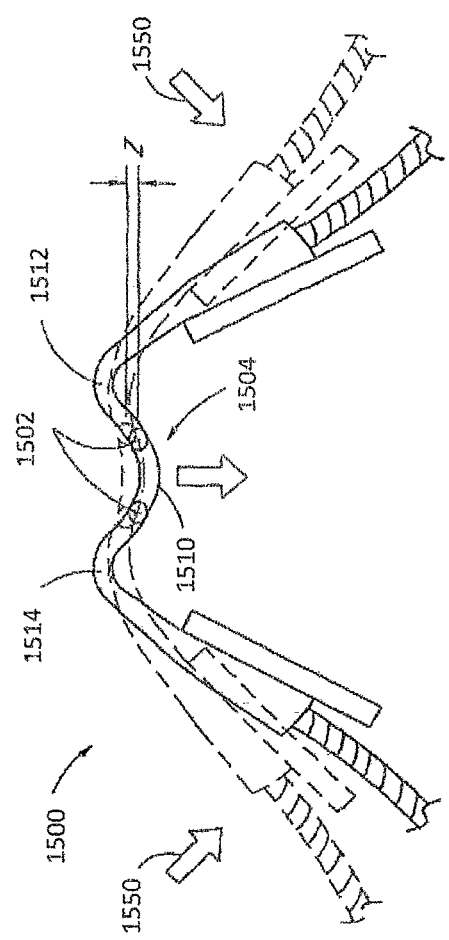

For example, FIG. 17 illustrates a nasal interface 1500 having hinges in at least three locations, the bridge hinge 1510 and outer hinges 1512, 1514 on either sides of the prongs. The additional hinges of the nasal interface help stabilize the positions of the prongs 1502 when the cannula is under stress and reduce the displacement distance, helping to keep the prongs in the nares of the patient and reduce the irritation of the nares by the prongs. In some embodiments, the bridge hinge 1510 and outer hinges 1512, 1514 can be configured to be attachable to the aforementioned patch so as to support the disclosed adaptor.

Additional embodiments of dynamic interfaces are further illustrated in FIGS. 8-28 of U.S. application Ser. No. 15/028, 924, filed on Oct. 16, 2014, of which description is herein incorporated by reference.

In some embodiments, the adaptor 100 can include an inlet port 160 that can be fluidly connected an inspiratory tube 6 from a humidification apparatus and allow fluid flow through the inlet tube 164 in a first direction. The inlet tube 164 can include an engagement portion 165 at a first end that engages with the inspiratory tube 6. In some embodiments, the inlet tube 164 is secured to the inspiratory tube 6 using a securing portion 168. The securing portion 168 can allow the inlet tube 164 to be removably attached to the inspiratory tube 6. For example, as illustrated in FIGS. 2A and 2B, the securing portion 168 can be a tab that is secured to a complementary securing portion in the inspiratory tube 6. However, the securing portion 168 can come in any shape and size, such as a latch, threaded portion, or any locking feature that has a complementary securing portion on the inspiratory tube 6. In some embodiments, the securing portion 168 can allow the adaptor 100 to be directly attached to the respiratory assistance system 1. This can help, for example, to reduce the number of parts in the respiratory assistance system 1 as well as reduce the manufacturing costs.

Figure 3A:
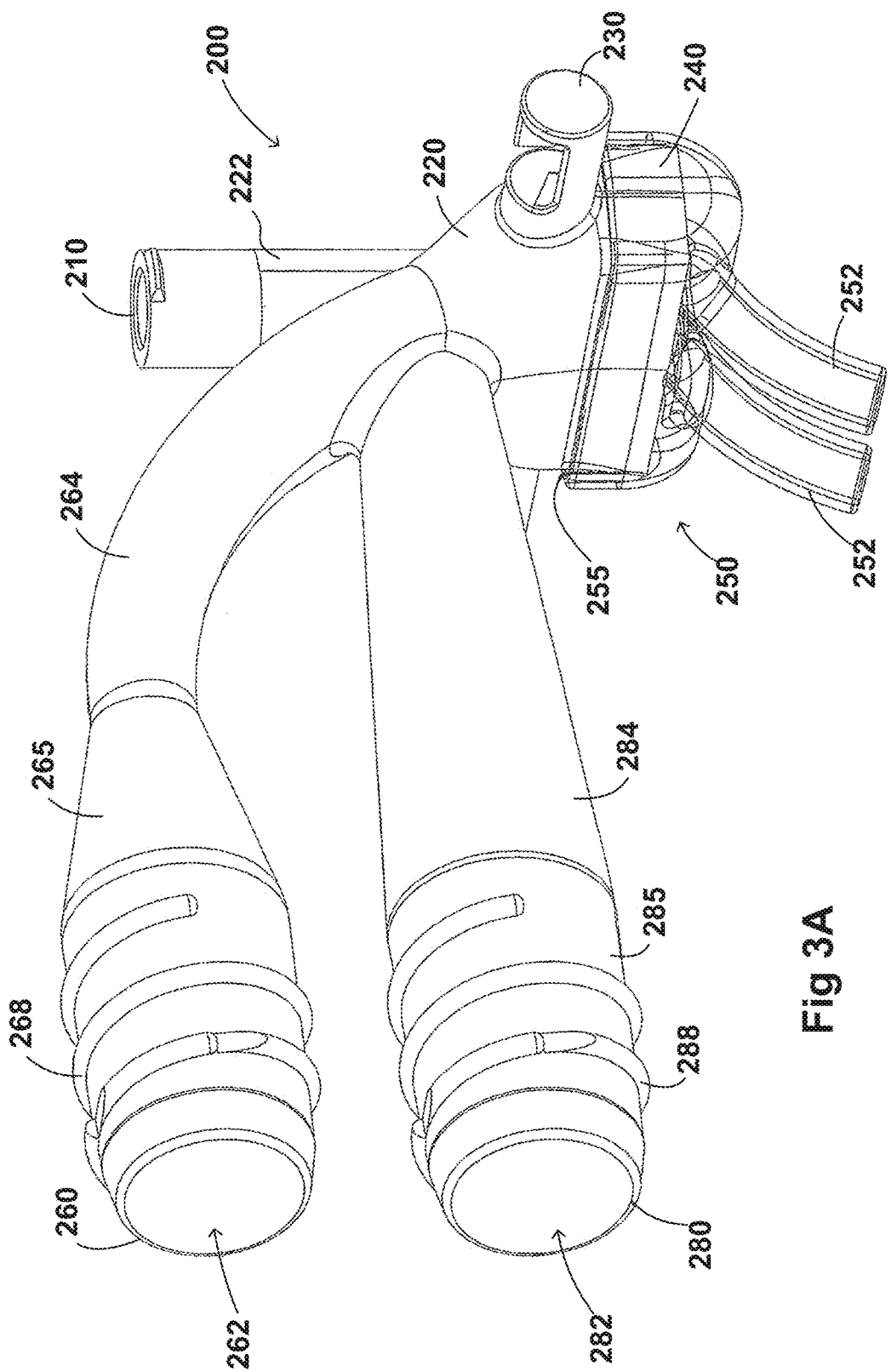
Figure 3B:
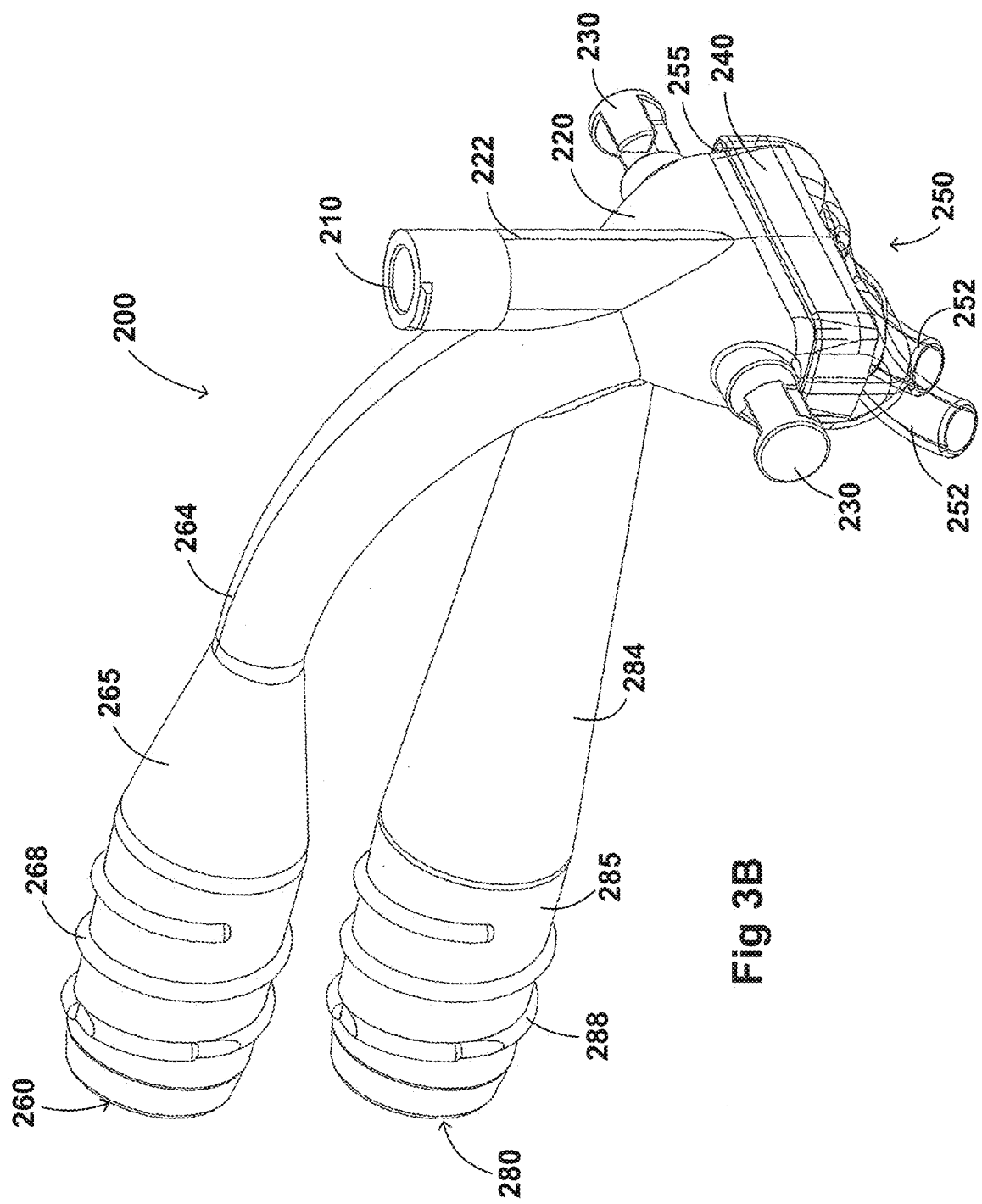
Figure 3C:
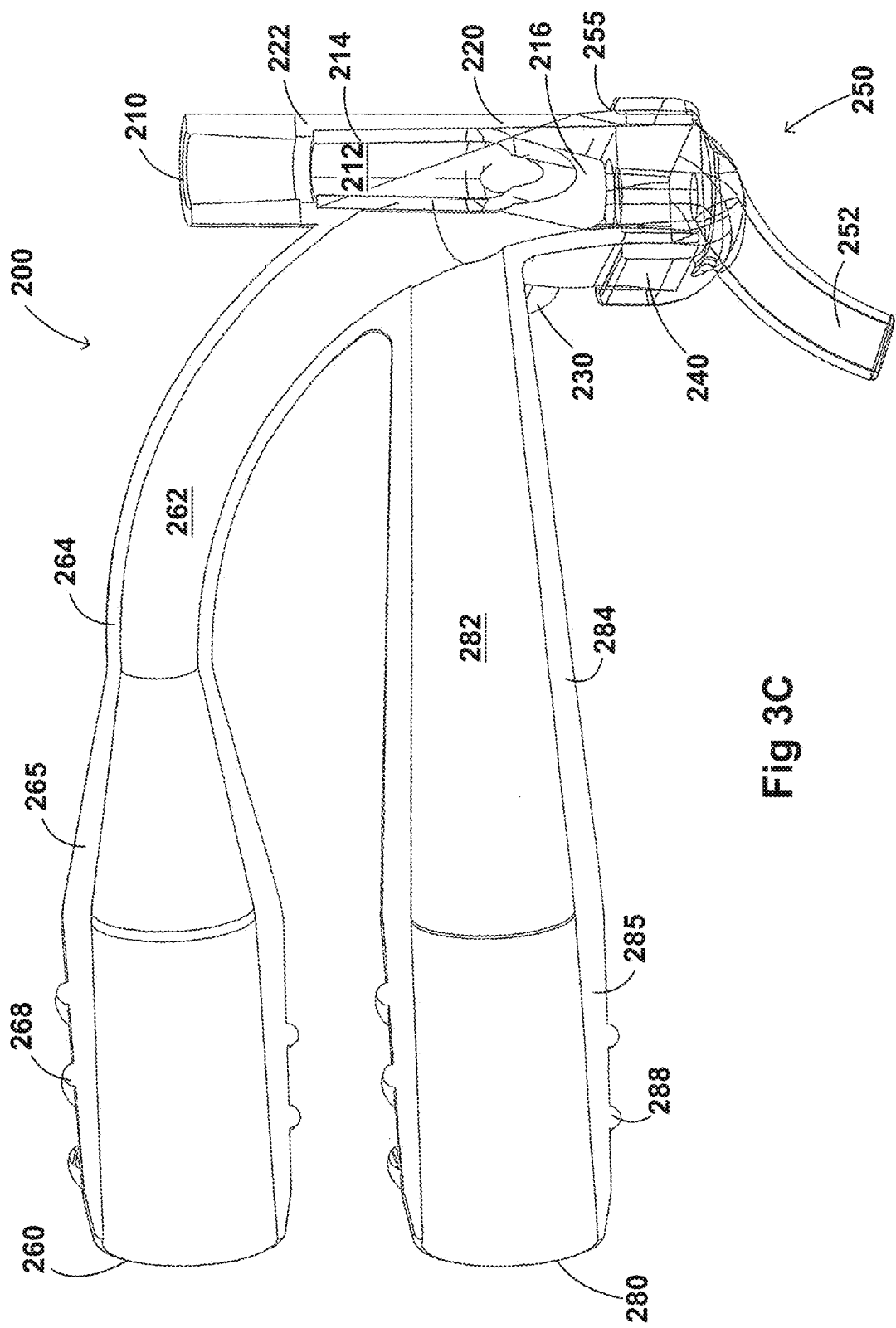
Figure 3D:
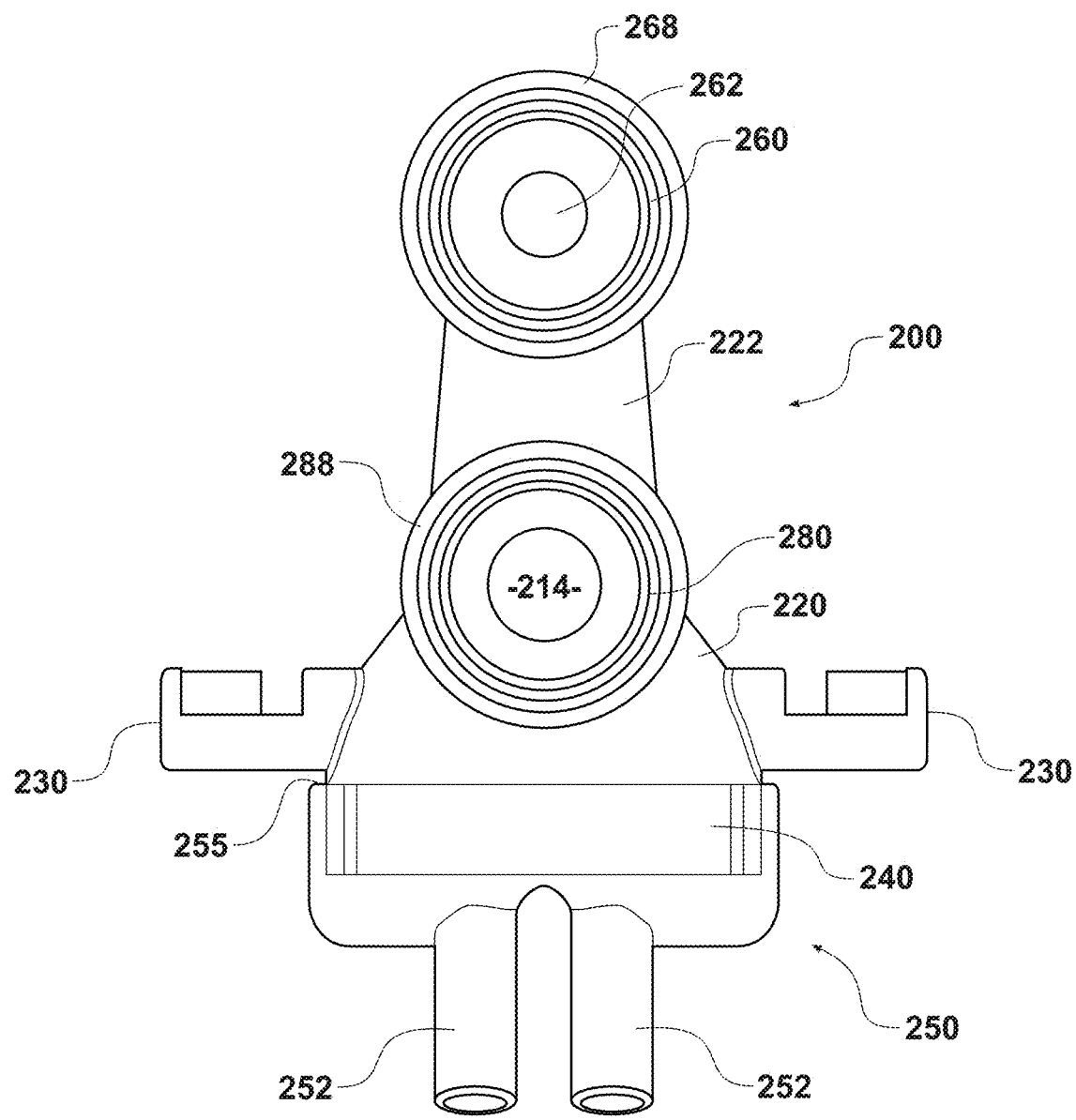
Figure 3F:
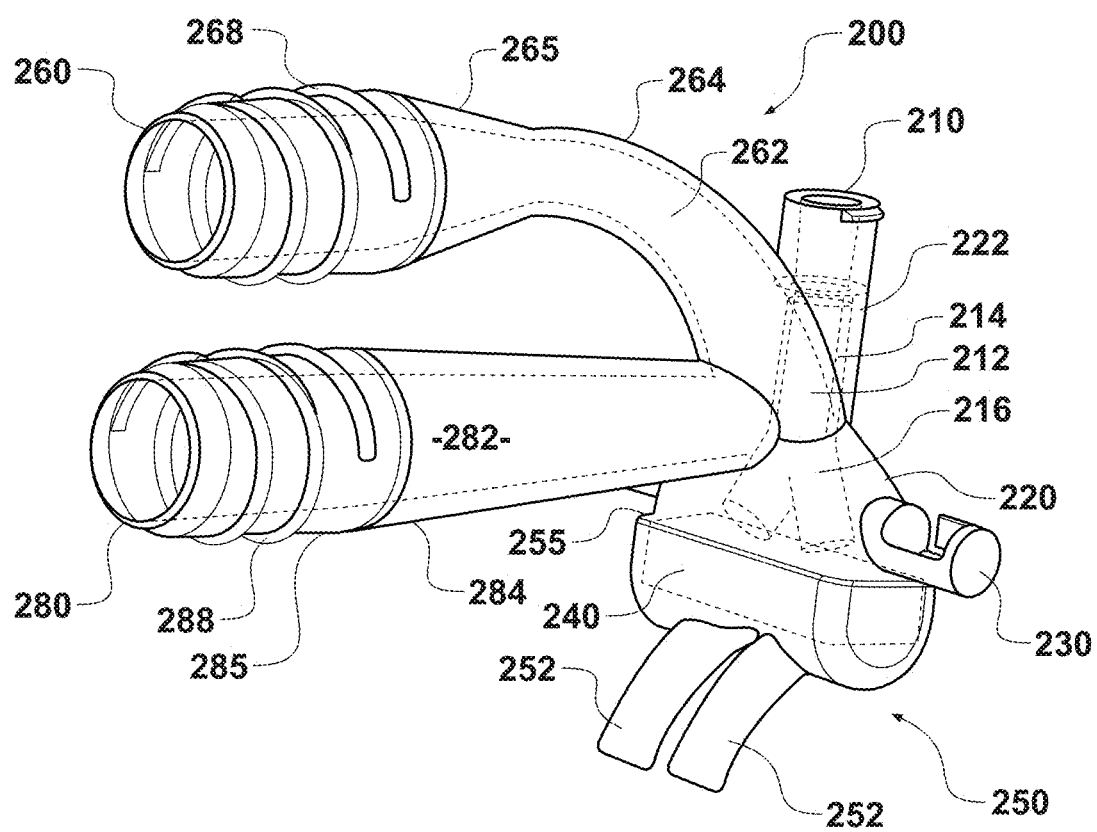

In some embodiments, the outlet port 180 can be configured to receive an expiratory tube 4 to a pressure regulating device 7. In some examples, the outlet port 180 can be fluidly connected to the respiratory assistance system 1 to allow fluid flow through the outlet tube 184 in a second direction. The outlet tube 184 can include an engagement portion 165 at a first end that engages with the expiratory tube 4. In some embodiments, the outlet tube 184 can be secured to the expiratory tube 4 using a securing portion 188. The securing portion 188 can allow the outlet tube 184 to be removably attached to the expiratory tube 4. For example, as illustrated in FIGS. 3A and 3B, the securing portion 188 can be a tab that is secured to a complementary securing portion in the expiratory tube 4. However, the securing portion 188 can come in any shape and size, such as a latch, threaded portion, or any locking feature that has a complementary securing portion on the expiratory tube 4. As was discussed with regard to the securing portion 168, in some embodiments, the securing portion 188 can allow the adaptor 100 to be directly attached to the respiratory assistance system 1. This can help, for example, to reduce the number of parts in the respiratory assistance system 1 as well as reduce the manufacturing costs.

In some embodiments, the inlet tube 164 and the outlet tube 184 are configured to extend above and away from the patient. In some embodiments, the "over" and "under" design of the inlet tube 164 and the outlet tube 184 can help to reduce mass across the patient's face. In some examples, the inlet tube 164 and the outlet tube 184 can be more rigid so as to able to hold onto its shape without contacting the patient. The inlet tube 164 and outlet tube 184 can help to reduce the weight perceived by the patient by spreading out or increasing the distribution of forces from the interface and tubing, reducing patient discomfort. In some embodiments, the location of the inlet port 160 and the outlet port 180 can be alternated.

In some embodiments, the adaptor 100 can include an integrated nozzle 122 that is configured to connect with an external device to provide a fluid connection with the inside of the housing 120. In some examples, the nozzle 122 can be disposed about another conduit to isolate and restrict the mixing of the aerosolized material (for example, a drug) with the air flow coming through the inlet tube 164.

As illustrated in FIGS. 2C-2F, in some embodiments, the nozzle 122 can be disposed about a surfactant tube 114. The surfactant tube 114 can have a surfactant port 110, an internal surfactant lumen 112, and a bifurcated portion 116. In some examples, the surfactant tube 114 can have a surfactant port 110 at a first end of the surfactant tube 114 that is configured to be fluidly connected to the respiratory assistance system 1 to allow the delivery of a substance, such as an aerosolized surfactant, to the housing 120 and to the patient through the patient interface 150.

In some embodiments, the surfactant tube 114 can be fluidly connected with an external device such as a medicament delivery device. In some embodiments, the medicament delivery device can be a nebulizer, a capillary aerosol generator, or a metered dose inhaler (MDI). A nebuliser such as a flow based nebuliser, for example, can deliver aerosolised surfactant to the patient. In some embodiments, a nebuliser can be configured to deliver a medicament or anaesthetic substance to the patient.

In some embodiments, the surfactant tube 114 can have a circular cross-section which ensures that the surfactant lumen 112 does not have any sharp edges so as to reduce deposition within the surfactant lumen 112. The surfactant tube 114 is not limited to a tubular shape, and can comprise any number of shapes. The surfactant port 110 of the surfactant tube 114 is located directly over the nose so as to reduce the deposition of medicament within the surfactant lumen 112 and ensure sufficient delivery of medicament to the patient.

Figure 2G:
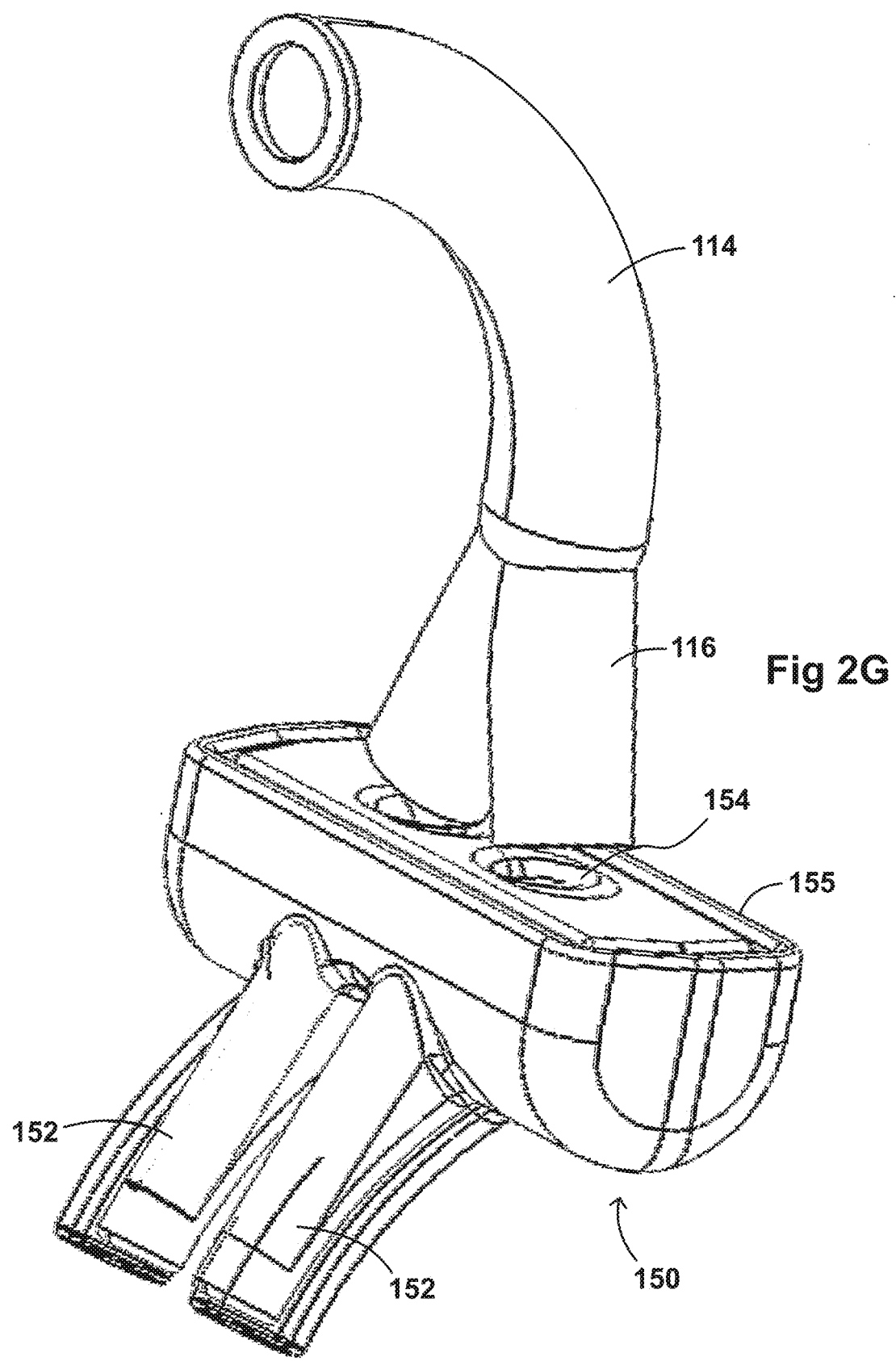

Turning to FIG. 2G, in some examples, the surfactant tube 114 can have a bifurcated portion 116 that allows the surfactant tube 114 to be fluidly connected to both nostril lumens 154 of the nasal prongs 152 so as to allow medicament to be delivered through both nostrils of the patient.

The body of the adaptor 100 can be divided into a plurality of compartments. FIGS. 2C-2F illustrate the configuration of the adaptor 100 and the airflow through the inlet lumen 162, outlet lumen 182, surfactant lumen 112, and the housing 120. The plurality of compartments within the adaptor 100 can reduce premixing of the medicament received through the surfactant port 110 and the inspiratory gases through the inlet lumen 162 and reduce dilution of the drug by the outgoing gases through the outlet port 180. In some examples, the arrangement of the conduits within the adaptor 100 can help to maximize gas flow to the patient. For example, inspiratory gases can enter the adaptor 100 through the inlet port 160 and flow through the inlet lumen 162 and into the housing 120. There, the gases can mix with the medicament delivered from the bifurcated portion 116 surfactant tube 114 near the opening of the nostril lumens 154. As illustrated in FIG. 2G, there is a gap between the end of the bifurcated portion 116 of the surfactant tube 114 and the nostril lumens 154 of the patient interface 150 that allow inspiratory gases to flow in. In some embodiments, the expiratory gases can then exit the patient interface 150 and move around the surfactant tube 114, flow through the outlet lumen 182, and exit the adaptor 100 from the outlet port 180.

FIGS. 3A-3H illustrate another embodiment of an adaptor 200. The adaptor 200 resembles or is identical to the adaptor 100 in many respects. Accordingly, the numerals used to identify components of the system for adaptor 100 are incremented by one hundred to identify like features of the adaptor 200. This number convention generally applies to the remainder of the Figures. Any component disclosed in any embodiment in this specification can be used in other embodiments.

Turning first to FIGS. 3A and 3B, illustrated is an embodiment of the adaptor 200. Like the adaptor 100, the adaptor 200 can include a housing 220 that is fluidly connected to a plurality of conduits to provide fluid flow, such as air, and the delivery of aerosolized surfactants to the patient through the patient interface 250. The adaptor 200 can include a housing 220, a plurality of clips 230, an inlet port 260, an outlet port 280, a surfactant port 210 and a coupling surface 240 for engaging a patient interface 250.

In some examples, as with the housing 120, the housing 220 can include a substantially hollow cylindrical body. The shape of the housing 220 can be optimized to reduce resistance to flow within the housing 220. In some examples, the housing 220 can comprise different shapes, for example, rectangular, square, hexagonal, or semi-circular. In some embodiments the shape of the housing 220 can minimize volume within the housing 220. This can reduce dead space—therefore reducing the build-up of carbon dioxide within the housing 220. The housing 220 can be compact so as to reduce the weight and bulk of the housing 220 and improve patient comfort. As discussed with regard to the adaptor 100, the housing 220 can be configured to both receive gases through an inspiratory tube and aid the exit of gases through an expiratory tube.

The housing 220 can include a coupling surface 240 at an end of the housing 220 that is proximate to the patient. As illustrated in FIGS. 3A-3B, the coupling surface 340 can be rectangular in cross-section. The coupling surface 240 can include a first end that is fluidly connected with the housing 220 and a second end that is configured to couple with the patient interface 250. The second end of the coupling surface 240 can allow fluid communication between the housing 220 and the patient interface 250. In some embodiments, a partial barrier can exist between the housing 220 and the first end of the coupling surface 240. An orifice can thus maintain fluid communication between the housing 220 and the patient interface 250. The orifice can direct the flow of gases toward the patient interface 250. In some examples, the orifice can control the pressure of the gas flow as it enters the patient interface 250.

In some embodiments, the patient interface 250 is similar if not identical to the patient interface 150 of adaptor 100. As discussed, the patient interface 250 can be configured to be removably coupled with the coupling surface 240. In some examples the patient interface 250 can be coupled with the coupling surface 240 using adhesives or mechanical mechanisms such as snap-fit mechanisms. In some embodiments, the patient interface 250 can be permanently attached to the coupling surface 240 using adhesives, snap-fit mechanisms, or welding techniques. FIGS. 3A-3H illustrate a patient interface 250 that is transparent so as to allow the engagement between the coupling surface 240 and the patient interface 250 to be visualized. The patient interface 250 can include a substantially hollow complementary region 255 that is configured to receive the coupling surface 240. As noted above, an embodiment of the complementary region of the patient interface can be visualized in FIG. 2G. In some embodiments, the coupling surface 240 can be configured to receive the complementary region 255 of the patient interface 250. In some embodiments, the patient interface 250 can be permanently coupled with the adaptor 200. This can provide a fully integrated adaptor which may improve the usability of the adaptor 200.

As illustrated in FIGS. 3A-3B, in some examples, the patient interface 250 can include nasal prongs 252. In some embodiments, the patient interface 250 can include respiratory interfaces such as, but not limited to, a nasal mask, oral mask, combined nasal and oral mask, tracheal mask, or nasal pillows. In some embodiments, the adaptor 200 can be adapted for use in a surgical application. The patient interface 250 can include a diffuser, trocar, or catheter.

In some embodiments, the adaptor 200 can include clips 230 that are positioned on first and second sides of the housing 220. As illustrated in FIGS. 3A-3B, the first and second sides of the coupling surface 240 can be substantially perpendicular to the first and second ends of the coupling surface 240. In some embodiments, the clips 230 can be configured to be mobile clips. For example, the clip 230 can be positioned on a slidable and/or rotatable bar or cord. In this way, the position of the clips 230 can be rotated or altered to simplify the attachment of the patient stabilising mechanism to the adaptor 200. In some embodiments, the clips 230 can be configured to permanently attach to an interface stabilising mechanism.

As discussed above, in some examples, the clips 230 can engage a removable attachment that is attached to an interface stabilising mechanism, such as headgear or a hat or bonnet. As described above, an example of the removable attachment is illustrated in FIGS. 13A-13B and 14A-14D.

In some embodiments, the adaptor 20 can include an inlet port 260 that can be fluidly connected an inspiratory tube 6 from a humidification apparatus and allow fluid flow through the inlet tube 264 in a first direction. The inlet tube 264 can include an engagement portion 265 at a first end that engages with the inspiratory tube 6. In some examples, the engagement portion 265 has a tapered portion that reduces the diameter of the engagement portion 265 to the diameter of the inlet tube 264. In some embodiments, the inlet tube 264 is secured to the inspiratory tube 6 using a securing portion 268. The securing portion 268 can allow the inlet tube 264 to be removably attached to the inspiratory tube 6. For example, as illustrated in FIGS. 3A and 3B, the securing portion 268 can be threaded and configured to engage internal threading located on a portion of the inspiratory tube 6. However, the securing portion 268 can come in any shape and size, such as a tab, latch, or any locking feature that has a complementary securing portion on the inspiratory tube 6. In some embodiments, the securing portion 268 can allow the adaptor 200 to be directly attached to the respiratory assistance system 1. This can help, for example, to reduce the number of parts in the respiratory assistance system 1 as well as reduce the manufacturing costs.

In some embodiments, the outlet port 280 can be configured to receive an expiratory tube 4 to a pressure regulating device 7. In some examples, the outlet port 280 can be fluidly connected to the respiratory assistance system 1 to allow fluid flow through the outlet tube 284 in a second direction. The outlet tube 284 can include an engagement portion 265 at a first end that engages with the expiratory tube 4. In some embodiments, the outlet tube 284 can be secured to the expiratory tube 4 using a securing portion 288. The securing portion 488 can allow the outlet tube 284 to be removably attached to the expiratory tube 4. For example, as illustrated in FIGS. 3A and 3B, the securing portion 288 can be threaded and configured to engage internal threading located on a portion of the expiratory tube 4. However, the securing portion 288 can come in any shape and size, such as a latch, threaded portion, or any locking feature that has a complementary securing portion on the expiratory tube 4. As was discussed with regard to the securing portion 268, in some embodiments, the securing portion 288 can allow the adaptor 200 to be directly attached to the respiratory assistance system 1. This can help, for example, to reduce the number of parts in the respiratory assistance system 1 as well as reduce the manufacturing costs.

In some embodiments, the inlet tube 264 and the outlet tube 284 are configured to extend above and away from the patient. As illustrated in FIGS. 3A-3B, the engagement portion 265 and the engagement portion 285 are located one above the other, with the engagement portion 265 and engagement portion 285 parallel to each other. In some embodiments, the inlet tube 264 can have a curved portion from the engagement portion 265 to the body of the housing 220. In some embodiments, the curved structure of the inlet tube 264 can help to reduce sharp turns that could potentially cause turbulence and condensation of the surfactant. In some examples, the inlet tube 264 and the outlet tube 284 can be more rigid so as to able to hold onto its shape without contacting the patient. The inlet tube 264 and outlet tube 284 can help to reduce the weight perceived by the patient by spreading out or increasing the distribution of forces from the interface and tubing, reducing patient discomfort. In some embodiments, the location of the inlet port 260 and the outlet port 280 can be alternated. In some examples, the curved inlet tube 264 can be configured to introduce medication as directly into the patient as possible through the nostril lumens 254.

As with the adaptor 100, in some embodiments, the adaptor 200 can include an integrated nozzle 222 that is configured to connect with an external device to provide a fluid connection with the inside of the housing 220. In some examples, the nozzle 222 can be disposed about another conduit to isolate and restrict the mixing of the aerosolized material (for example, a drug) with the air flow coming through the inlet tube 264.

As illustrated in FIGS. 3C-3H, in some embodiments, the nozzle 222 can be disposed about a surfactant tube 214. The surfactant tube 214 can have a surfactant port 210, an internal surfactant lumen 212, and a bifurcated portion 216. In some examples, the surfactant tube 214 can have a surfactant port 210 at a first end of the surfactant tube 214 that is configured to be fluidly connected to the respiratory assistance system 1 to allow the delivery of a substance, such as an aerosolized surfactant, to the housing 220 and to the patient through the patient interface 250.

In some embodiments, the surfactant tube 214 can be fluidly connected with an external device such as a medicament delivery device. In some embodiments, the medicament delivery device can be a nebulizer, a capillary aerosol generator, or a metered dose inhaler (MDI). A nebuliser such as a flow based nebuliser, for example, can deliver aerosolised surfactant to the patient. In some embodiments, a nebuliser can be configured to deliver a medicament or anaesthetic substance to the patient.

In some embodiments, the surfactant tube 214 can have a circular cross-section which ensures that the surfactant lumen 212 does not have any sharp edges so as to reduce deposition within the surfactant lumen 212. The surfactant tube 214 is not limited to a tubular shape, and can comprise any number of shapes. The surfactant port 210 of the surfactant tube 214 is located directly over the nose so as to reduce the deposition of medicament within the surfactant lumen 212 and ensure sufficient delivery of medicament to the patient.

As discussed above with regard to FIG. 2G, in some examples, the surfactant tube 214 can have a bifurcated portion 216 that allows the surfactant tube 214 to be fluidly connected to both nostril lumens 254 of the nasal prongs 252 so as to allow medicament to be delivered through both nostrils of the patient.

The body of the adaptor 200 can be divided into a plurality of compartments. FIGS. 3C-3H illustrate the configuration of the adaptor 200 and the airflow through the inlet lumen 262, outlet lumen 282, surfactant lumen 212, and the housing 220. The plurality of compartments within the adaptor 200 can reduce premixing of the medicament received through the surfactant port 210 and the inspiratory gases through the inlet lumen 262 and reduce dilution of the drug by the outgoing gases through the outlet port 280. In some examples, the arrangement of the conduits within the adaptor 200 can help to maximize gas flow to the patient. For example, inspiratory gases can enter the adaptor 200 through the inlet port 260 and flow through the inlet lumen 262 and into the housing 220. There, the gases can mix with the medicament delivered from the bifurcated portion 216 surfactant tube 214 near the opening of the nostril lumens 254. Similar to the surfactant tube 114 in FIG. 2G, there is a gap between the end of the bifurcated portion 216 of the surfactant tube 214 and the nostril lumens 254 of the patient interface 250 that allow inspiratory gases to flow in. In some embodiments, the expiratory gases can then exit the patient interface 250 and move around the surfactant tube 214, flow through the outlet lumen 282, and exit the adaptor 200 from the outlet port 280.

FIGS. 4A-4G illustrate another embodiment of an adaptor 300. The adaptor 300 resembles or is identical to the adaptor 100 in many respects. Accordingly, the numerals used to identify components of the system for adaptor 100 are incremented by one hundred to identify like features of the adaptor 300. This number convention generally applies to the remainder of the Figures. Any component disclosed in any embodiment in this specification can be used in other embodiments.

Figure 4A:
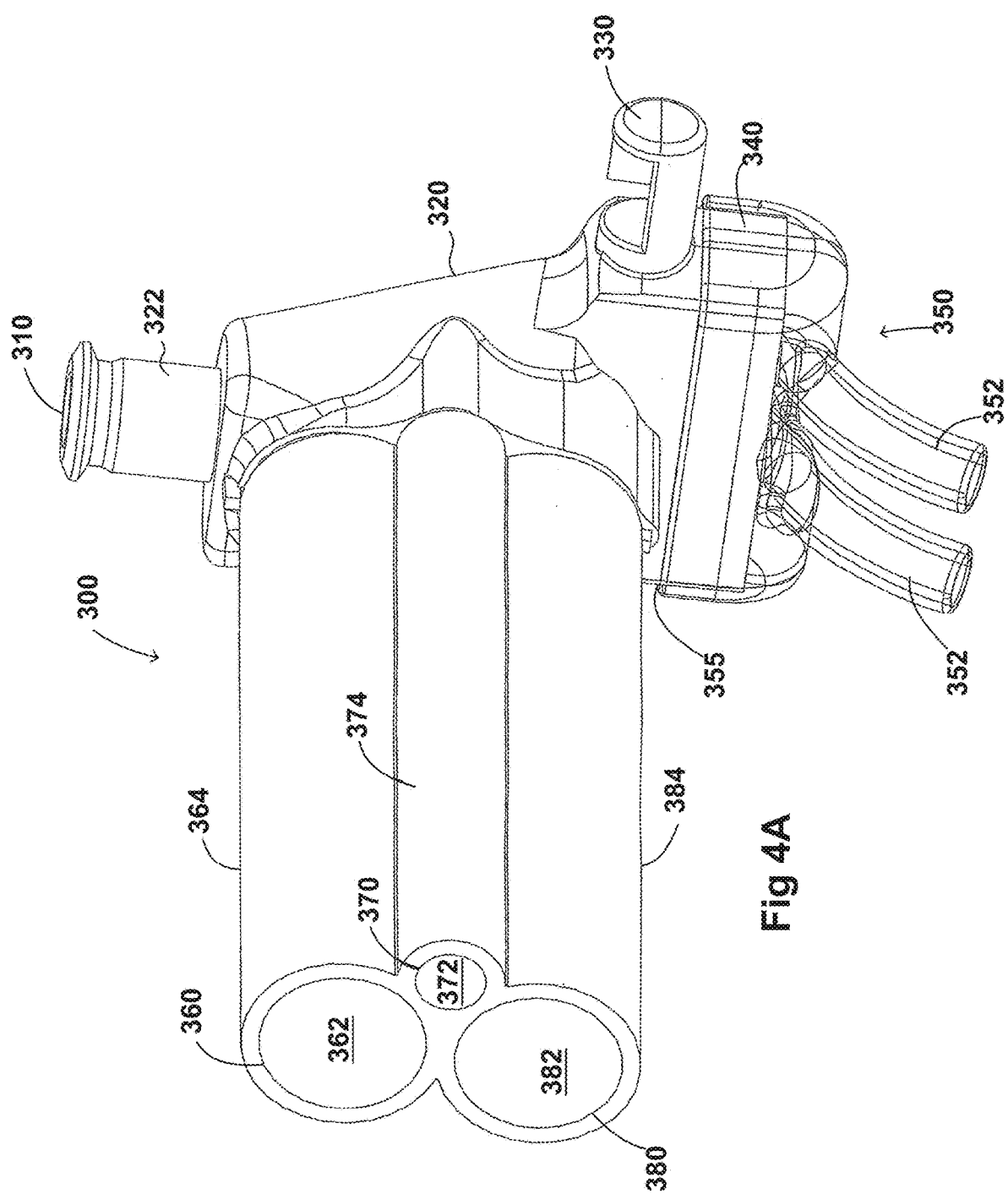
Figure 4D:
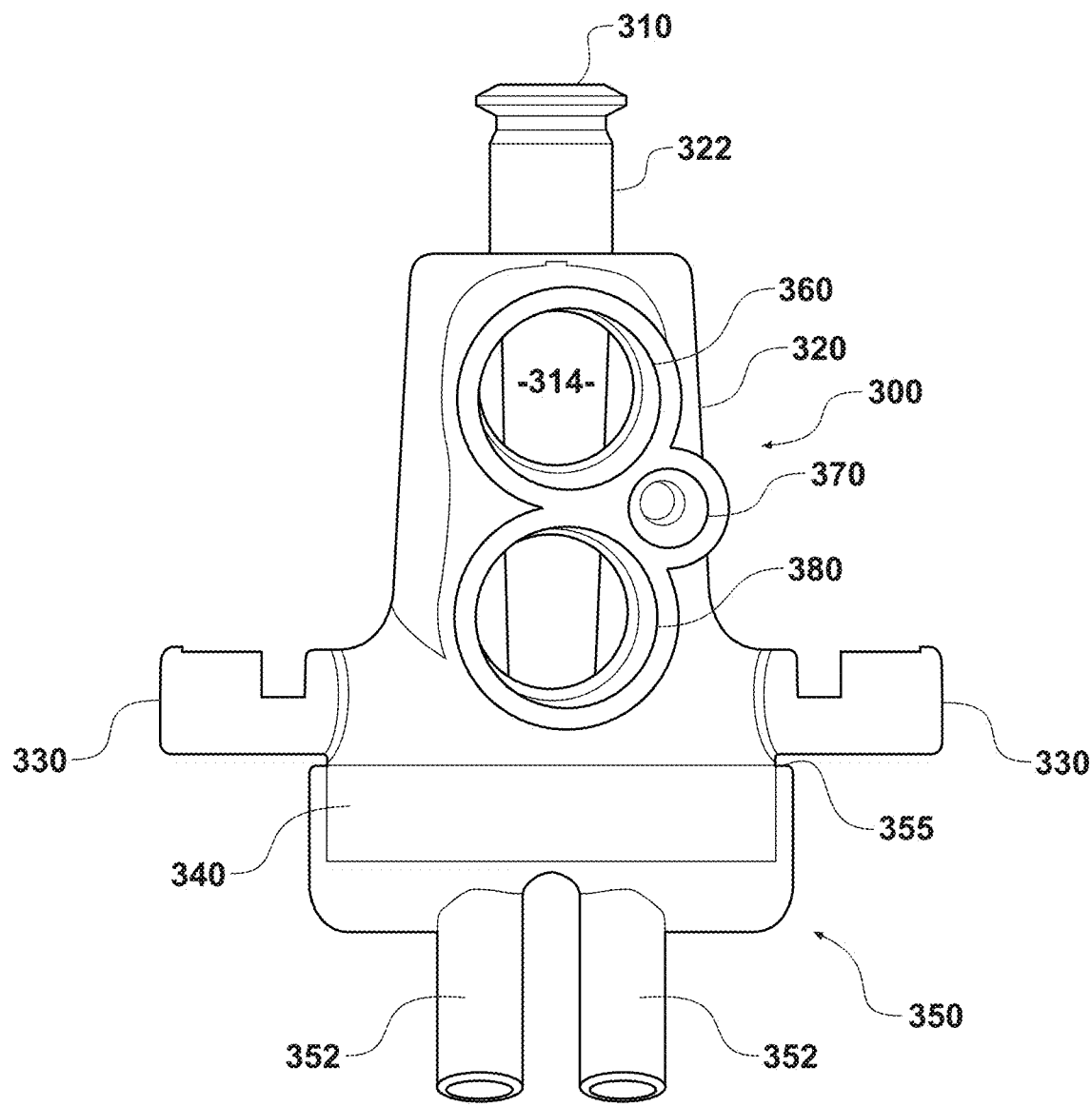
Figure 4F:
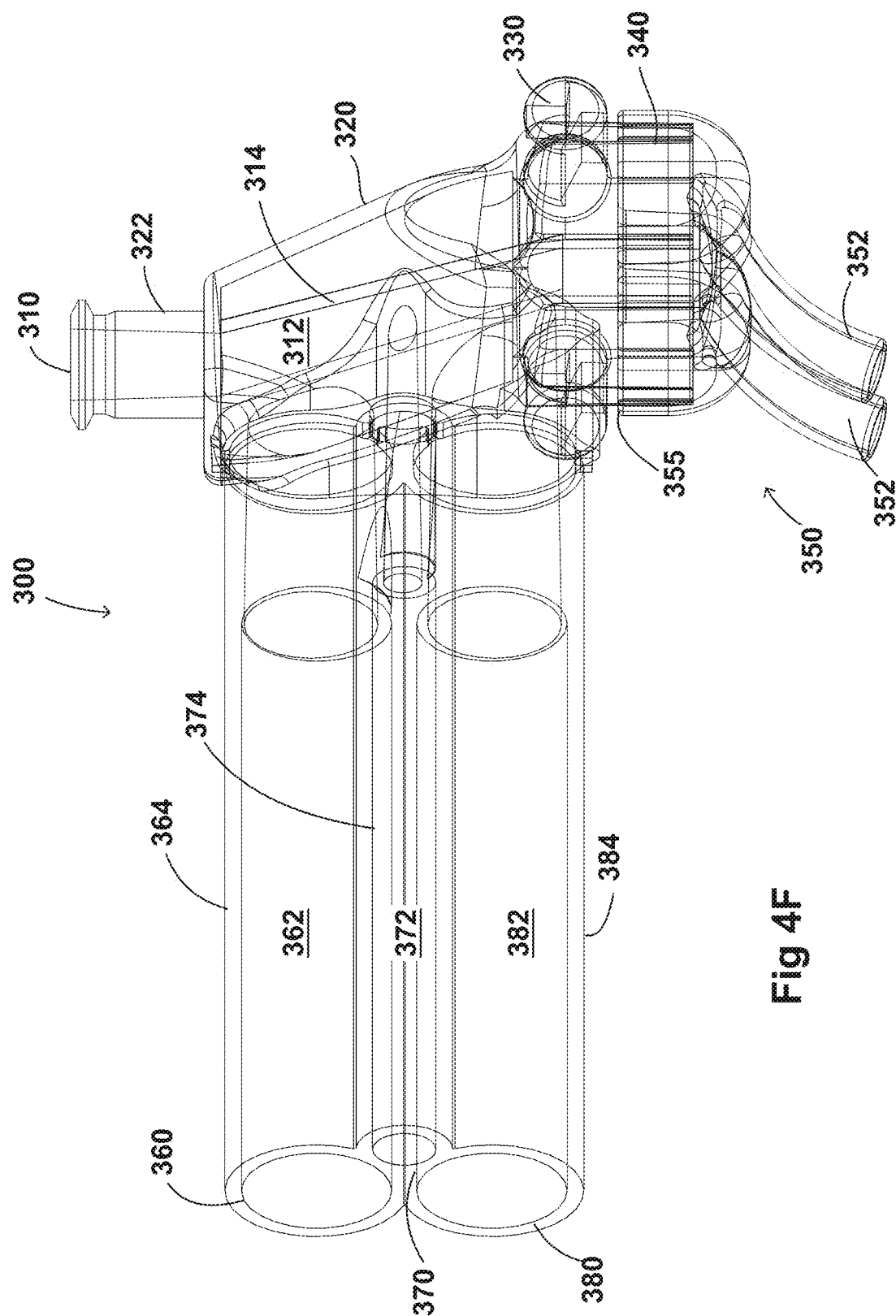
Figure 4G:
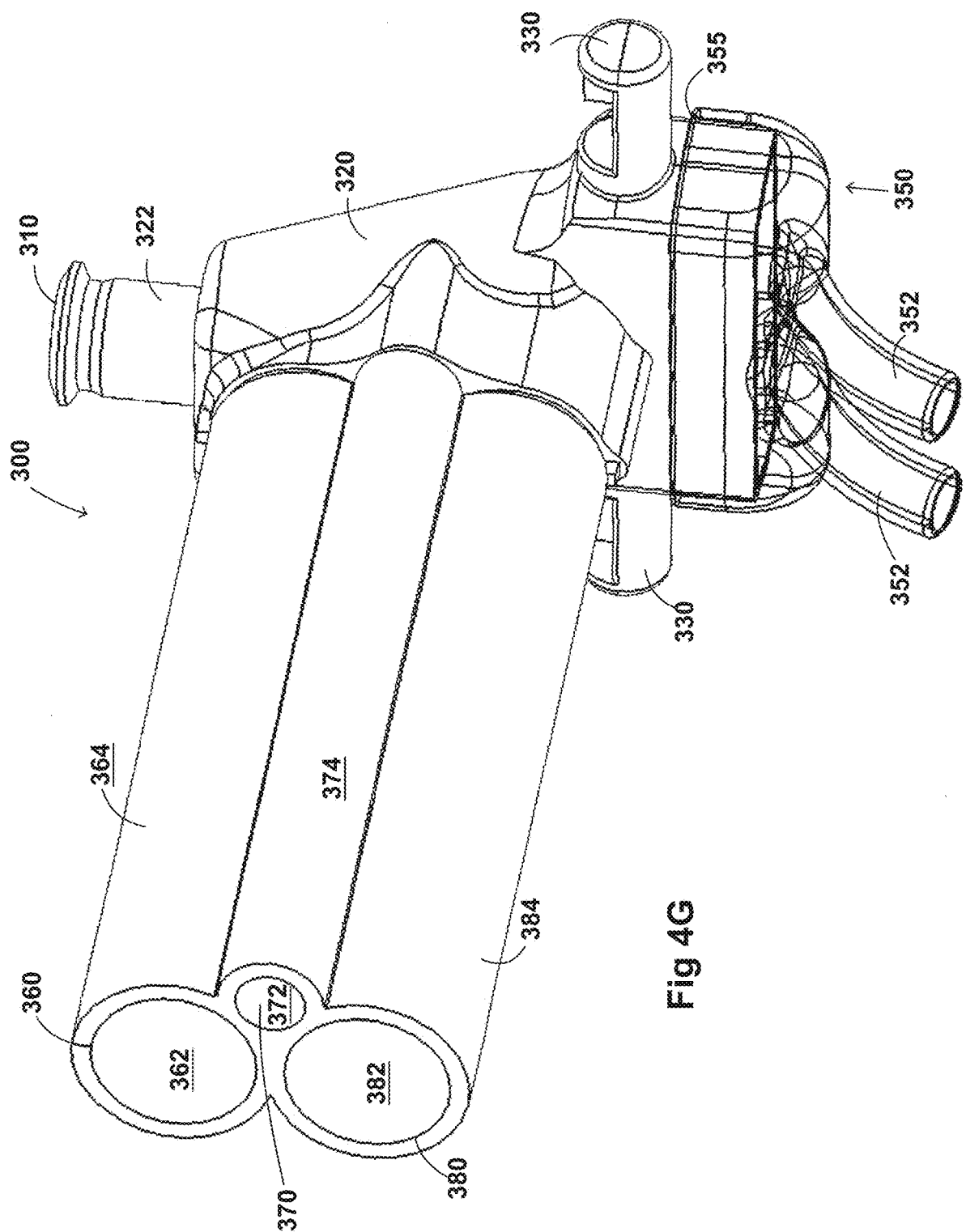

Turning first to FIGS. 4A and 4B, illustrated is an embodiment of the adaptor 300. Like the adaptor 100, the adaptor 300 can include a housing 320 that is fluidly connected to a plurality of conduits to provide fluid flow, such as air, and the delivery of aerosolized surfactants to the patient through the patient interface 350. The adaptor 300 can include a housing 320, a plurality of clips 330, an inlet port 360, an outlet port 380, a pressure port 370, a surfactant port 310 and a coupling surface 340 for engaging a patient interface 350.

In some examples, as with the housing 120, the housing 320 can include a substantially hollow cylindrical body. The shape of the housing 320 can be optimized to reduce resistance to flow within the housing 320. In some examples, the housing 320 can comprise different shapes, for example, rectangular, square, hexagonal, or semi-circular. In some embodiments the shape of the housing 320 can minimize volume within the housing 320. This can reduce dead space—therefore reducing the build-up of carbon dioxide within the housing 320. The housing 320 can be compact so as to reduce the weight and bulk of the housing 320 and improve patient comfort. As discussed with regard to the adaptor 100, the housing 320 can be configured to both receive gases through an inspiratory tube and aid the exit of gases through an expiratory tube.

The housing 320 can include a coupling surface 340 at an end of the housing 320 that is proximate to the patient. As illustrated in FIGS. 4A-4B, the coupling surface 340 can be rectangular in cross-section. The coupling surface 340 can include a first end that is fluidly connected with the housing 320 and a second end that is configured to couple with the patient interface 350. The second end of the coupling surface 340 can allow fluid communication between the housing 320 and the patient interface 350. In some embodiments, a partial barrier can exist between the housing 320 and the first end of the coupling surface 340. An orifice can thus maintain fluid communication between the housing 320 and the patient interface 350. The orifice can direct the flow of gases toward the patient interface 350. In some examples, the orifice can control the pressure of the gas flow as it enters the patient interface 350.

In some embodiments, the patient interface 350 is similar if not identical to the patient interface 150 of adaptor 100. As discussed, the patient interface 350 can be configured to be removably coupled with the coupling surface 340. In some examples the patient interface 350 can be coupled with the coupling surface 340 using adhesives or mechanical mechanisms such as snap-fit mechanisms. In some embodiments, the patient interface 350 can be permanently attached to the coupling surface 340 using adhesives, snap-fit mechanisms, or welding techniques. FIGS. 4A-4G illustrate a patient interface 350 that is transparent so as to allow the engagement between the coupling surface 340 and the patient interface 350 to be visualized. The patient interface 350 can include a substantially hollow complementary region 355 that is configured to receive the coupling surface 340. As noted above, an embodiment of the complementary region of the patient interface can be visualized in FIG. 2G. In some embodiments, the coupling surface 340 can be configured to receive the complementary region 355 of the patient interface 250. In some embodiments, the patient interface 350 can be permanently coupled with the adaptor 300. This can provide a fully integrated adaptor which may improve the usability of the adaptor 300.

As illustrated in FIGS. 4A-4B, in some examples, the patient interface 350 can include nasal prongs 352. In some embodiments, the patient interface 350 can include respiratory interfaces such as, but not limited to, a nasal mask, oral mask, combined nasal and oral mask, tracheal mask, or nasal pillows. In some embodiments, the adaptor 300 can be adapted for use in a surgical application. The patient interface 350 can include a diffuser, trocar, or catheter.

In some embodiments, the adaptor 300 can include clips 330 that are positioned on first and second sides of housing 320. As illustrated in FIGS. 4A-4B, the first and second sides of the coupling surface 340 can be substantially perpendicular to the first and second ends of the coupling surface 340. In some embodiments, the clips 330 can be configured to be mobile clips. For example, the clip 330 can be positioned on a slidable and/or rotatable bar or cord. In this way, the position of the clips 330 can be rotated or altered to simplify the attachment of the patient stabilising mechanism to the adaptor 300. In some embodiments, the clips 330 can be configured to permanently attach to an interface stabilising mechanism.

As discussed above, in some examples, the clips 330 can engage a removable attachment that is attached to an interface stabilising mechanism, such as headgear or a hat or bonnet. As described above, an example of the removable attachment is illustrated in FIGS. 13A and 13B.

In some embodiments, the adaptor 300 can include an inlet port 360 that can be fluidly connected an inspiratory tube 6 from a humidification apparatus and allow fluid flow through the inlet tube 364 in a first direction. In some embodiments, the outlet port 380 can be configured to receive an expiratory tube 4. In some examples, the outlet port 380 can be fluidly connected to the respiratory assistance system 1 to allow fluid flow through the outlet tube 384 in a second direction.

In some embodiments, the inlet tube 364 and the outlet tube 384 are configured to extend above and away from the patient. In some embodiments, the "over" and "under" design of the inlet tube 364 and the outlet tube 384 can help to reduce mass across the patient's face. In some examples, the inlet tube 364 and the outlet tube 384 can be more rigid so as to able to hold onto its shape without contacting the patient. The inlet tube 364 and outlet tube 384 can help to reduce the weight perceived by the patient by spreading out or increasing the distribution of forces from the interface and tubing, reducing patient discomfort. In some embodiments, the location of the inlet port 360 and the outlet port 380 can be alternated.

In some examples, the adaptor 300 can include a pressure tube 374 with a pressure port 370 and a pressure lumen 372 that is fluidly connected to the housing 320. As illustrated in FIGS. 4A-4B, the pressure tube 374 is located between the inlet tube 364 and outlet tube 384 and the pressure tube 374 is fluidly connected to a pressure line which is fluidly connected to the pressure regulating device 7.

As with the adaptor 100, in some embodiments, the adaptor 300 can include an integrated nozzle 322 that is configured to connect with an external device to provide a fluid connection with the inside of the housing 320. In some examples, the nozzle 322 can be fluidly connected to another conduit to isolate and restrict the mixing of the aerosolized material (for example, a drug) with the air flow coming through the inlet tube 364.

As illustrated in FIGS. 4C-4G, in some embodiments, the nozzle 322 can be fluidly connected to a surfactant tube 314. The surfactant tube 314 can have a surfactant port 310, an internal surfactant lumen 312, and a bifurcated portion 316. In some examples, the surfactant tube 314 can have a surfactant port 310 at a first end of the surfactant tube 314 that is configured to be fluidly connected to the respiratory assistance system 1 to allow the delivery of a substance, such as an aerosolized surfactant, through the housing 320 and to the patient through the patient interface 350.

In some embodiments, the surfactant tube 314 can be fluidly connected with an external device such as a medicament delivery device. In some embodiments, the medicament delivery device can be a nebulizer, a capillary aerosol generator, or a metered dose inhaler (MDI). A nebuliser such as a flow based nebuliser, for example, can deliver aerosolised surfactant to the patient. In some embodiments, a nebuliser can be configured to deliver a medicament or anaesthetic substance to the patient.

In some embodiments, the surfactant tube 314 can have a circular cross-section which ensures that the surfactant lumen 312 does not have any sharp edges so as to reduce deposition within the surfactant lumen 312. The surfactant tube 314 is not limited to a tubular shape, and can comprise any number of shapes. The surfactant port 310 of the surfactant tube 314 is located directly over the nose so as to reduce the deposition of medicament within the surfactant lumen 312 and ensure sufficient delivery of medicament to the patient.

The body of the adaptor 300 can be divided into a plurality of compartments. FIGS. 4C-4G illustrate the configuration of the adaptor 300 and the airflow through the inlet lumen 362, outlet lumen 382, surfactant lumen 312, pressure lumen 372, and the housing 320. The plurality of compartments within the adaptor 300 can reduce premixing of the medicament received through the surfactant port 310 and the inspiratory gases through the inlet lumen 362 and reduce dilution of the drug by the outgoing gases through the outlet port 380. In some examples, the arrangement of the conduits within the adaptor 300 can help to maximize gas flow to the patient. For example, inspiratory gases can enter the adaptor 300 through the inlet port 360 and flow through the inlet lumen 362 and into the housing 320. There, the gases can mix with the medicament delivered from the bifurcated portion 316 surfactant tube 314 near the opening of the nostril lumens 354. As illustrated in FIG. 4C, there is a gap between the end of the surfactant tube 314 and the nostril lumens 354 of the patient interface 350 that allow inspiratory gases to flow in. In some embodiments, the expiratory gases can then exit the patient interface 350 and move around the surfactant tube 314, flow through the outlet lumen 382, and exit the adaptor 300 from the outlet port 380.

FIGS. 5A-5G illustrate another embodiment of an adaptor 400. The adaptor 400 resembles or is identical to the adaptor 100 in many respects. Accordingly, the numerals used to identify components of the system for adaptor 100 are incremented by one hundred to identify like features of the adaptor 400. This number convention generally applies to the remainder of the Figures. Any component disclosed in any embodiment in this specification can be used in other embodiments.

Figure 5A:
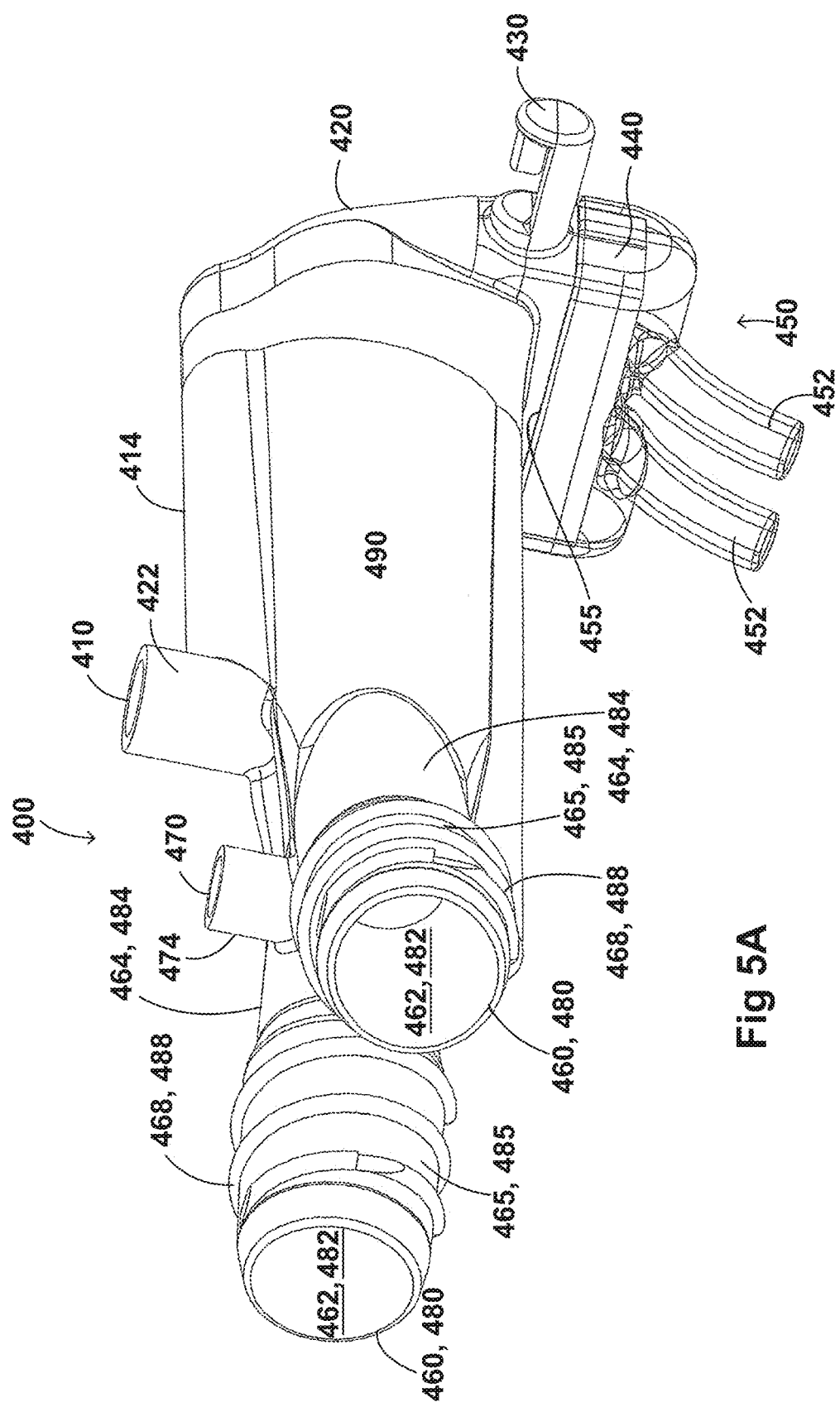
Figure 5B:
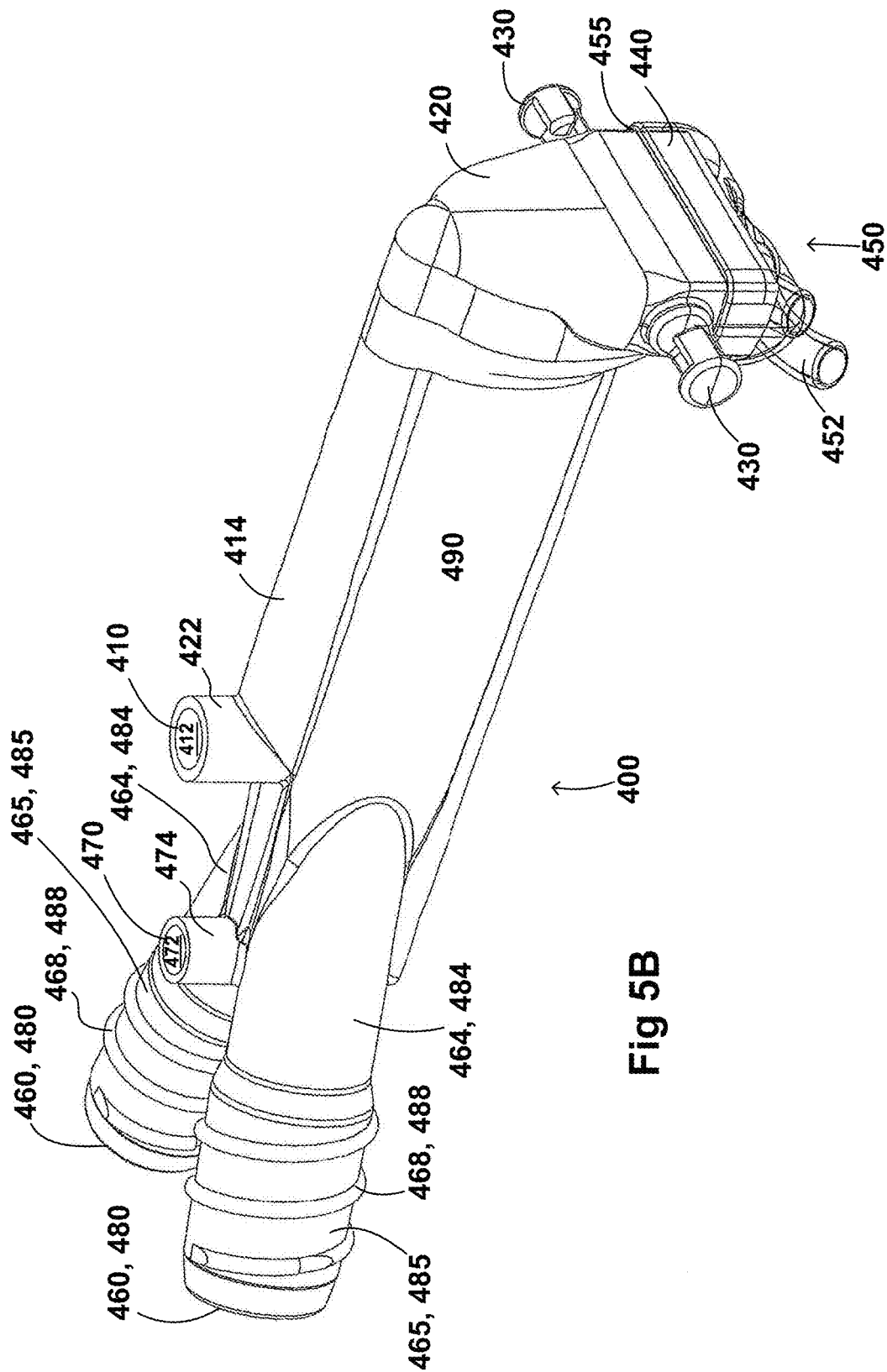

Turning first to FIGS. 5A and 5B, illustrated is an embodiment of the adaptor 400. Like the adaptor 100, the adaptor 400 can include a housing 420 that is fluidly connected to a plurality of conduits to provide fluid flow, such as air, and the delivery of aerosolized surfactants to the patient through the patient interface 450. The adaptor 400 can include a housing 420, a plurality of clips 430, an inlet port 460, an outlet port 480, a pressure port 470, a surfactant port 410 and a coupling surface 440 for engaging a patient interface 450. In some embodiments, the adaptor 400 is configured to have an oval tube oriented to present the smallest possible trunk width between the patient's (for example, the infant) eyes while maintaining a sufficient cross-section to provide sufficient air flow.

In some examples, as with the housing 120, the housing 420 can include a substantially hollow cylindrical body. The shape of the housing 420 can be optimized to reduce resistance to flow within the housing 420. In some examples, the housing 420 can comprise different shapes, for example, rectangular, square, hexagonal, or semi-circular. In some embodiments the shape of the housing 420 can minimize volume within the housing 420. This can reduce dead space—therefore reducing the build-up of carbon dioxide within the housing 420. The housing 420 can be compact so as to reduce the weight and bulk of the housing 420 and improve patient comfort. As discussed with regard to the adaptor 100, the housing 420 can be configured to both receive gases through an inspiratory tube and aid the exit of gases through an expiratory tube.

The housing 420 can include a coupling surface 440 at an end of the housing 420 that is proximate to the patient. As illustrated in FIGS. 5A-5B, the coupling surface 440 can be rectangular in cross-section. The coupling surface 440 can include a first end that is fluidly connected with the housing 420 and a second end that is configured to couple with the patient interface 450. The second end of the coupling surface 440 can allow fluid communication between the housing 420 and the patient interface 450. In some embodiments, a partial barrier can exist between the housing 420 and the first end of the coupling surface 440. An orifice can thus maintain fluid communication between the housing 420 and the patient interface 450. The orifice can direct the flow of gases toward the patient interface 450. In some examples, the orifice can control the pressure of the gas flow as it enters the patient interface 450.

In some embodiments, the patient interface 450 is similar if not identical to the patient interface 150 of adaptor 100. As discussed, the patient interface 450 can be configured to be removably coupled with the coupling surface 440. In some examples the patient interface 450 can be coupled with the coupling surface 440 using adhesives or mechanical mechanisms such as snap-fit mechanisms. In some embodiments, the patient interface 450 can be permanently attached to the coupling surface 440 using adhesives, snap-fit mechanisms, or welding techniques. FIGS. 5A-5G illustrate a patient interface 450 that is transparent so as to allow the engagement between the coupling surface 440 and the patient interface 450 to be visualized. The patient interface 450 can include a substantially hollow complementary region 455 that is configured to receive the coupling surface 440. In some embodiments, the coupling surface 440 can be configured to receive the complementary region 455 of the patient interface 450. In some embodiments, the patient interface 450 can be permanently coupled with the adaptor 400. This can provide a fully integrated adaptor which may improve the usability of the adaptor 400.

As illustrated in FIGS. 5A-5B, in some examples, the patient interface 450 can include nasal prongs 452. In some embodiments, the patient interface 450 can include respiratory interfaces such as, but not limited to, a nasal mask, oral mask, combined nasal and oral mask, tracheal mask, or nasal pillows. In some embodiments, the adaptor 400 can be adapted for use in a surgical application. The patient interface 450 can include a diffuser, trocar, or catheter.

In some embodiments, the adaptor 400 can include clips 430 that are positioned on first and second sides of the housing 420. As illustrated in FIGS. 5A-5B, the first and second sides of the coupling surface 440 can be substantially perpendicular to the first and second ends of the coupling surface 440. In some embodiments, the clips 430 can be configured to be mobile clips. For example, the clip 430 can be positioned on a slidable and/or rotatable bar or cord. In this way, the position of the clips 430 can be rotated or altered to simplify the attachment of the patient stabilising mechanism to the adaptor 400. In some embodiments, the clips 330 can be configured to permanently attach to an interface stabilising mechanism.

As discussed above, in some examples, the clips 430 can engage a removable attachment that is attached to an interface stabilising mechanism, such as headgear or a hat or bonnet. As described above, an example of the removable attachment is illustrated in FIGS. 13A and 13B.

In some embodiments, the adaptor 400 can include a plurality of conduits that act as the inlet and outlet of air flow that are located adjacent to each. In some embodiments, the plurality of conduits runs parallel to each other. As illustrated in FIGS. 5A and 5B, as the plurality of conduits are located adjacent to each other, the inlet port 460 and the outlet port 480 are interchangeable and can be located on either side of the housing 420.

In some examples, the adaptor 400 can include an inlet port 460 that can be fluidly connected to an inspiratory tube 6 from a humidification apparatus and allow fluid flow through the inlet tube 464 in a first direction. In some embodiments, the inlet tube 464 can include an engagement portion 465 at a first end that engages with the inspiratory tube 6. In some embodiments, the inlet tube 464 is secured to the inspiratory tube 6 using a securing portion 468. The securing portion 468 can allow the inlet tube 464 to be removably attached to the inspiratory tube 6. For example, as illustrated in FIGS. 4A and 4B, the securing portion 468 can be threaded and configured to engage internal threading located on a portion of the inspiratory tube 6. However, the securing portion 468 can come in any shape and size, such as a tab, latch, or any locking feature that has a complementary securing portion on the inspiratory tube 6. In some embodiments, the securing portion securing portion 468 can allow the adaptor 400 to be directly attached to the respiratory assistance system 1. This can help, for example, to reduce the number of parts in the respiratory assistance system 1 as well as reduce the manufacturing costs.

In some embodiments, the outlet port 480 can be configured to receive an expiratory tube 4. In some examples, the outlet port 480 can be fluidly connected to the respiratory assistance system 1 to allow fluid flow through the outlet tube 484 in a second direction. The outlet tube 484 can include an engagement portion 465 at a first end that engages with the expiratory tube 4. In some embodiments, the outlet tube 484 can be secured to the expiratory tube 4 using a securing portion 488. The securing portion 488 can allow the outlet tube 484 to be removably attached to the expiratory tube 4. For example, as illustrated in FIGS. 5A and 5B, the securing portion 488 can be threaded and configured to engage internal threading located on a portion of the expiratory tube 4. However, the securing portion 488 can come in any shape and size, such as a latch, threaded portion, or any locking feature that has a complementary securing portion on the expiratory tube 4. As was discussed with regard to the securing portion 468, in some embodiments, the securing portion 488 can allow the adaptor 400 to be directly attached to the respiratory assistance system 1. This can help, for example, to reduce the number of parts in the respiratory assistance system 1 as well as reduce the manufacturing costs.

In some examples, the inlet tube 464 and the outlet tube 484 are configured to extend above and away from the patient. As with the adaptor 300, the adaptor 400 retains the narrow body of the "over" and "under" design, but, as mentioned above, the connectors are now side-by-side so connections are interchangeable. As discussed, with regard to the adaptor 300, this design of the inlet tube 464 and the outlet tube 484 can help to reduce the mass across the patient's face. In some examples, the inlet tube 464 and the outlet tube 484 can be more rigid so as to be able to hold onto its shape without contacting the patient. The inlet tube 464 and the outlet tube 484 can help to reduce the weight perceived by the patient by spreading out or increasing the distribution of forces from the interface and tubing, reducing patient discomfort. In some embodiments, the location of the inlet port 460 and the outlet port 480 can be alternated.

Figure 5C:
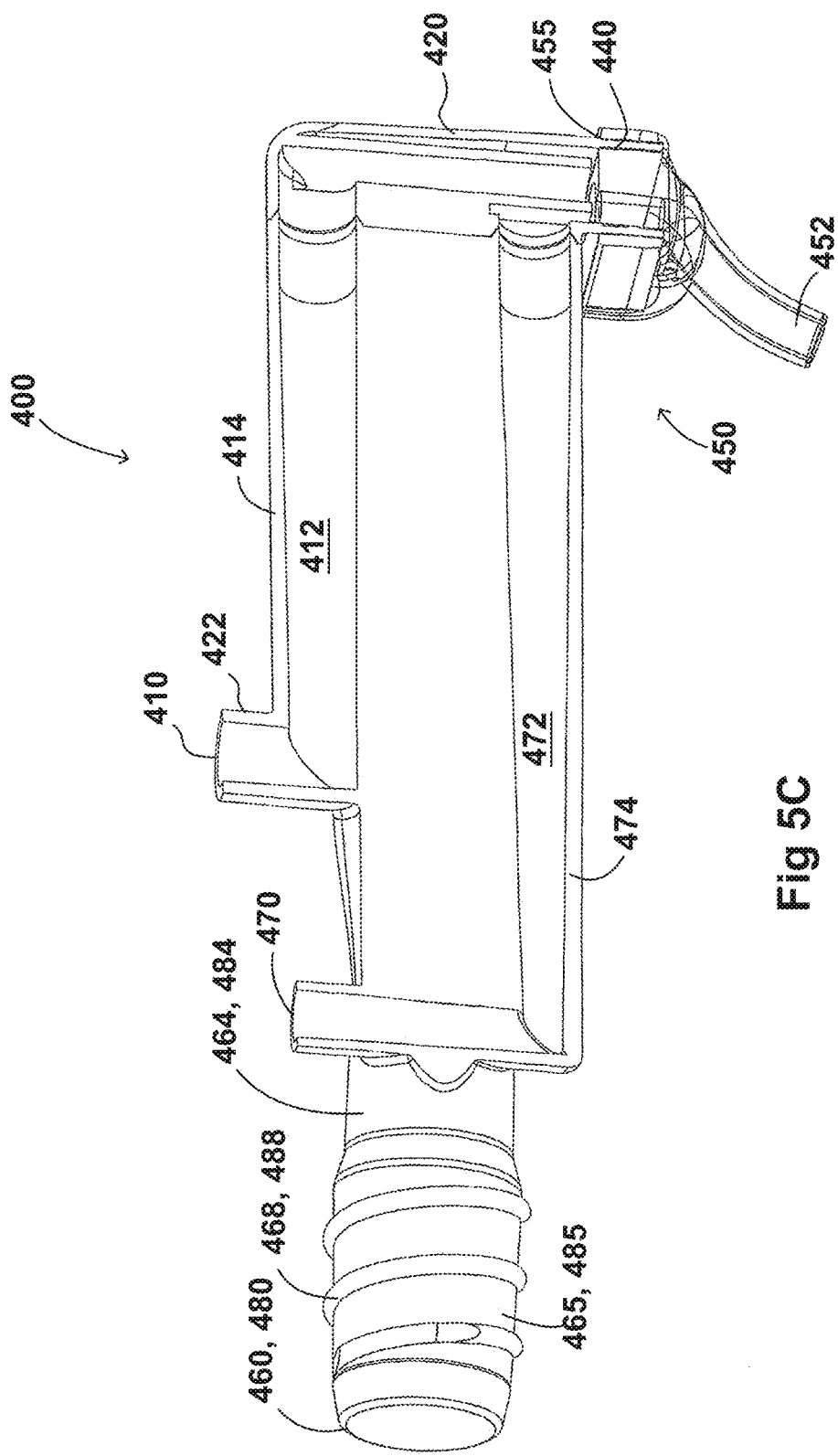
Figure 5D:
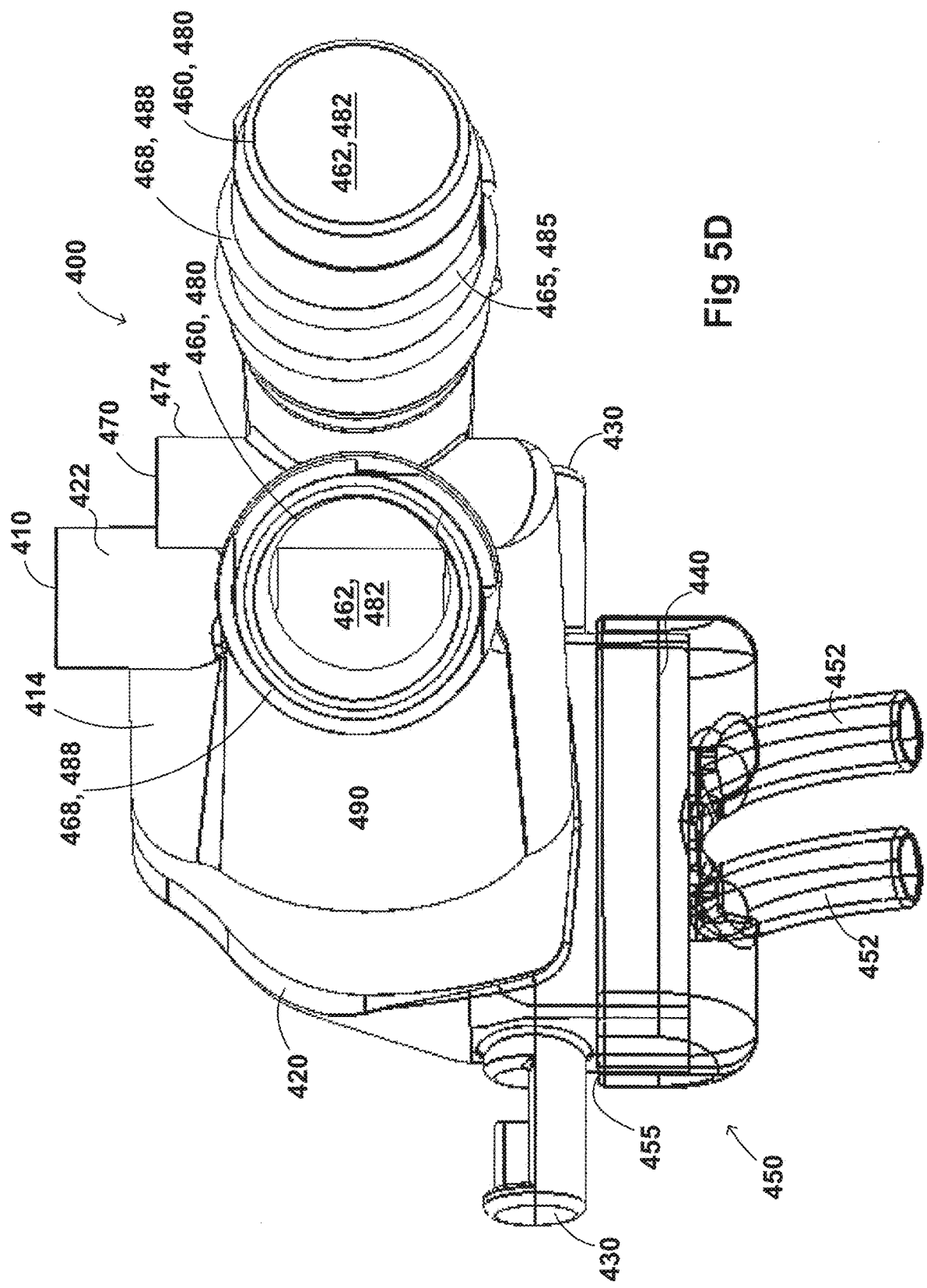
Figure 5E:
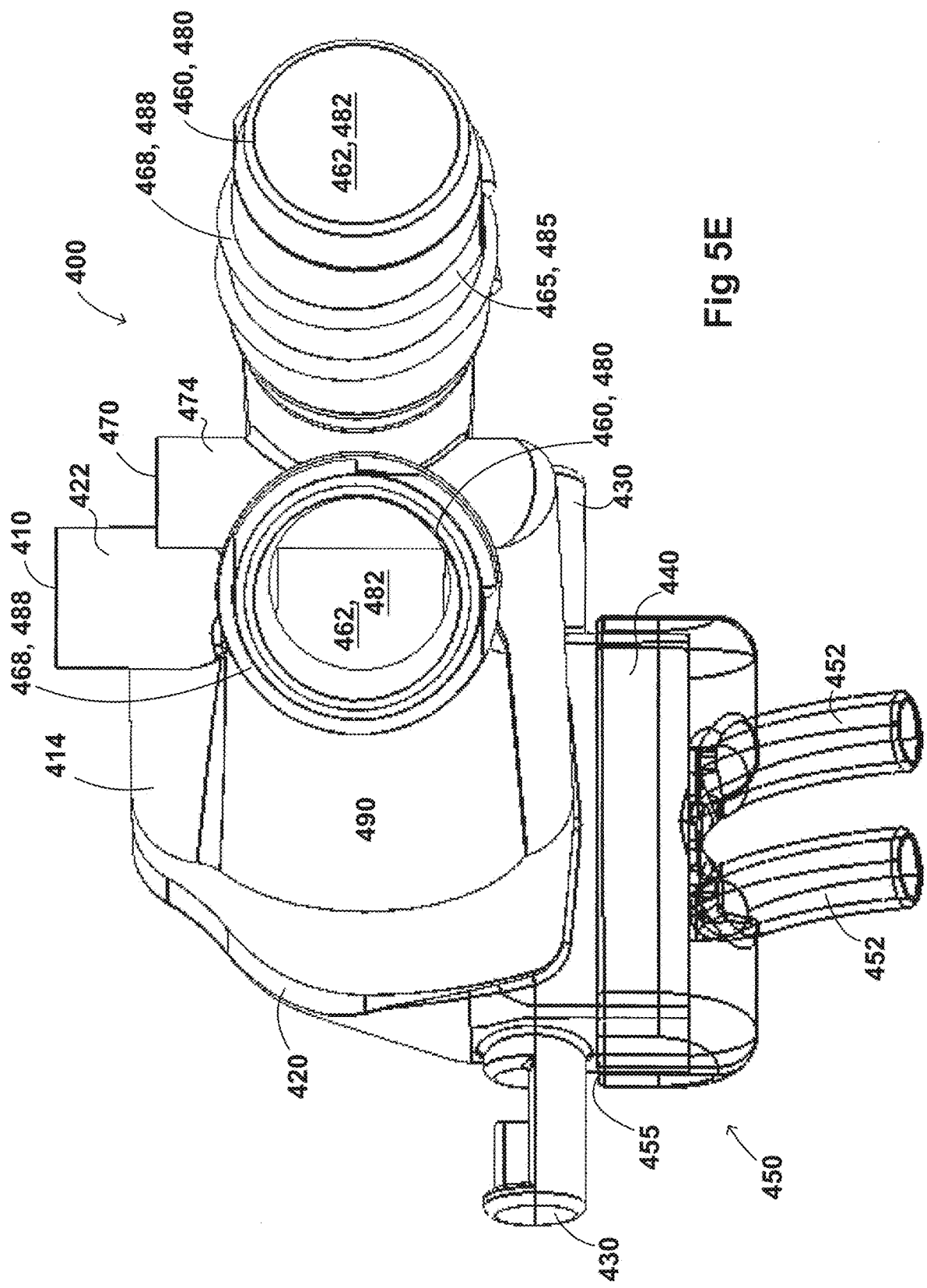
Figure 5F:
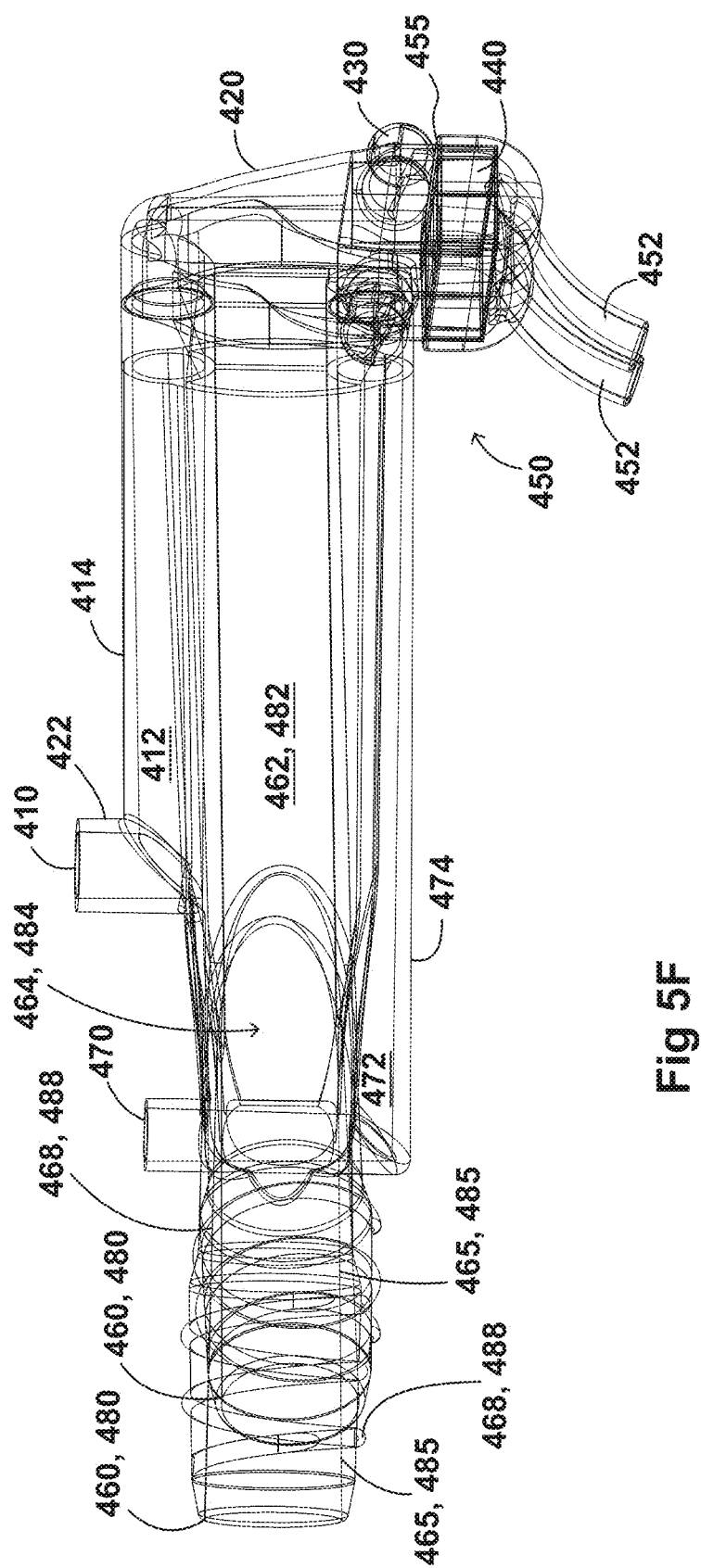
Figure 5G:
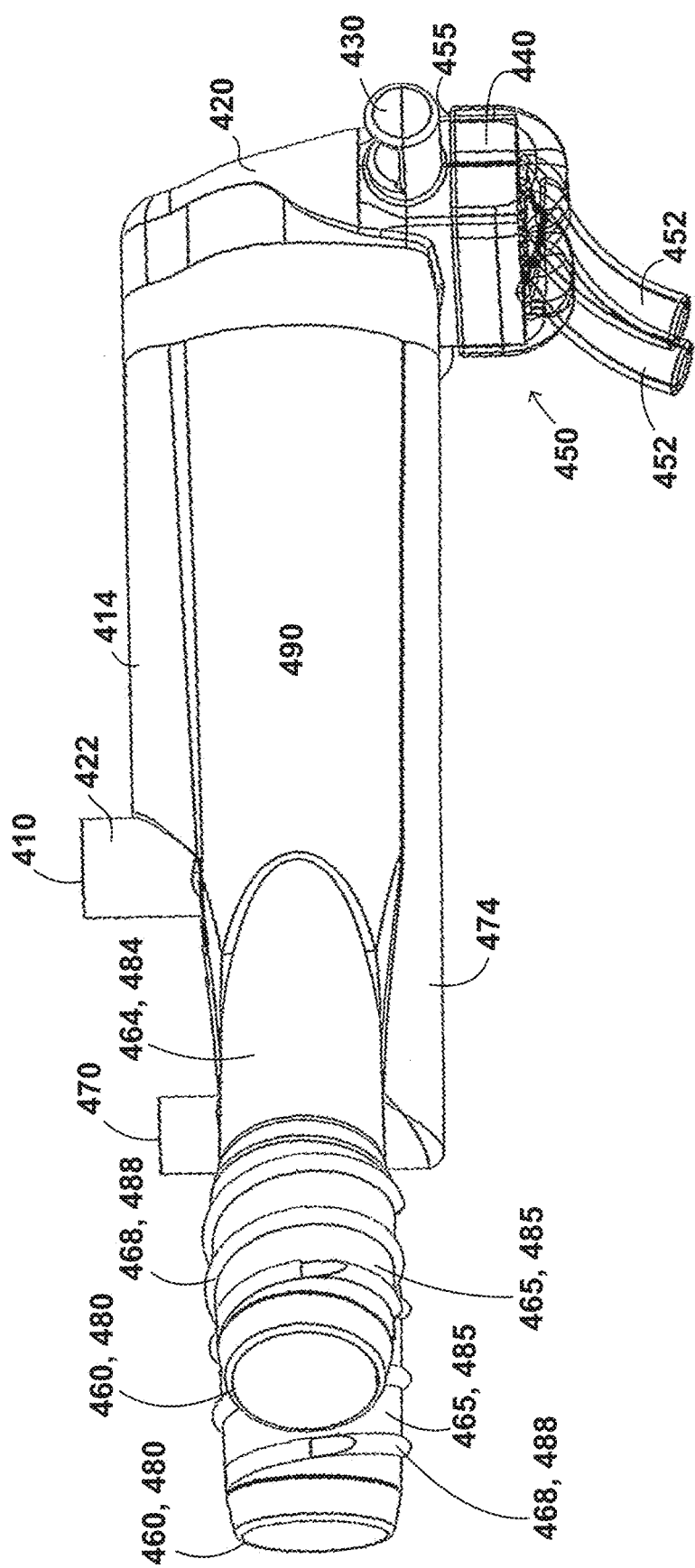

In some examples, the adaptor 400 can include a pressure tube 474 with a pressure port 470 and a pressure lumen 472 that is fluidly connected to the housing 420. As illustrated in FIG. 5C, the pressure tube 474 extends above the pair of conduits (the inlet port 460 and the outlet port 480) such that the pressure port 470 is directed away from the face of the patient. The pressure tube 474 can generally extend vertically between the inlet port 460 and outlet port 480 before making an approximately right angle turn towards the housing 420 such that the pressure lumen 472 extends between the inlet port 460 and outlet port 480 on the side of the adaptor 400 closest to the patient. In some embodiments, the pressure lumen 472 extends towards the housing 420 such that the pressure port 470 and pressure lumen 472 are fluidly connected to the housing 420. In some embodiments, the pressure tube 474 is fluidly connected to a pressure line which is fluidly connected to the pressure regulating device 7.

As with the adaptor 100, in some embodiments, the adaptor 400 can include nozzle 422 that is configured to connect with an external device to provide a fluid connection with the inside of the housing 420. In some examples, the nozzle 422 can be fluidly connected to another conduit to isolate and restrict the mixing of the aerosolized material (for example, a drug) with the air flow coming through the inlet tube 464.

As illustrated in FIGS. 5C-5G, in some embodiments, the nozzle 422 can be fluidly connected to a surfactant tube 414. The surfactant tube 414 can have a surfactant port 410 and a surfactant lumen 412. As shown in FIG. 5C, the surfactant port 410 is located closer to the patient's forehead and is closer to the housing 420 than the pressure port 470. In some embodiments, the surfactant tube 414 extends above the pair of conduits (the inlet port 460 and the outlet port 480) such that the surfactant port 410 is directed away from the face of the patient. The surfactant tube 414 can make an approximately right turn towards the housing 420. In some examples, the surfactant lumen 412 can extend towards the housing 420 between the inlet port 460 and pressure port 470 such that the surfactant tube 414 is on the side of the adaptor 400 furthest away from the patient. In some embodiments, the surfactant lumen 412 extends towards the housing 420 such that the surfactant port 410 and the surfactant lumen 412 are fluidly connected to the housing 420.

In some examples, the surfactant tube 414 can have a surfactant port 410 at a first end of the surfactant tube 414 that is configured to be fluidly connected to the respiratory assistance system 1 to allow the delivery of a substance, such as an aerosolized surfactant, through the housing 420 and to the patient through the patient interface 450.

In some embodiments, the surfactant tube 414 can be fluidly connected with an external device such as a medicament delivery device. In some embodiments, the medicament delivery device can be a nebulizer, a capillary aerosol generator, or a metered dose inhaler (MDI). A nebuliser such as a flow based nebuliser, for example, can deliver aerosolised surfactant to the patient. In some embodiments, a nebuliser can be configured to deliver a medicament or anaesthetic substance to the patient.

In some embodiments, the surfactant tube 414 can have a circular cross-section which ensures that the surfactant lumen 412 does not have any sharp edges so as to reduce deposition within the surfactant lumen 412. The surfactant tube 414 is not limited to a tubular shape, and can comprise any number of shapes. The surfactant port 410 of the surfactant tube 414 is located directly over the nose so as to reduce the deposition of medicament within the surfactant lumen 412 and ensure sufficient delivery of medicament to the patient.

The body of the adaptor 400 can be divided into a plurality of compartments. FIGS. 5C-5G illustrate the configuration of the adaptor 400 and the airflow through the tubular body 490, surfactant lumen 412, pressure lumen 472, and the housing 420. As illustrated in FIGS. 5C-5G, the tubular body 490 can be divided into an inlet lumen 462 and an outlet lumen 482. The plurality of compartments within the adaptor 400 can reduce premixing of the medicament received through the surfactant port 410 and the inspiratory gases through the inlet lumen 462 and reduce dilution of the drug by the outgoing gases through the outlet port 480. In some examples, the arrangement of the conduits within the adaptor 400 can help to maximize gas flow to the patient. For example, inspiratory gases can enter the adaptor 400 through the inlet port 460 and flow through the inlet lumen 462 and into the housing 420. There, the gases can mix with the medicament delivered from the surfactant tube 414 near the opening of the nostril lumens (not pictured). As illustrated in FIG. 5C, there is a gap between the end of the surfactant tube 414 and the nostril lumens (not illustrated) of the patient interface 450 that allow inspiratory gases to flow in. In some embodiments, the expiratory gases can then exit the patient interface 450 and move around the surfactant tube 414, flow through the outlet lumen 482, and exit the adaptor 400 from the outlet port 480.

FIGS. 6A-6I illustrate another embodiment of an adaptor 500. The adaptor 500 resembles or is identical to the adaptor 100 in many respects. Accordingly, the numerals used to identify components of the system for adaptor 100 are incremented by one hundred to identify like features of the adaptor 500. This number convention generally applies to the remainder of the Figures. Any component disclosed in any embodiment in this specification can be used in other embodiments. In some embodiments, the adaptor 500 is configured to have an oval tube oriented to present the smallest possible trunk width between the patient's (for example, the infant) eyes while maintaining a sufficient cross-section to provide sufficient air flow.

Figure 6B:
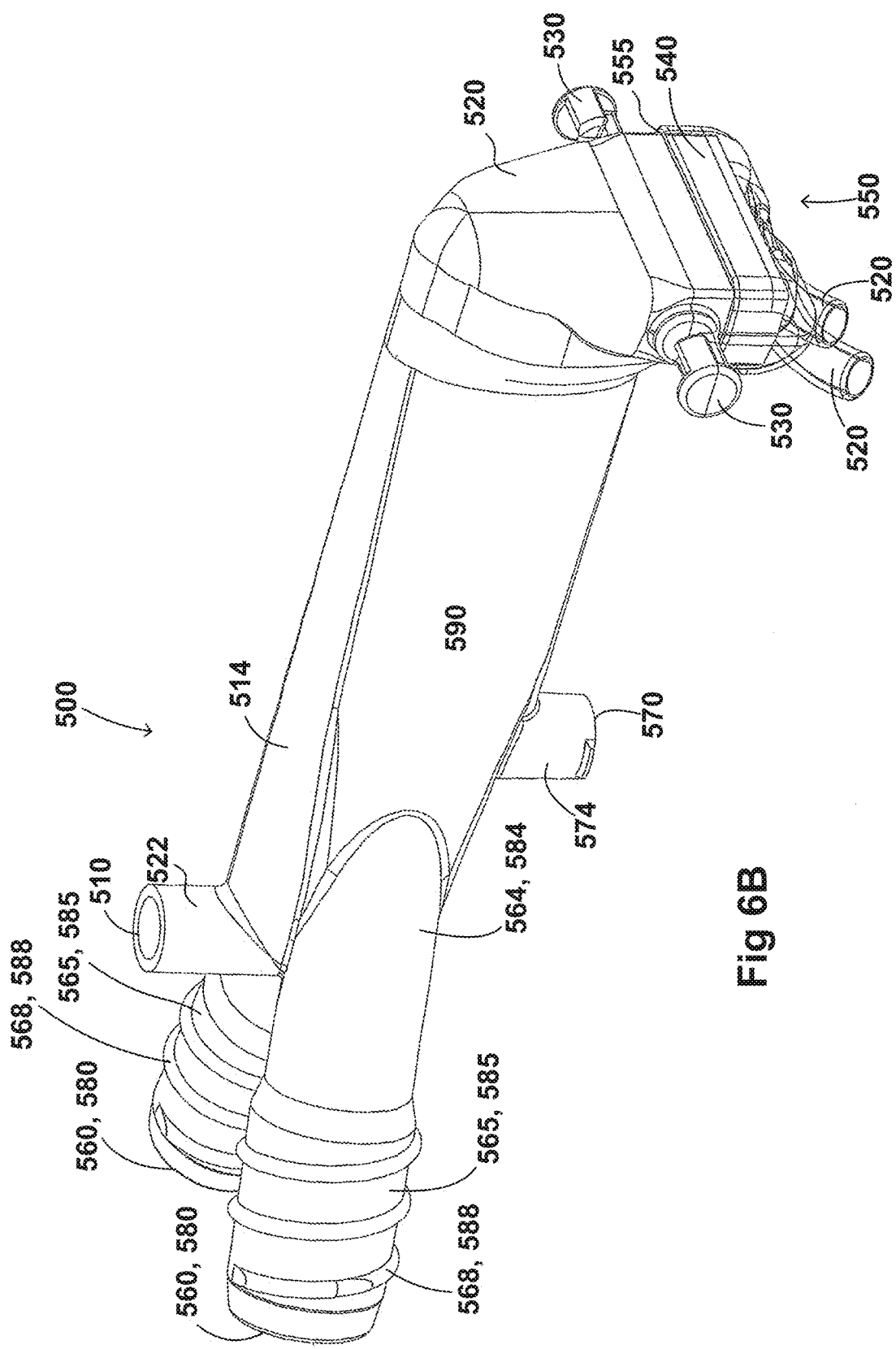

Turning first to FIGS. 6A and 6B, illustrated is an embodiment of the adaptor 500. Like the adaptor 100, the adaptor 500 can include a housing 520 that is fluidly connected to a plurality of conduits to provide fluid flow, such as air, and the delivery of aerosolized surfactants to the patient through the patient interface 550. The adaptor 500 can include a housing 520, a plurality of clips 530, an inlet port 560, an outlet port 580, a pressure port 570, a surfactant port 510 and a coupling surface 540 for engaging a patient interface 550.

In some examples, as with the housing 120, the housing 520 can include a substantially hollow cylindrical body. The shape of the housing 520 can be optimized to reduce resistance to flow within the housing 520. In some examples, the housing 520 can comprise different shapes, for example, rectangular, square, hexagonal, or semi-circular. In some embodiments the shape of the housing 520 can minimize volume within the housing 520. This can reduce dead space—therefore reducing the build-up of carbon dioxide within the housing 520. The housing 520 can be compact so as to reduce the weight and bulk of the housing 520 and improve patient comfort. As discussed with regard to the adaptor 100, the housing 520 can be configured to both receive gases through an inspiratory tube and aid the exit of gases through an expiratory tube.

The housing 520 can include a coupling surface 540 at an end of the housing 520 that is proximate to the patient. As illustrated in FIGS. 6A-6B, the coupling surface 540 can be rectangular in cross-section. The coupling surface 540 can include a first end that is fluidly connected with the housing 520 and a second end that is configured to couple with the patient interface 550. The second end of the coupling surface 540 can allow fluid communication between the housing 520 and the patient interface 550. In some embodiments, a partial barrier can exist between the housing 520 and the first end of the coupling surface 540. An orifice can thus maintain fluid communication between the housing 520 and the patient interface 550. The orifice can direct the flow of gases toward the patient interface 550. In some examples, the orifice can control the pressure of the gas flow as it enters the patient interface 550.

In some embodiments, the patient interface 550 is similar if not identical to the patient interface 150 of adaptor 100. As discussed, the patient interface 550 can be configured to be removably coupled with the coupling surface 540. In some examples the patient interface 550 can be coupled with the coupling surface 540 using adhesives or mechanical mechanisms such as snap-fit mechanisms. In some embodiments, the patient interface 550 can be permanently attached to the coupling surface 540 using adhesives, snap-fit mechanisms, or welding techniques. FIGS. 6A-6I illustrate a patient interface 550 that is transparent so as to allow the engagement between the coupling surface 540 and the patient interface 550 to be visualized. The patient interface 550 can include a substantially hollow complementary region 555 that is configured to receive the coupling surface 540. In some embodiments, the coupling surface 540 can be configured to receive the complementary region 555 of the patient interface 550. In some embodiments, the patient interface 550 can be permanently coupled with the adaptor 500. This can provide a fully integrated adaptor which may improve the usability of the adaptor 500.

As illustrated in FIGS. 6A-6B, in some examples, the patient interface 550 can include nasal prongs 552. In some embodiments, the patient interface 550 can include respiratory interfaces such as, but not limited to, a nasal mask, oral mask, combined nasal and oral mask, tracheal mask, or nasal pillows. In some embodiments, the adaptor 500 can be adapted for use in a surgical application. The patient interface 550 can include a diffuser, trocar, or catheter.

In some embodiments, the adaptor 500 can include clips 530 that are positioned on first and second sides of the housing 520. As illustrated in FIGS. 6A-6B, the first and second sides of the coupling surface 540 can be substantially perpendicular to the first and second ends of the coupling surface 540. In some embodiments, the clips 530 can be configured to be mobile clips. For example, the clip 530 can be positioned on a slidable and/or rotatable bar or cord. In this way, the position of the clips 530 can be rotated or altered to simplify the attachment of the patient stabilising mechanism to the adaptor 500. In some embodiments, the clips 530 can be configured to permanently attach to an interface stabilising mechanism.

As discussed above, in some examples, the clips 530 can engage a removable attachment that is attached to an interface stabilising mechanism, such as headgear or a hat or bonnet. As described above, an example of the removable attachment is illustrated in FIGS. 13A and 13B.

In some embodiments, the adaptor 500 can include a plurality of conduits that act as the inlet and outlet of air flow that are located adjacent to each. In some embodiments, the plurality of conduits runs parallel to each other. As illustrated in FIGS. 6A and 6B, as the plurality of conduits are located adjacent to each other, the inlet port 560 and the outlet port 580 are interchangeable and can be located on either side of the housing 520.

In some examples, the adaptor 500 can include an inlet port 560 that can be fluidly connected to an inspiratory tube 6 from a humidification apparatus and allow fluid flow through the inlet tube 564 in a first direction. In some embodiments, the inlet tube 564 can include an engagement portion 565 at a first end that engages with the inspiratory tube 6. In some embodiments, the inlet tube 564 is secured to the inspiratory tube 6 using a securing portion 568. The securing portion 568 can allow the inlet tube 564 to be removably attached to the inspiratory tube 6. For example, as illustrated in FIGS. 6A and 6B, the securing portion 568 can be threaded and configured to engage internal threading located on a portion of the inspiratory tube 6. However, the securing portion 568 can come in any shape and size, such as a tab, latch, or any locking feature that has a complementary securing portion on the inspiratory tube 6. In some embodiments, the securing portion 568 can allow the adaptor 500 to be directly attached to the respiratory assistance system 1. This can help, for example, to reduce the number of parts in the respiratory assistance system 1 as well as reduce the manufacturing costs.

In some embodiments, the outlet port 580 can be configured to receive an expiratory tube 4. In some examples, the outlet port 580 can be fluidly connected to the respiratory assistance system 1 to allow fluid flow through the outlet tube 584 in a second direction. The outlet tube 584 can include an engagement portion 565 at a first end that engages with the expiratory tube 4. In some embodiments, the outlet tube 584 can be secured to the expiratory tube 4 using a securing portion 588. The securing portion 588 can allow the outlet tube 584 to be removably attached to the expiratory tube 4. For example, as illustrated in FIGS. 6A and 6B, the securing portion 588 can be threaded and configured to engage internal threading located on a portion of the expiratory tube 4. However, the securing portion 588 can come in any shape and size, such as a latch, threaded portion, or any locking feature that has a complementary securing portion on the expiratory tube 4. As was discussed with regard to the securing portion 568, in some embodiments, the securing portion 588 can allow the adaptor 500 to be directly attached to the respiratory assistance system 1. This can help, for example, to reduce the number of parts in the respiratory assistance system 1 as well as reduce the manufacturing costs.

In some examples, the inlet tube 564 and the outlet tube 584 are configured to extend above and away from the patient. As with the adaptor 300 and adaptor 400, the adaptor 500 retains the narrow body of the "over" and "under" design, but, as mentioned above, the connectors are now side-by-side so connections are interchangeable. As discussed, with regard to the adaptor 500, this design of the inlet tube 564 and the outlet tube 584 can help to reduce the mass across the patient's face. In some examples, the inlet tube 564 and the outlet tube 584 can be more rigid so as to be able to hold onto its shape without contacting the patient. The inlet tube 564 and the outlet tube 584 can help to reduce the weight perceived by the patient by spreading out or increasing the distribution of forces from the interface and tubing, reducing patient discomfort. In some embodiments, the location of the inlet port 560 and the outlet port 580 can be alternated.

Figure 6C:
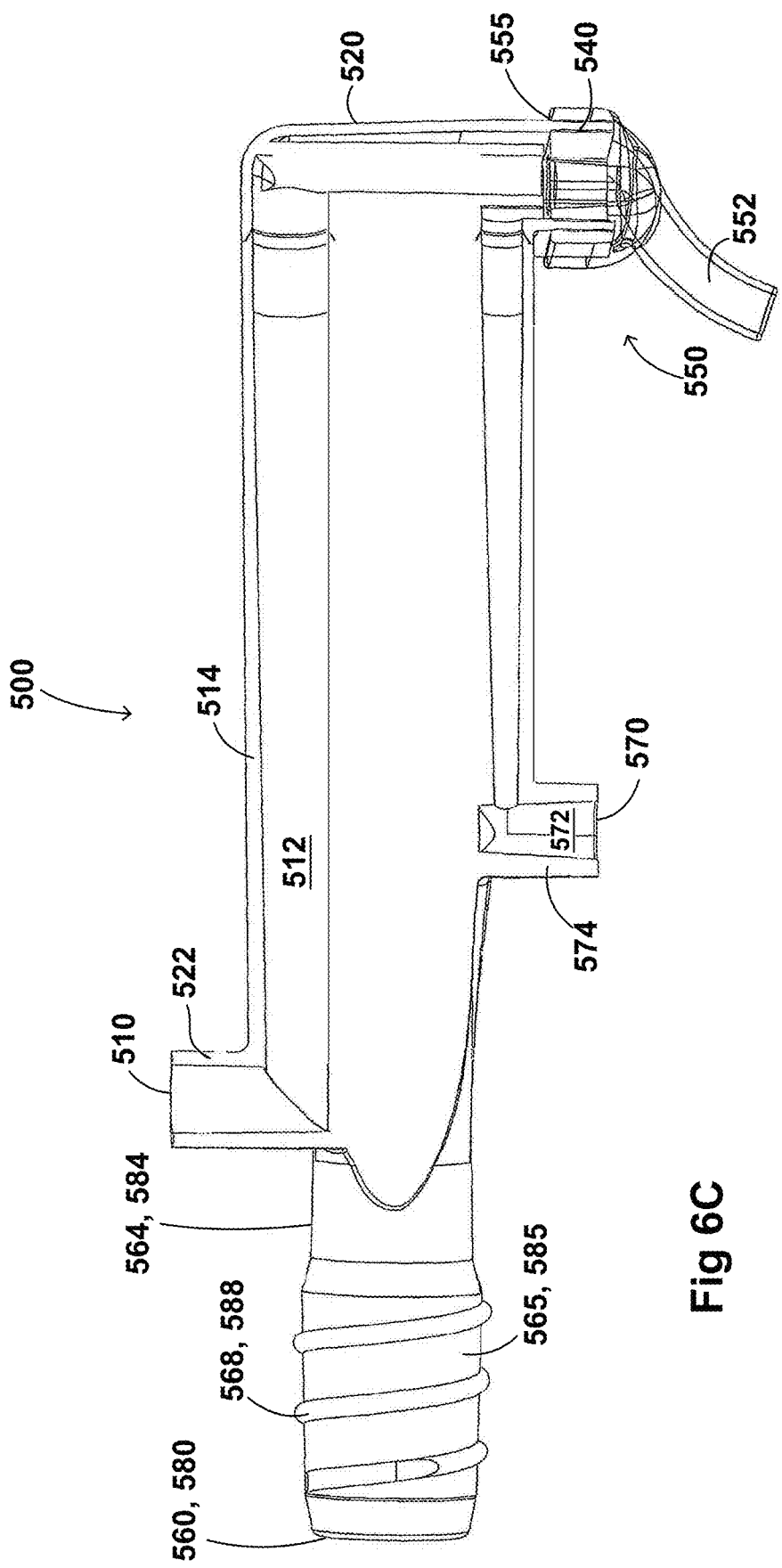
Figure 6F:
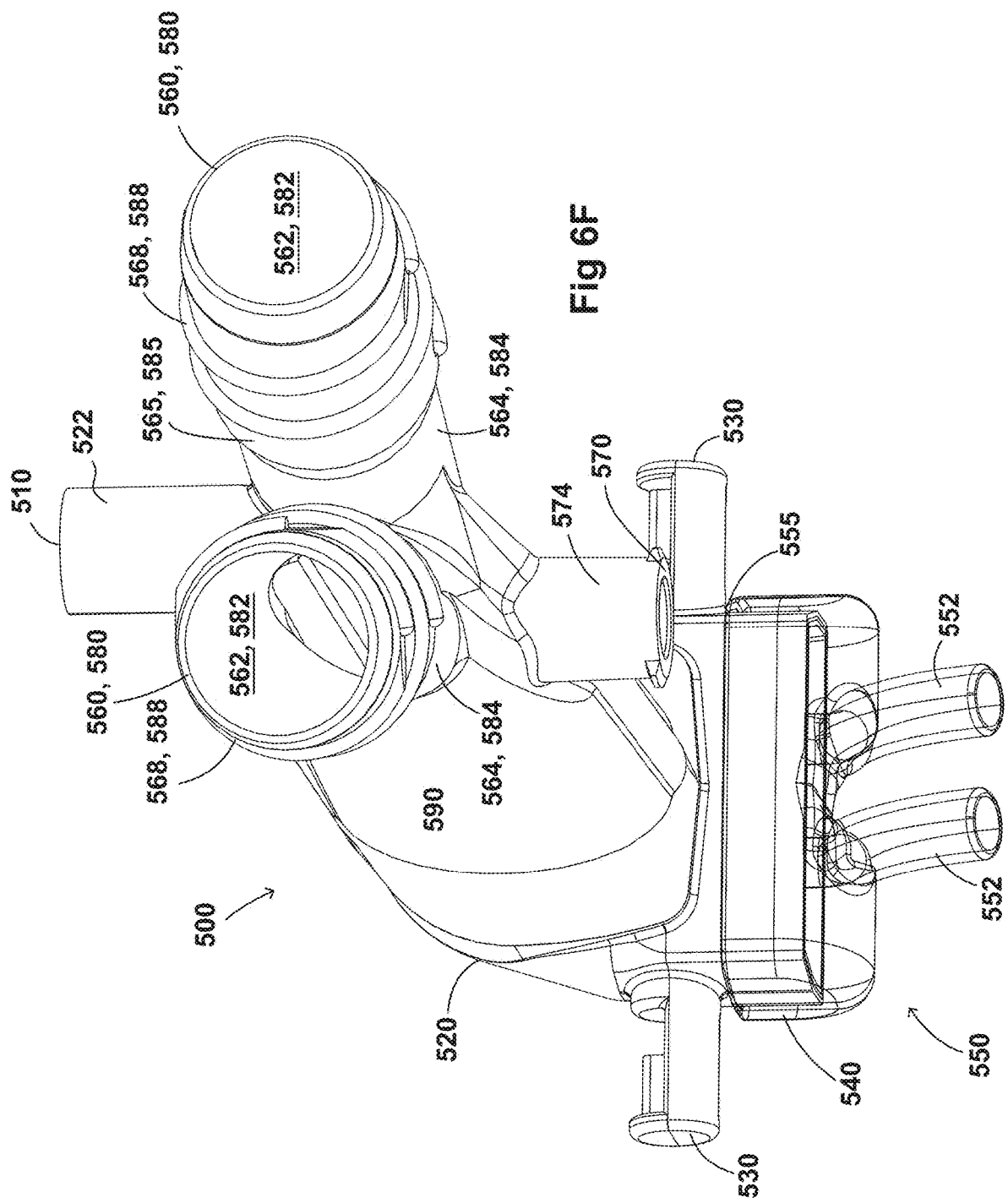
Figure 6H:
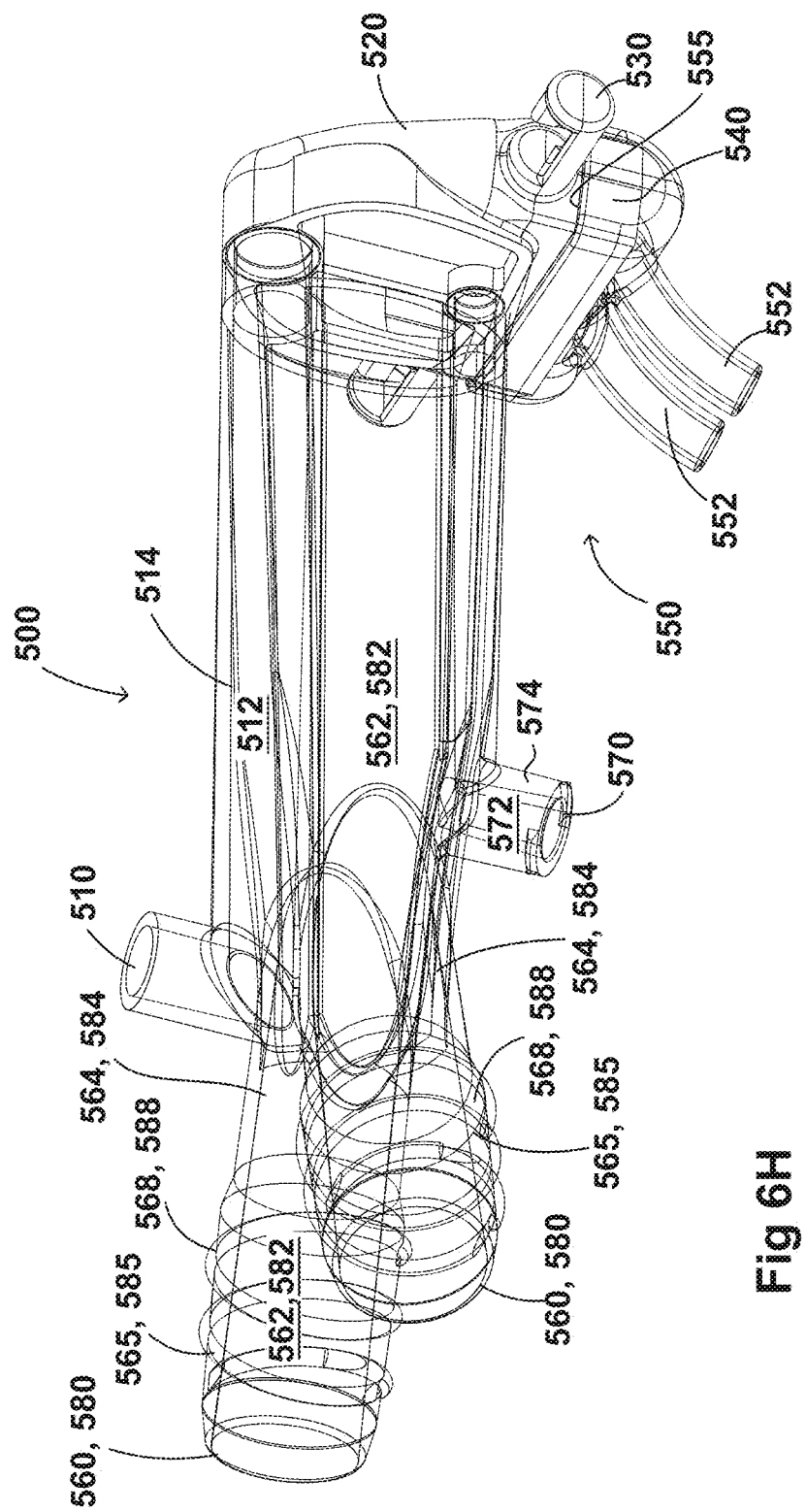
Figure 6I:
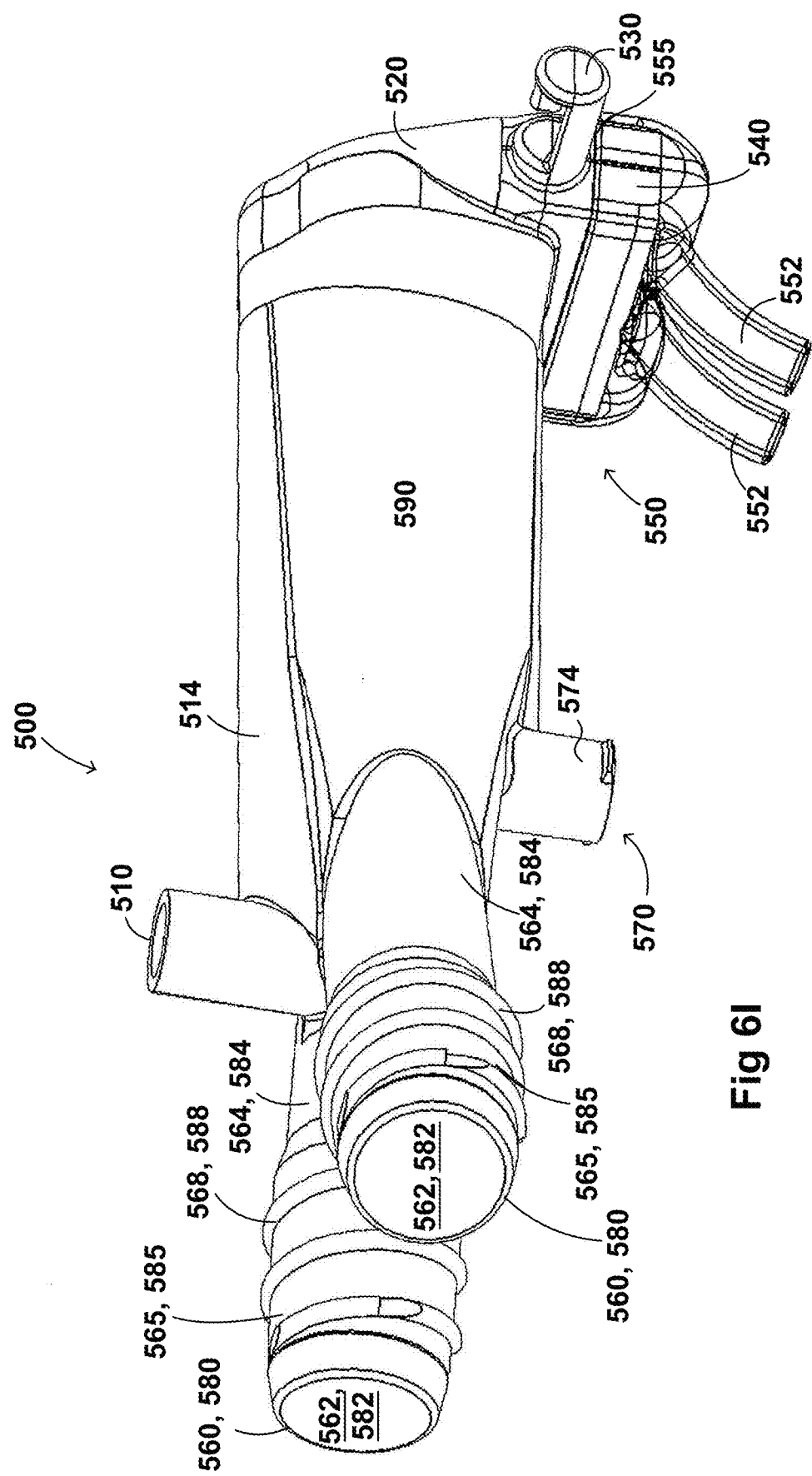

In some examples, the adaptor 500 can include a pressure tube 574 with a pressure port 570 and a pressure lumen 572 that is fluidly connected to the housing 520. As illustrated in FIG. 6C, the pressure tube 574 extends below the pair of conduits (the inlet port 560 and the outlet port 580) such that the pressure port 570 is directed towards the face of the patient. In some embodiments, the pressure port 570 is adjacent to and faces the patient's face. In order to protect the patient's face, the pressure port 570 can protrude into and be retained into a foam block.

The disclosed adaptors can be retained and stabilized on the patient's head. Examples of these retention and stabilization structures are disclosed in Applicant's U.S. application Ser. No. 10/242,903, filed on Sep. 13, 2002, that is hereby incorporated by reference.

The pressure tube 574 can generally extend vertically between the inlet port 560 and outlet port 580 before making an approximately right angle turn towards the housing 520 such that the pressure lumen 572 extends between the inlet port 560 and outlet port 580 on the side of the adaptor 500 closest to the patient. In some embodiments, the pressure lumen 572 extends towards the housing 520 such that the pressure port 570 and pressure lumen 572 are fluidly connected to the housing 520. In some embodiments, the pressure tube 574 is fluidly connected to a pressure line which is fluidly connected to the pressure regulating device 7.

As with the adaptor 100, in some embodiments, the adaptor 500 can include nozzle 522 that is configured to connect with an external device to provide a fluid connection with the inside of the housing 520. In some examples, the nozzle 522 can be fluidly connected to another conduit to isolate and restrict the mixing of the aerosolized material (for example, a drug) with the air flow coming through the inlet tube 564.

As illustrated in FIGS. 6C-6I, in some embodiments, the nozzle 522 can be fluidly connected to a surfactant tube 514. The surfactant tube 514 can have a surfactant port 510 and a surfactant lumen 512. As shown in FIG. 6C, the surfactant port 510 is located closer to the patient's forehead and is closer to the housing 520 than the pressure port 570. In some embodiments, the surfactant tube 514 extends above the pair of conduits (the inlet port 560 and the outlet port 580) such that the surfactant port 510 is directed away from the face of the patient. The surfactant tube 514 can make an approximately right turn towards the housing 520. In some examples, the surfactant lumen 512 can extend towards the housing 520 between the inlet port 560 and pressure port 570 such that the surfactant tube 514 is on the side of the adaptor 500 furthest away from the patient. In some embodiments, the surfactant lumen 512 extends towards the housing 520 such that the surfactant port 510 and the surfactant lumen 512 are fluidly connected to the housing 520.

In some examples, the surfactant tube 514 can have a surfactant port 510 at a first end of the surfactant tube 514 that is configured to be fluidly connected to the respiratory assistance system 1 to allow the delivery of a substance, such as an aerosolized surfactant, through the housing 520 and to the patient through the patient interface 550.

In some embodiments, the surfactant tube 514 can be fluidly connected with an external device such as a medicament delivery device. In some embodiments, the medicament delivery device can be a nebulizer, a capillary aerosol generator, or a metered dose inhaler (MDI). A nebuliser such as a flow based nebuliser, for example, can deliver aerosolised surfactant to the patient. In some embodiments, a nebuliser can be configured to deliver a medicament or anaesthetic substance to the patient.

In some embodiments, the surfactant tube 514 can have a circular cross-section which ensures that the surfactant lumen 512 does not have any sharp edges so as to reduce deposition within the surfactant lumen 512. The surfactant tube 514 is not limited to a tubular shape, and can comprise any number of shapes. The surfactant port 510 of the surfactant tube 514 is located directly over the nose so as to reduce the deposition of medicament within the surfactant lumen 512 and ensure sufficient delivery of medicament to the patient.

In contrast to the adaptor 400, the surfactant port 510 and the pressure port 570 extend from opposing sides of the adaptor 500. The surfactant port 510 and the pressure port 570 directing from opposing side of the adaptor 500 helps to avoid confusion and entanglement of the surfactant port 510 and the pressure port 570.

The body of the adaptor 500 can be divided into a plurality of compartments. FIGS. 6C-6I illustrate the configuration of the adaptor 500 and the airflow through the tubular body 590, surfactant lumen 512, pressure lumen 572, and the housing 520. As illustrated in FIGS. 6C-6I, the tubular body 590 can be divided into an inlet lumen 562 and an outlet lumen 582. The plurality of compartments within the adaptor 500 can reduce premixing of the medicament received through the surfactant port 510 and the inspiratory gases through the inlet lumen 562 and reduce dilution of the drug by the outgoing gases through the outlet port 580. In some examples, the arrangement of the conduits within the adaptor 500 can help to maximize gas flow to the patient. For example, inspiratory gases can enter the adaptor 500 through the inlet port 560 and flow through the inlet lumen 562 and into the housing 520. There, the gases can mix with the medicament delivered from the surfactant tube 514 near the opening of the nostril lumens (not pictured). As illustrated in FIG. 6C, there is a gap between the end of the surfactant tube 514 and the nostril lumens (not illustrated) of the patient interface 550 that allow inspiratory gases to flow in. In some embodiments, the expiratory gases can then exit the patient interface 550 and move around the surfactant tube 514, flow through the outlet lumen 582, and exit the adaptor 500 from the outlet port 580.

FIGS. 7A-7G illustrate another embodiment of an adaptor 600. The adaptor 600 resembles or is identical to the adaptor 100 in many respects. Accordingly, the numerals used to identify components of the system for adaptor 100 are incremented by one hundred to identify like features of the adaptor 600. This number convention generally applies to the remainder of the Figures. Any component disclosed in any embodiment in this specification can be used in other embodiments. In some embodiments, the adaptor 600 is configured to have an oval tube oriented to present the smallest possible trunk width between the patient's (for example, the infant) eyes while maintaining a sufficient cross-section to provide sufficient air flow.

Turning first to FIGS. 7A and 7B, illustrated is an embodiment of the adaptor 600. Like the adaptor 100, the adaptor 600 can include a housing 620 that is fluidly connected to a plurality of conduits to provide fluid flow, such as air, and the delivery of aerosolized surfactants to the patient through the patient interface 650. The adaptor 600 can include a housing 620, a plurality of clips 630, an inlet port 660, an outlet port 680, a pressure port 670, a surfactant port 610 and a coupling surface 640 for engaging a patient interface 650.

In some examples, as with the housing 120, the housing 620 can include a substantially hollow cylindrical body. The shape of the housing 620 can be optimized to reduce resistance to flow within the housing 620. In some examples, the housing 620 can comprise different shapes, for example, rectangular, square, hexagonal, or semi-circular. In some embodiments the shape of the housing 620 can minimize volume within the housing 620. This can reduce dead space—therefore reducing the build-up of carbon dioxide within the housing 620. The housing 620 can be compact so as to reduce the weight and bulk of the housing 620 and improve patient comfort. As discussed with regard to the adaptor 100, the housing 620 can be configured to both receive gases through an inspiratory tube and aid the exit of gases through an expiratory tube.

The housing 620 can include a coupling surface 640 at an end of the housing 620 that is proximate to the patient. As illustrated in FIGS. 7A-7B, the coupling surface 640 can be rectangular in cross-section. The coupling surface 640 can include a first end that is fluidly connected with the housing 620 and a second end that is configured to couple with the patient interface 650. The second end of the coupling surface 640 can allow fluid communication between the housing 620 and the patient interface 650. In some embodiments, a partial barrier can exist between the housing 620 and the first end of the coupling surface 640. An orifice can thus maintain fluid communication between the housing 620 and the patient interface 650. The orifice can direct the flow of gases toward the patient interface 650. In some examples, the orifice can control the pressure of the gas flow as it enters the patient interface 650.

In some embodiments, the patient interface 650 is similar if not identical to the patient interface 150 of adaptor 100. As discussed, the patient interface 650 can be configured to be removably coupled with the coupling surface 640. In some examples the patient interface 650 can be coupled with the coupling surface 640 using adhesives or mechanical mechanisms such as snap-fit mechanisms. In some embodiments, the patient interface 650 can be permanently attached to the coupling surface 640 using adhesives, snap-fit mechanisms, or welding techniques. FIGS. 7A-7G illustrate a patient interface 650 that is transparent so as to allow the engagement between the coupling surface 640 and the patient interface 650 to be visualized. The patient interface 650 can include a substantially hollow complementary region 655 that is configured to receive the coupling surface 640. In some embodiments, the coupling surface 640 can be configured to receive the complementary region 655 of the patient interface 650. In some embodiments, the patient interface 650 can be permanently coupled with the adaptor 600. This can provide a fully integrated adaptor which may improve the usability of the adaptor 600.

As illustrated in FIGS. 7A-7B, in some examples, the patient interface 650 can include nasal prongs 652. In some embodiments, the patient interface 650 can include respiratory interfaces such as, but not limited to, a nasal mask, oral mask, combined nasal and oral mask, tracheal mask, or nasal pillows. In some embodiments, the adaptor 600 can be adapted for use in a surgical application. The patient interface 650 can include a diffuser, trocar, or catheter.

In some embodiments, the adaptor 600 can include clips 630 that are positioned on first and second sides of the housing 620. As illustrated in FIGS. 7A-7B, the first and second sides of the coupling surface 640 can be substantially perpendicular to the first and second ends of the coupling surface 640. In some embodiments, the clips 630 can be configured to be mobile clips. For example, the clip 630 can be positioned on a slidable and/or rotatable bar or cord. In this way, the position of the clips 630 can be rotated or altered to simplify the attachment of the patient stabilising mechanism to the adaptor 600. In some embodiments, the clips 630 can be configured to permanently attach to an interface stabilising mechanism.

As discussed above, in some examples, the clips 630 can engage a removable attachment that is attached to an interface stabilising mechanism, such as headgear or a hat or bonnet. As described above, an example of the removable attachment is illustrated in FIGS. 13A and 13B.

In some embodiments, the adaptor 600 can include a plurality of conduits that act as the inlet and outlet of air flow that are located adjacent to each. In some embodiments, the plurality of conduits runs parallel to each other. As illustrated in FIGS. 7A and 7B, as the plurality of conduits are located adjacent to each other, the inlet port 660 and the outlet port 680 are interchangeable and can be located on either side of the housing 620.

In some examples, the adaptor 600 can include an inlet port 660 that can be fluidly connected to an inspiratory tube 6 from a humidification apparatus and allow fluid flow through the inlet tube 664 in a first direction. In some embodiments, the inlet tube 664 can include an engagement portion 665 at a first end that engages with the inspiratory tube 6. In some embodiments, the inlet tube 664 is secured to the inspiratory tube 6 using a securing portion 668. The securing portion 668 can allow the inlet tube 664 to be removably attached to the inspiratory tube 6. For example, as illustrated in FIGS. 7A and 7B, the securing portion 668 can be threaded and configured to engage internal threading located on a portion of the inspiratory tube 6. However, the securing portion 668 can come in any shape and size, such as a tab, latch, or any locking feature that has a complementary securing portion on the inspiratory tube 6. In some embodiments, the securing portion 668 can allow the adaptor 600 to be directly attached to the respiratory assistance system 1. This can help, for example, to reduce the number of parts in the respiratory assistance system 1 as well as reduce the manufacturing costs.

In some embodiments, the outlet port 680 can be configured to receive an expiratory tube 4. In some examples, the outlet port 680 can be fluidly connected to the respiratory assistance system 1 to allow fluid flow through the outlet tube 684 in a second direction. The outlet tube 684 can include an engagement portion 665 at a first end that engages with the expiratory tube 4. In some embodiments, the outlet tube 684 can be secured to the expiratory tube 4 using a securing portion 688. The securing portion 688 can allow the outlet tube 684 to be removably attached to the expiratory tube 4. For example, as illustrated in FIGS. 7A and 7B, the securing portion 688 can be threaded and configured to engage internal threading located on a portion of the expiratory tube 4. However, the securing portion 688 can come in any shape and size, such as a latch, threaded portion, or any locking feature that has a complementary securing portion on the expiratory tube 4. As was discussed with regard to the securing portion 668, in some embodiments, the securing portion 688 can allow the adaptor 600 to be directly attached to the respiratory assistance system 1. This can help, for example, to reduce the number of parts in the respiratory assistance system 1 as well as reduce the manufacturing costs.

In some examples, the inlet tube 664 and the outlet tube 684 are configured to extend above and away from the patient. As with the adaptor 300 and adaptor 400, the adaptor 600 retains the narrow body of the "over" and "under" design, but, as mentioned above, the connectors are now side-by-side so connections are interchangeable. As discussed, with regard to the adaptor 600, this design of the inlet tube 664 and the outlet tube 684 can help to reduce the mass across the patient's face. In some examples, the inlet tube 664 and the outlet tube 684 can be more rigid so as to be able to hold onto its shape without contacting the patient. The inlet tube 664 and the outlet tube 684 can help to reduce the weight perceived by the patient by spreading out or increasing the distribution of forces from the interface and tubing, reducing patient discomfort. In some embodiments, the location of the inlet port 660 and the outlet port 680 can be alternated.

In some examples, the adaptor 600 can include a pressure tube 674 with a pressure port 670 and a pressure lumen 672 that is fluidly connected to the housing 620. As illustrated in FIG. 6C, the pressure tube 674 extends below the pair of conduits (the inlet port 660 and the outlet port 680) such that the pressure port 670 is directed towards the face of the patient. In some embodiments, the pressure port 670 is located further away from the nose of the patient such that it does not interact with the patient's face. As the pressure port 670 does not interfere with the patient's face, the pressure port 670 does not need to extend into a foam block. In some embodiments, the location of the surfactant port 610 and the pressure port 670 can be reversed.

The pressure tube 674 can generally extend vertically between the inlet port 660 and outlet port 680 before making an approximately right angle turn towards the housing 620 such that the pressure lumen 672 extends between the inlet port 660 and outlet port 680 through the center of the adaptor 600. In some embodiments, the pressure lumen 672 extends towards the housing 620 such that the pressure port 670 and pressure lumen 672 are fluidly connected to the housing 620. In some embodiments, the pressure tube 674 is fluidly connected to a pressure line which is fluidly connected to the pressure regulating device 7.

As with the adaptor 100, in some embodiments, the adaptor 600 can include nozzle 622 that is configured to connect with an external device to provide a fluid connection with the inside of the housing 620. In some examples, the nozzle 622 can be fluidly connected to another conduit to isolate and restrict the mixing of the aerosolized material (for example, a drug) with the air flow coming through the inlet tube 664.

As illustrated in FIGS. 7C-7G, in some embodiments, the nozzle 622 can be fluidly connected to a surfactant tube 614. The surfactant tube 614 can have a surfactant port 610 and a surfactant lumen 612. As shown in FIG. 6C, the surfactant port 610 is located closer to the patient's forehead and is closer to the housing 620 than the pressure port 670. In some embodiments, the surfactant tube 614 extends above the pair of conduits (the inlet port 660 and the outlet port 680) such that the surfactant port 610 is directed away from the face of the patient. The surfactant tube 614 can make an approximately right turn towards the housing 620. In some examples, the surfactant lumen 612 can extend towards the housing 620 between the inlet port 660 and pressure port 670 such that the surfactant tube 614 is on the side of the adaptor 600 furthest away from the patient. In some embodiments, the surfactant lumen 612 extends towards the housing 620 such that the surfactant port 610 and the surfactant lumen 612 are fluidly connected to the housing 620.

In some examples, the surfactant tube 614 can have a surfactant port 610 at a first end of the surfactant tube 614 that is configured to be fluidly connected to the respiratory assistance system 1 to allow the delivery of a substance, such as an aerosolized surfactant, through the housing 620 and to the patient through the patient interface 650.

In some embodiments, the surfactant tube 614 can be fluidly connected with an external device such as a medicament delivery device. In some embodiments, the medicament delivery device can be a nebulizer, a capillary aerosol generator, or a metered dose inhaler (MDI). A nebuliser such as a flow based nebuliser, for example, can deliver aerosolised surfactant to the patient. In some embodiments, a nebuliser can be configured to deliver a medicament or anaesthetic substance to the patient.

In some embodiments, the surfactant tube 614 can have a circular cross-section which ensures that the surfactant lumen 612 does not have any sharp edges so as to reduce deposition within the surfactant lumen 612. The surfactant tube 614 is not limited to a tubular shape, and can comprise any number of shapes. The surfactant port 610 of the surfactant tube 614 is located directly over the nose so as to reduce the deposition of medicament within the surfactant lumen 612 and ensure sufficient delivery of medicament to the patient.

In contrast to the adaptor 400, the surfactant port 610 and the pressure port 670 extend from opposing sides of the adaptor 600. The surfactant port 610 and the pressure port 670 directing from opposing side of the adaptor 600 helps to avoid confusion and entanglement of the surfactant port 610 and the pressure port 670.

The body of the adaptor 600 can be divided into a plurality of compartments. FIGS. 7C-7G illustrate the configuration of the adaptor 600 and the airflow through the tubular body 690, surfactant lumen 612, pressure lumen 672, and the housing 620. As illustrated in FIGS. 7C-7G, the tubular body 690 can be divided into an inlet lumen 662 and an outlet lumen 682. The plurality of compartments within the adaptor 600 can reduce premixing of the medicament received through the surfactant port 610 and the inspiratory gases through the inlet lumen 662 and reduce dilution of the drug by the outgoing gases through the outlet port 680. In some examples, the arrangement of the conduits within the adaptor 600 can help to maximize gas flow to the patient. For example, inspiratory gases can enter the adaptor 600 through the inlet port 660 and flow through the inlet lumen 662 and into the housing 620. There, the gases can mix with the medicament delivered from the surfactant tube 614 near the opening of the nostril lumens (not pictured). As illustrated in FIG. 6C, there is a gap between the end of the surfactant tube 614 and the nostril lumens (not illustrated) of the patient interface 650 that allow inspiratory gases to flow in. In some embodiments, the expiratory gases can then exit the patient interface 650 and move around the surfactant tube 614, flow through the outlet lumen 682, and exit the adaptor 600 from the outlet port 680.

Figure 8A:
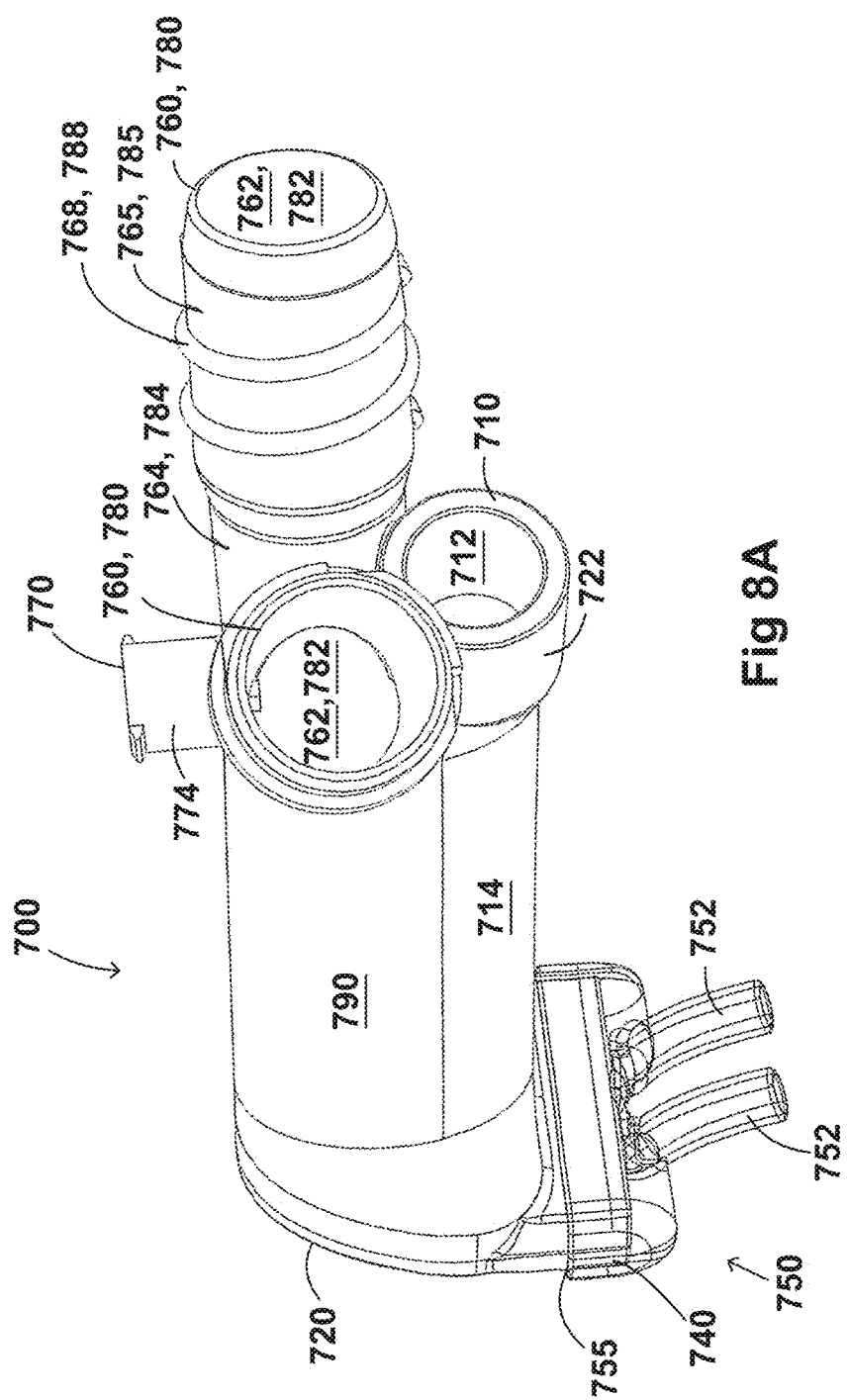
Figure 8B:
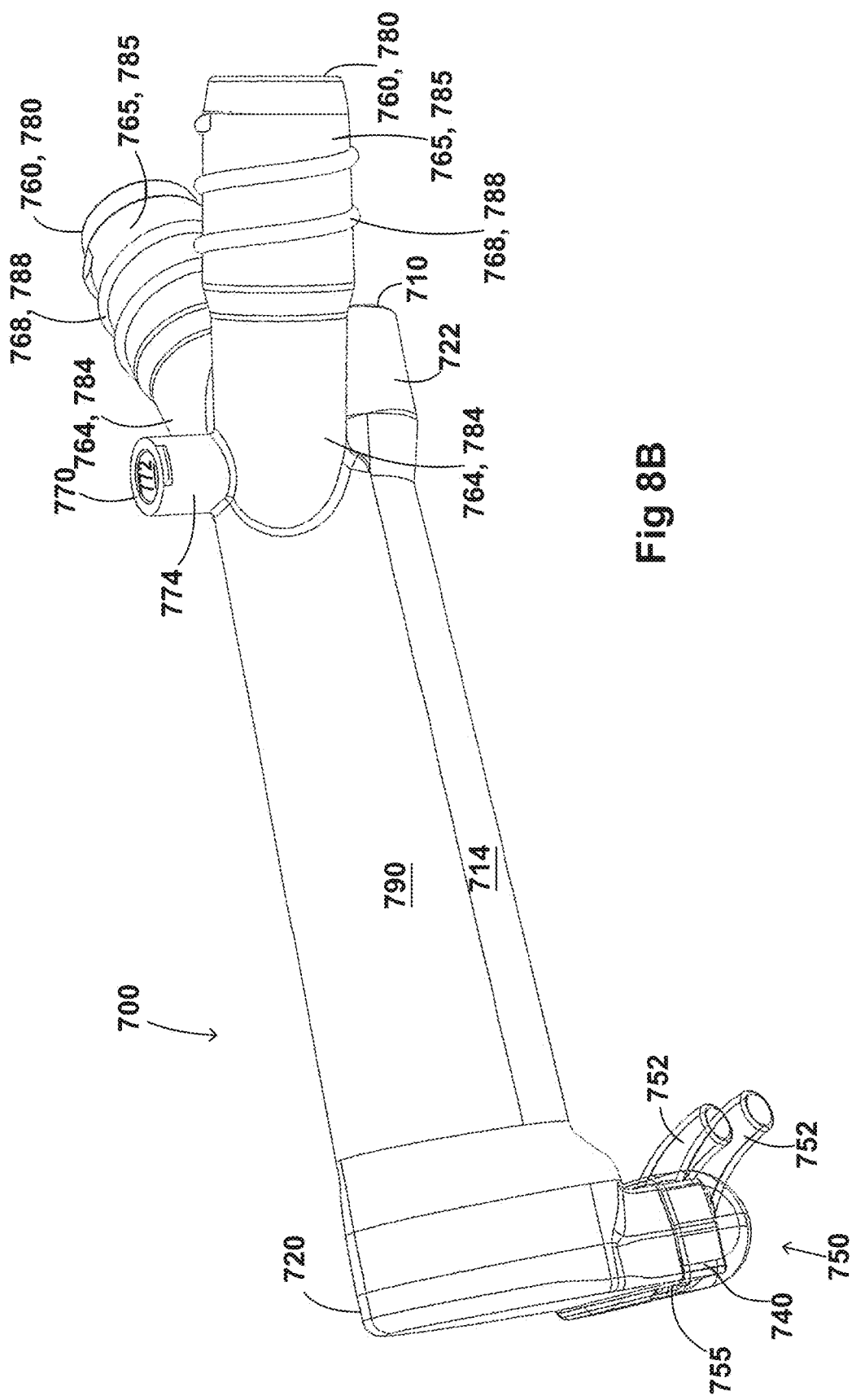
Figure 8C:
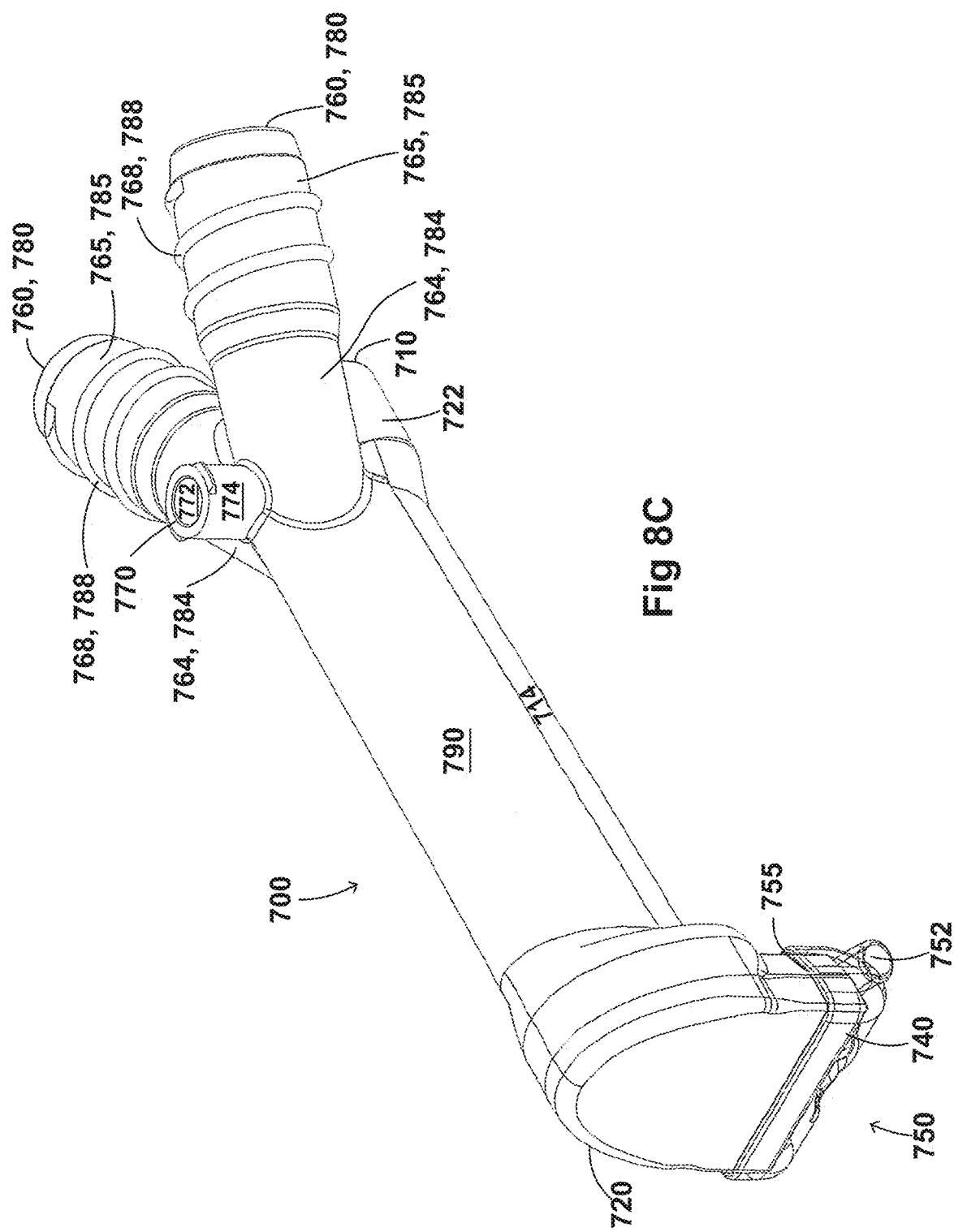

FIGS. 8A-8F illustrate another embodiment of an adaptor 700. The adaptor 700 resembles or is identical to the adaptor 100 in many respects. Accordingly, the numerals used to identify components of the system for adaptor 700 are incremented by one hundred to identify like features of the adaptor 700. This number convention generally applies to the remainder of the Figures. Any component disclosed in any embodiment in this specification can be used in other embodiments. In some embodiments, the adaptor 700 is configured to have an oval tube oriented to present the smallest possible trunk width between the patient's (for example, the infant's) eyes while maintaining a sufficient cross-section to provide sufficient air flow. The generally oval shaped inlet tube or tube also helps to provide a substantially lower profile adaptor or patient interface. The oval inlet tube reduces the distance the adaptor or patient interface 700 extends outwardly from a patient's face when in an operational or in use position. The adaptor 700 may be known as a patient interface since it engages a patient's face with prongs. Turning first to FIGS. 8A-8C, illustrated is an embodiment of the adaptor 700. Like the adaptor 100, the adaptor 700 can include a housing 720 that is fluidly connected to a plurality of conduits to provide fluid flow, such as air, and the delivery of aerosolized surfactants to the patient through the patient interface 750.

The adaptor 700 can include a housing 720, a plurality of clips (not shown), an inlet port 760, and outlet port 780, a pressure port 770, a surfactant port 710, and a coupling surface 740 for engaging a patient interface 750. The pressure port 770 includes an opening and can include a pressure lumen that is inserted through the pressure port or alternatively can include a pressure sensor arrangement mounted on or connected to the pressure port 770. The pressure port 770 is optional and the adaptor 700 may not include a pressure port within it.

In some examples, as with the housing 120, the housing 720 can include a substantially hollow cylindrical body. The shape of the housing 720 can be optimized to reduce resistance to flow within the housing 720. In some examples, the housing 720 can comprise different shapes, for example, rectangular, square, hexagonal, or semi-circular. The housing 720 includes smooth curves and radiused corners to improve fluid flow around corners. In some embodiments the shape of the housing 720 can minimize volume within the housing 720. This can reduce dead space—therefore reducing the build-up of carbon dioxide within the housing 720. The housing 720 can be compact so as to reduce the weight and bulk of the housing 720 and improve patient comfort. As discussed with regard to the adaptor 100, the housing 720 can be configured to both receive gases through an inspiratory tube and aid the exit of gases through an expiratory tube.

The housing 720 can include a coupling surface 740 at an end of the housing 720 that is proximate to the patient. As illustrated in FIGS. 8A-8D, the coupling surface 740 can have a rectangular cross-section. The coupling surface 740 can include a first end that is fluidly connected with the housing 720 and a second end that is configured to couple with the patient interface 750. The second end of the coupling surface 740 can allow fluid communication between the housing 720 and the patient interface 750. In some embodiments, a partial barrier can exist between the housing 720 and the first end of the coupling surface 740. An orifice can therefore maintain fluid communication between the housing 720 and the patient interface 750. The orifice can direct the flow of gases toward the patient interface 750. In some examples, the orifice can control the pressure of the gas flow as it enters the patient interface 750.

In some embodiments, the patient interface 750 is similar if not identical to the patient interface 150 of the adaptor 100. In the illustrated embodiments the patient interface 750 comprises sealing nasal prongs that can substantially seal with the nasal openings of a patient. As discussed, the patient interface 750 can be configured to be removably coupled with the coupling surface 740. In some examples the patient interface 750 can be coupled with the coupling surface 740 using adhesives or mechanical mechanisms such as snap-fit mechanisms. In some embodiments, the patient interface 750 can be permanently attached to the coupling surface 740 using adhesives, snap-fit mechanisms, or welding techniques. FIGS. 8A-8D illustrate a patient interface 750 that is transparent so as to allow the engagement between the coupling surface 740 and the patient interface 750 to be visualized. The patient interface 750 can include a substantially hollow complementary region 755 that is configured to receive the coupling surface 740. In some embodiments, the coupling surface 740 can be configured to receive the complementary region 755 of the patient interface 750. In some embodiments, the patient interface 750 can be permanently coupled with the adaptor 700. This can provide a fully integrated adaptor which may improve the usability of the adaptor 700.

As illustrated in FIGS. 8A-8D, in some examples, the patient interface 750 can include nostril ports 752. In some embodiments, the patient interface 750 can include respiratory interfaces such as, but not limited to, a nasal mask, oral mask, combined nasal and oral mask, tracheal mask, or nasal pillows. In some embodiments, the adaptor 700 can be adapted for use in a surgical application. The patient interface 750 or 550 can include a diffuser, trocar, or catheter. The patient interface may also be an invasive interface such as an endotracheal tube that can be inserted into an airway of a patient. The illustrated interface 750 is a non-invasive interface and is easier to use since a patient does not need to be intubated or potentially sedated either. This can be particularly useful for neonatal patients or infant patients.

In some embodiments, the adaptor 700 can include clips (not shown) that are positioned on first and second sides of the housing 720. As illustrated in FIGS. 8A-8C, the first and second sides of the coupling surface 740 can be substantially perpendicular to the first and second ends of the coupling surface 740. In some embodiments, the clips (not shown) can be configured to be mobile clips. For example, the clips (not shown) can be positioned on a slidable and/or rotatable bar or cord. In this way, the position of the clips (not shown) can be rotated or altered to simplify the attachment of the patient stabilising mechanism to the adaptor 700. In some embodiments, the clips (not shown) can be configured to permanently attach to an interface stabilising mechanism.

As discussed above, in some examples, the clips (not shown) can engage a removable attachment that is attached to an interface stabilising mechanism, such as headgear or a hat or bonnet. As described above, an example of the removable attachment is illustrated in FIGS. 13A and 13B. Alternatively a headgear may comprise a plurality of straps with removable couplers at the ends such as hook and loop couplers.

Figure 8D:
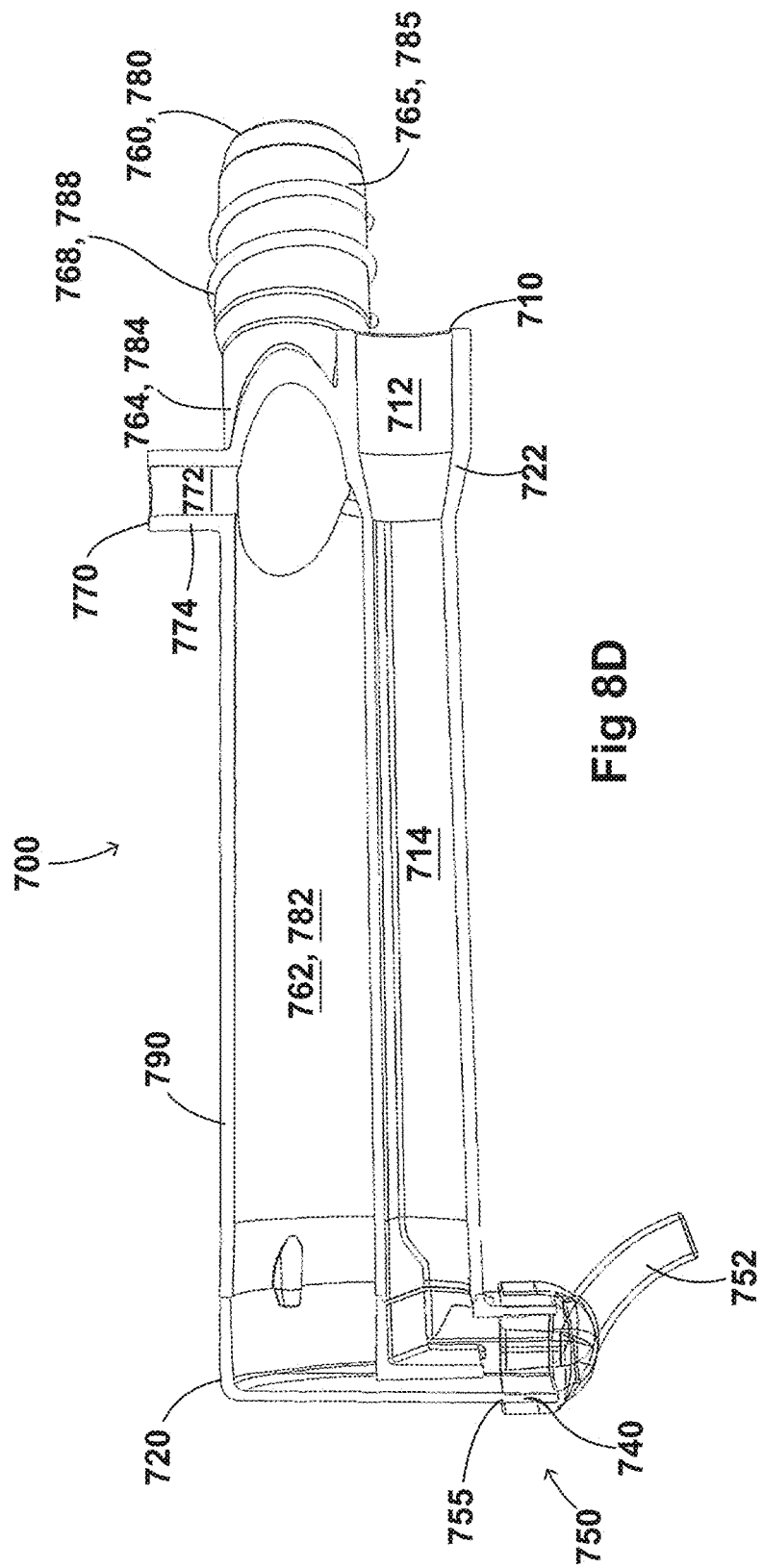
Figure 8E:
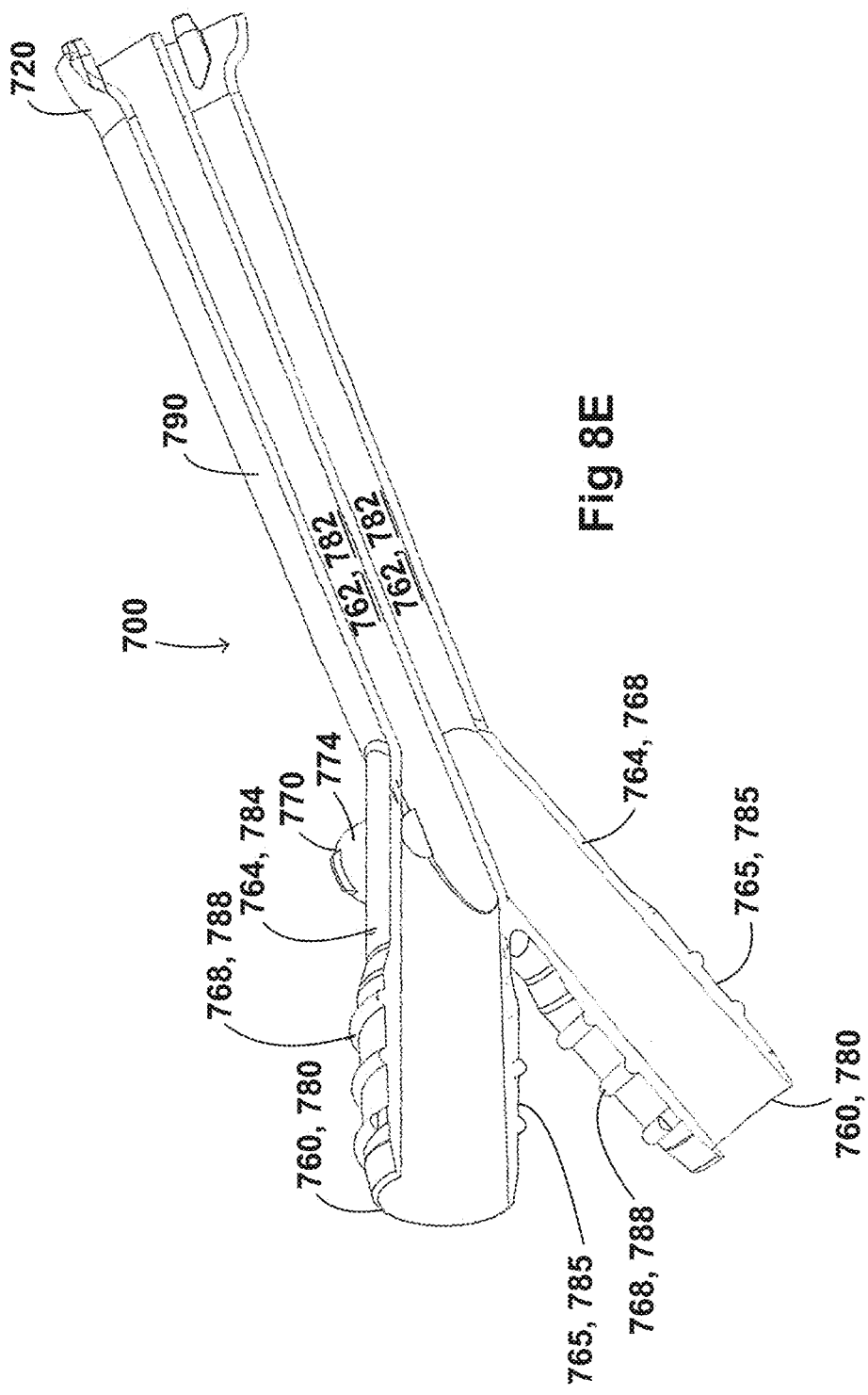
Figure 8F:
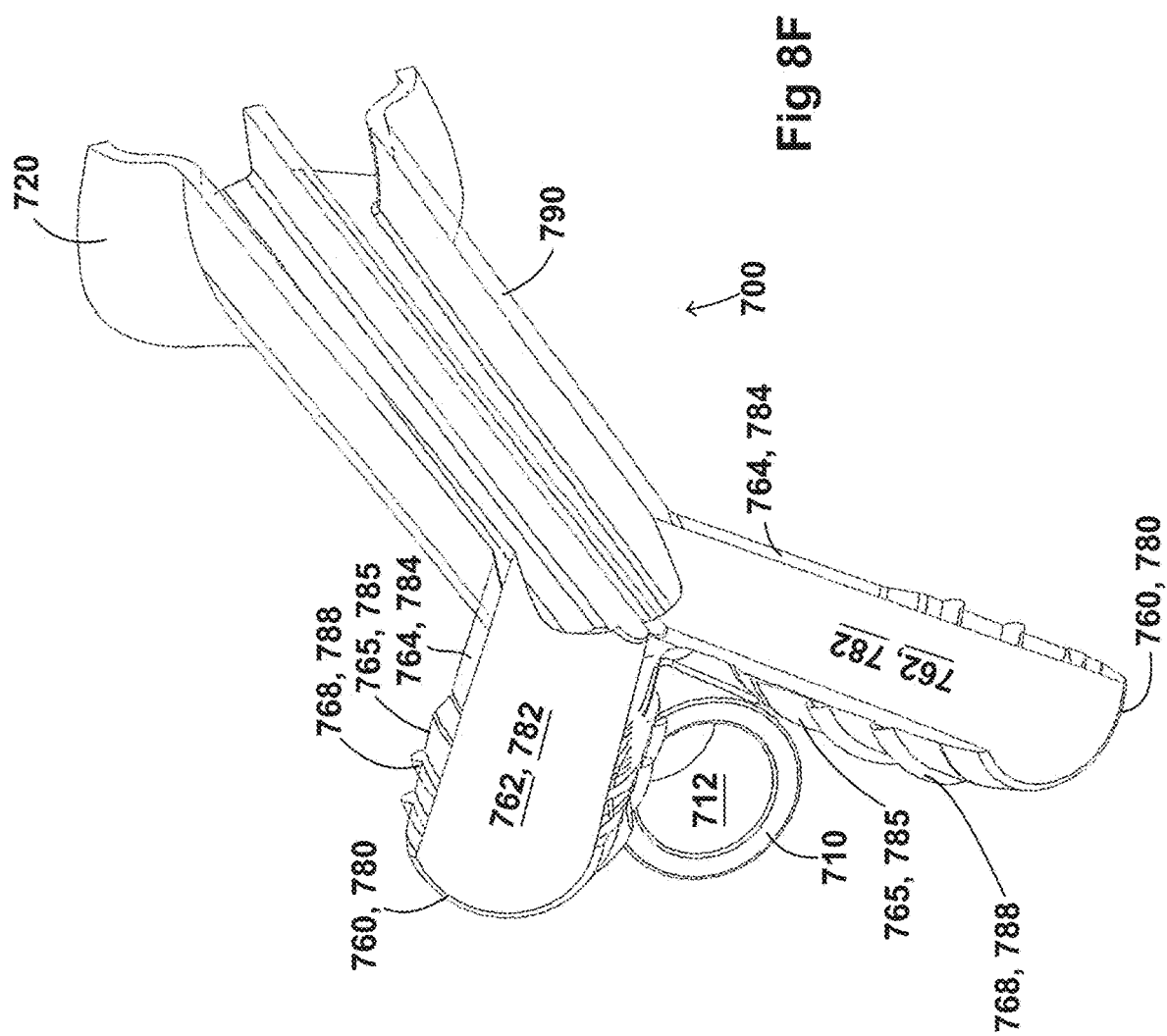

In some embodiments, the adaptor 700 can include a plurality of conduits that act as the inlet and outlet of air flow that are located adjacent to each other. In some embodiments, the plurality of conduits runs parallel to each other. FIG. 8D illustrates a vertical cross-section along the length of the adaptor 700. FIG. 8E illustrates a top-half of a horizontal cross-section along the length of the adaptor 700. FIG. 8F illustrates a bottom-half of a horizontal cross-section along the length of the adaptor 700.

As illustrated in FIGS. 8A-8C and 8E-8F, as the plurality of conduits are located adjacent to each other, the inlet port 760 and the outlet port 780 are interchangeable and can be located on either side of the housing 720.

In some examples, the adaptor 700 can include an inlet port 760 that can be fluidly connected to an inspiratory tube 6 from a humidification apparatus and allow fluid flow from the inlet tube 764 in a first direction. In some embodiments, the inlet tube 764 can include an engagement portion 765 at a first end that engages with the inspiratory tube 6. In some embodiments, the inlet tube 764 is secured to the inspiratory tube 6 using a securing portion 768. The securing portion 768 can allow the inlet tube 764 to be removably attached to the inspiratory tube 6. For example, as illustrated in FIGS. 8A-8C and 8E-8F, the securing portion 768 can be threaded and configured to engage internal threading located on a portion of the inspiratory tube 6. However, the securing portion 768 can come in any shape and size, such as a tab, latch, or any locking feature that has a complementary securing portion on the inspiratory tube 6. In some embodiments, the securing portion 768 can allow the adaptor 700 to be directly attached to the respiratory assistance system 1. This can help, for example, to reduce the number of parts in the respiratory assistance system 1 as well as reduce the manufacturing costs. In alternative embodiments the securing portion 768 may be a medical taper such as a 22 mm or 15 mm taper. The inspiratory tube 6 can be push fitted onto the securing portion 768 by urging a portion of the inspiratory tube 6 onto the securing portion. The inspiratory tube 6 is held on the medical taper by friction.

In some embodiments, the outlet port 780 can be configured to receive an expiratory tube 4. In some examples, the outlet port 780 can be fluidly connected to the respiratory assistance system 1 to allow fluid flow in a second direction. The outlet tube 784 can include an engagement portion 765 at a first end that engages with the expiratory tube 4. In some embodiments, the outlet tube 784 can be secured to the expiratory tube 4 using a securing portion 788. The securing portion 788 can allow the outlet tube 784 to be removably attached to the expiratory tube 4. For example, as illustrated in FIGS. 8A-8C, the securing portion 788 can be threaded and configured to engage internal threading located on a portion of the expiratory tube 4. However, the securing portion 788 can come in any shape and size, such as a latch, threaded portion, or any locking feature that has a complementary securing portion on the expiratory tube 4. As was discussed with regard to the securing portion securing portion 768, in some embodiments, the securing portion 788 can allow the adaptor 700 to be directly attached to the respiratory assistance system 1. This can help, for example, to reduce the number of parts in the respiratory assistance system 1 as well as reduce the manufacturing costs. In alternative embodiments the securing portion 788 may be a medical taper such as a 22 mm or 15 mm taper. The expiratory tube 4 can be push fitted onto the securing portion 788 by urging a portion of the expiratory tube 4 onto the securing portion. The expiratory tube 4 is held on the medical taper by friction.

In some examples, the inlet tube 764 and the outlet tube 784 are configured to extend above and away from the patient. As with the adaptor 300, adaptor 400, adaptor 500, and adaptor 600, the adaptor 700 retains the narrow body of the "over" and "under" design, but, as mentioned above, the connectors are now side-by-side so connections are interchangeable. As discussed, with regard to the adaptor 700, this design of the inlet tube 764 and the outlet tube 784 can help to reduce the mass across the patient's face. In some examples, the inlet tube 764 and the outlet tube 784 can be more rigid so as to be able to hold onto its shape without contacting the patient. The inlet tube 764 and the outlet tube 784 can help to reduce the weight perceived by the patient by spreading out or increasing the distribution of forces from the interface and tubing, reducing patient discomfort. In some embodiments, the location of the inlet port 760 and the outlet port 780 can be alternated.

In some examples, the adaptor 700 can include a pressure tube 774 with a pressure port 770 and a pressure lumen 772 that is fluidly connected to the housing 720. In comparison to the adaptor 400, adaptor 500, or the adaptor 600, the pressure tube 774 of the adaptor 700 extends approximately perpendicularly from the body of the adaptor 700 such that the pressure port 770 is fluidly connected to both the inlet lumen 762 and the outlet lumen 782. In some embodiments, the pressure tube 774 is fluidly connected to a pressure line which is fluidly connected to the pressure regulating device 7.

As with the adaptor 100, in some embodiments, the adaptor 700 can include a nozzle 722 that is configured to connect with an external device to provide a fluid connection with the inside of the housing 720. In some examples, the nozzle 722 can be fluidly connected to another conduit to isolate and restrict the mixing of the aerosolized material (for example, a drug) with the air flow coming through the inlet tube 764.

As illustrated in FIG. 8D, in some embodiments, the nozzle 722 can be fluidly connected to a surfactant tube 714. The surfactant tube 714 can have a surfactant port 710 and a surfactant lumen 712. As shown in FIG. 8C, in some embodiments, the surfactant tube 714 is approximately parallel with the pair of conduits (the inlet port 760 and the outlet port 780). Unlike the surfactant tubes (414, 514, 614) of the previously disclosed adaptors (400, 500, 600), the surfactant tube 714 does not make an approximate turn towards the housing 720. The surfactant tube 714 opens into a portion of the housing 720 and mixes with the ventilation airflow (for example, airflow from a ventilator). The ventilation airflow and surfactant flow are parallel to each other until they mix within the housing 720. In some embodiments, this can reduce the likelihood of surfactant deposit within the surfactant lumen 712. In an alternative embodiment the surfactant tube may open into the housing after a turn within the surfactant tube, however the turn in the surfactant tube is a shallow turn of an obtuse angle, i.e. greater than 90 degrees. The obtuse angle turn also includes smooth edges and rounded edges to reduce collection or deposition of the surfactant.

In some examples, the surfactant tube 714 can have a surfactant port 710 at a first end of the surfactant port 710 that is configured to be fluidly connected to the respiratory assistance system 1 to allow the delivery of a substance, such as an aerosolized surfactant, through the housing 720 and to the patient through the patient interface 750. Alternatively the surfactant port 710 or surfactant nozzle 722 may be connected to an aerosol generator either directly or through a tube or pipe.

In some embodiments, the surfactant tube 714 can be fluidly connected with an external device such as a medicament delivery device. In some embodiments, the medicament delivery device can be a nebulizer, a capillary aerosol generator, or a metered dose inhaler (MDI). A nebuliser such as a flow based nebuliser, for example, can deliver aerosolised surfactant to the patient. In some embodiments, a nebuliser can be configured to deliver a medicament or anaesthetic substance to the patient.

In some embodiments, the surfactant tube 714 can have a circular cross-section that ensures that the surfactant lumen 712 does not have any sharp edges so as to reduce deposition within the surfactant lumen 712. The surfactant tube 714 is not limited to a tubular shape, and can comprise any number of shapes. The surfactant port 710 of the surfactant tube 714 is configured so as to reduce the deposition of medicament within the surfactant lumen 712 and ensure sufficient delivery of medicament to the patient. Alternatively the surfactant tube 714 may have an elliptical or oval cross section. In a further alternative the surfactant tube 714 may have a polygon cross section such as for example triangular, square, rectangular, pentagonal etc. If a polygon cross section is utilized the polygon shape will have rounded corners and edges to reduce any sharp edges to reduce surfactant deposition.

Similar to the adaptor 600, the surfactant port 710 and the pressure port 770 are located on opposite sides of the adaptor 700. The surfactant port 710 and the pressure port 770 located and directed in different sides of the adaptor 700 helps to avoid confusion and entanglements of the surfactant port 710 and the pressure port 770.

Figure 9C:
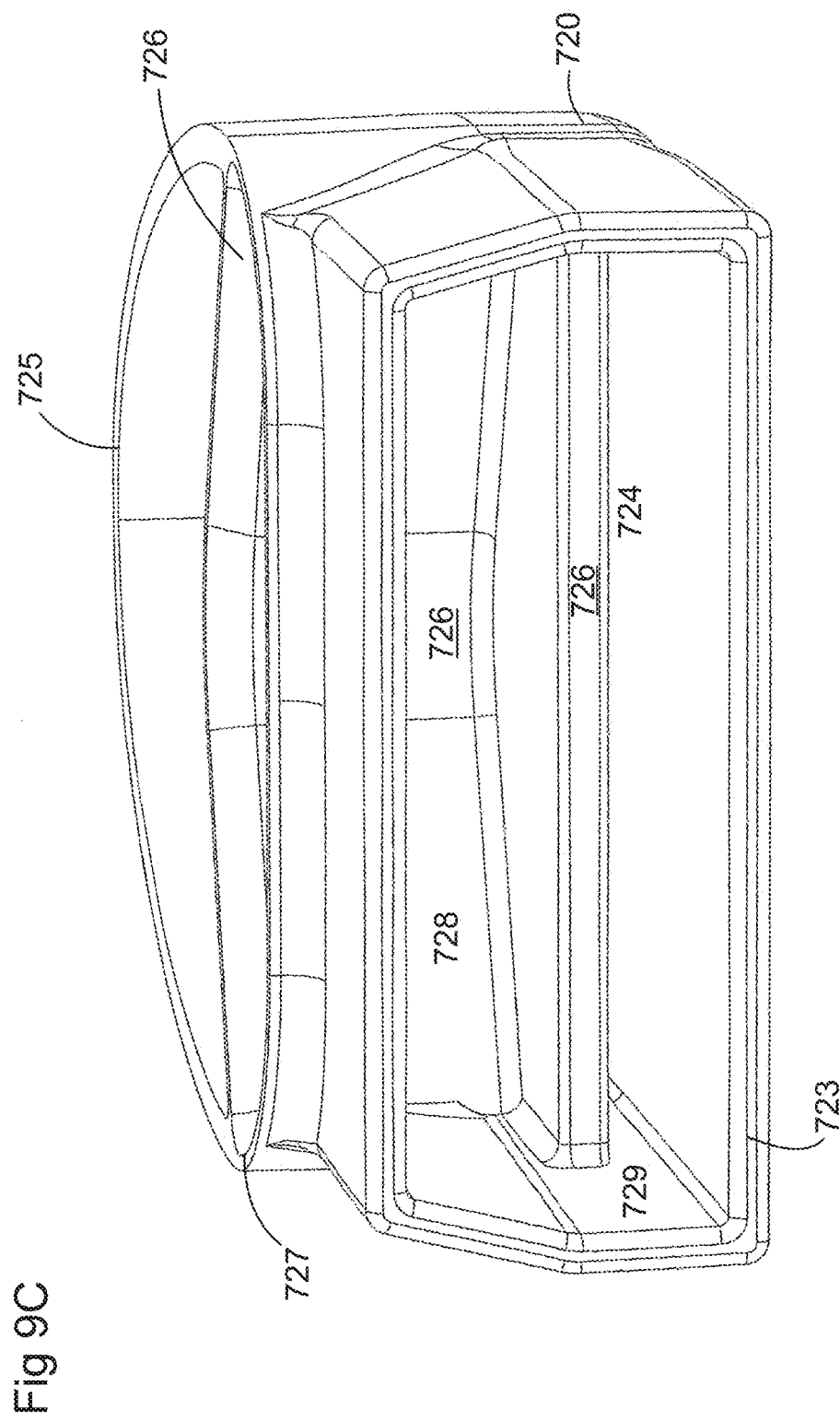

The body of the adaptor 700 can be divided into a plurality of compartments. FIGS. 8C-8F illustrate the configuration of the adaptor 700 and the airflow through tubular body 790, surfactant lumen 712, pressure lumen 772, and the housing 720. As illustrated in FIGS. 8C-8F, the tubular body 790 can be divided into the inlet lumen 762 and the outlet lumen 782. As will be discussed in more detail below, the housing 720 can have a number of different configurations to provide for different amounts of airflow from the inlet lumen 762/pressure lumen 772 and the surfactant lumen 712.

In some examples, the arrangement of the conduits within the adaptor 700 can help to maximize gas flow to the patient. For example, inspiratory gases can enter the adaptor 700 through the inlet port 760 and flow through the inlet lumen 762 and into the housing 720. There, the gases can mix with the medicament delivered from the surfactant tube 714 near the opening of the nostril lumens 754. As illustrated in FIG. 8C or 8D (and described in more detail with regard to the housing 720), there is a gap or hollow space between the end of the surfactant tube 714 and the nostril lumens 754 of the patient interface patient interface 750 that allow inspiratory gases to mix with. In some embodiments, the expiratory gases can then exit the patient interface 750 and through the housing 720, flow through the outlet lumen 782, and exit the adaptor 700 from the outlet port 780. In some instances within use inlet gases enters the housing 720 from the inlet lumen and can turn and exit out of the outlet lumen 782 without going to the patient.

In some embodiments, the embodiment of the adaptor 700 illustrated in FIGS. 8A-8F are configured to provide an air flow path such that the air flowing past the infant (i.e. in a bias flow path) goes from the inlet lumen 762 to the outlet lumen 782 around a bend. Bias flow occurs because the gas flow rate may be higher than the patient's inspiratory demand, or the patient may be exhaling. Accordingly, rather than entering the patient, the excess or bias gas flow will continue into the expiratory limb. Many medicament delivery adaptors suffer from an issue with medicament being washed out through the bias flow, and never entering the patient. This occurs because the medicament delivery point is either upstream of or within the bias flow path. As will be illustrated in FIGS. 9A-9D, the housing 720, 820, 920, 1020 can be configured to keep the surfactant flow path or delivery point out of the bias flow path such that the inlet lumen 762 and outlet lumen 782 are fluidly connected upstream of the point where surfactant is delivered to the air flow path. Delivering surfactant to the air flow path after or downstream of the exchange of air from the inlet lumen 762 and the outlet lumen 782 ensures less dilution of the surfactant to the infant as well as reducing the deposition of the surfactant on the interior of the adaptor 700.

In some examples, the above disclosed adaptors are configured to provide greater stability over the infant's face. For example, the above disclosed adaptors are retained fairly close to the face of the infant such that it does not extend high off the infant's face. In this way, the disclosed adaptor is firmly secured to the face of the infant. An adaptor that extends high off the infant's face increases the risk that movement of the adaptor will cause bending and/or twisting of the adaptor about the infant's nose. Movement (e.g. bending, twisting) of the adaptor about the infant's nose can cause nasal trauma to the infant. This is particularly of great concern where the patient is a premature baby as premature babies are particularly fragile.

In some examples, the size of the above disclosed adaptors allows for longer use on an infant (e.g. 7 days). By providing for an adaptor that can be used for an extended period of time without adjustment, the disclosed adaptor can reduce irritation and trauma to the nose of the infant.

FIGS. 9A-9D illustrates an embodiment of the housing 720. In some embodiments, the housing 720 is configured to provide a mixture of airflow from the CPAP and aerosolized surfactant or aerosolized medicaments or aerosolized drugs from the nozzle, to the patient. As shown in FIGS. 9A-9B, in some examples, the housing 720 can be divided into a plurality of compartments. As discussed above and in more detail below, the configuration of the housing 720 can provide for improved drug delivery to the patient.

In some examples, the inside of the housing 720 can include a divider 726 that divides the housing 720 to provide a housing airflow entrance 725 with a housing airflow pathway 724 and a housing surfactant entrance 727 with a housing surfactant lumen 728. In some embodiments, the housing airflow entrance 725 is configured to fluidly connect with the both the inlet lumen 762 and the outlet lumen 782. This can allow inspiratory air from the inlet lumen 762 and expiratory air from the outlet lumen 782 to flow through the housing airflow pathway 724.

Similarly, in some embodiments, the housing surfactant lumen 728 is configured to fluidly connect with the surfactant lumen 712. As discussed above, this can allow surfactant to flow from the surfactant lumen 712 into the housing surfactant lumen 728 without mixing with the inspiratory air from the inlet lumen 762.

FIGS. 9C-9D provides a view of the housing 720 from the housing exit 723, wherein the entrance to the housing 720 (the housing airflow entrance 725 and the housing surfactant entrance 727) is oriented upwards. As shown, the divider 726 provides two separate compartments for the inspiratory/expiratory airflow and the surfactant flow. As discussed above, the housing 720 near the housing exit 723 includes an undivided portion 729 that allows the inspiratory air from the inlet lumen 762 to mix with the surfactant from the surfactant lumen 712 before being delivered to the patient. As seen in FIG. 9C the divider goes through a turn section but the turn portion includes rounded edges to reduce aerosolized surfactant deposition at the turn. The housing airflow pathway 724 provides inspiratory airflow into the undivided portion to allow mixing of inspiratory airflow and aerosolized surfactant.

Figure 9D:
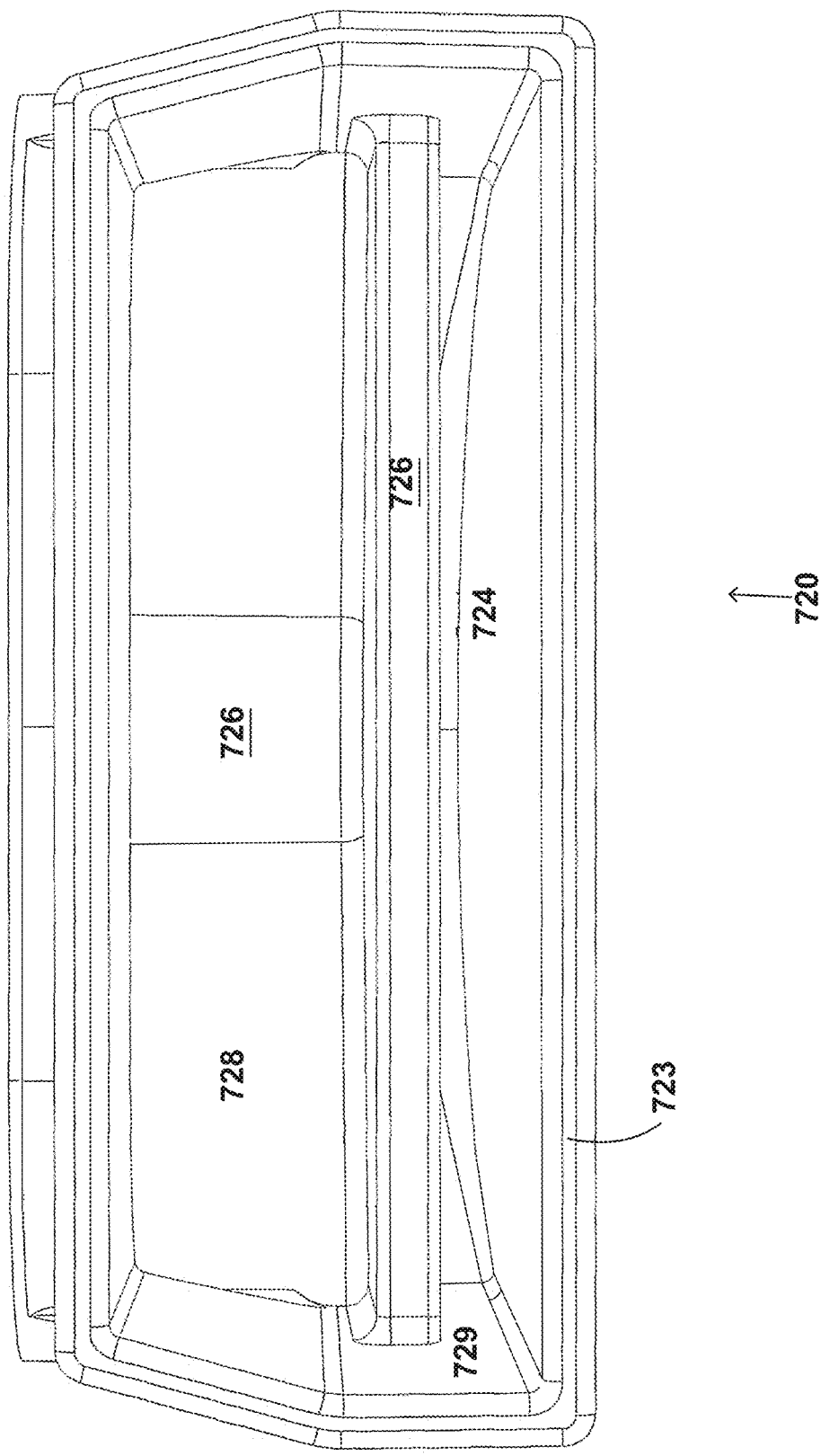
Figure 9E:
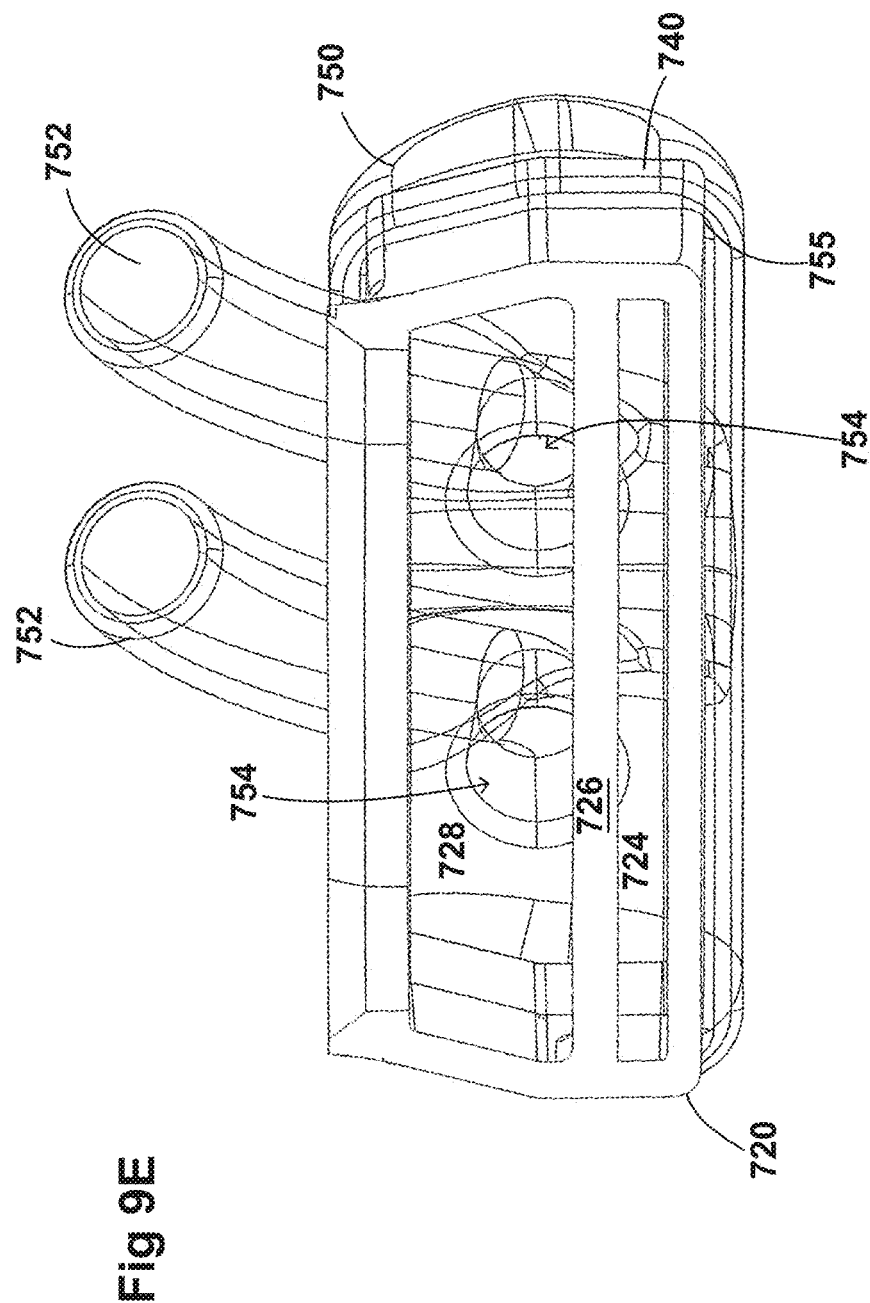

As shown in FIG. 9D, in some embodiments, the cross-section of the housing 720 is asymmetrical. For example, the housing airflow pathway 724 and the housing surfactant lumen 728 can both form a plurality of rectangular profiles. In some embodiments, the housing surfactant lumen 728 can form a rectangular profile that is larger than the housing airflow pathway 724. As illustrated in FIG. 9E, the larger rectangular profile of the housing surfactant lumen 728 can allow for greater delivery of surfactant directly to the nostril lumens 754 of the nasal prongs 752. A plurality of different nasal prong sizes can be interchangeably attached to the housing 720.

FIGS. 10A-10C, 11A-11C, and 12A-12D illustrate housing 820, housing 920, and housing 1020 that are alternative embodiments of the housing 720. Each of the housing 820, housing 920, and housing 1020 resemble the housing 720. Accordingly, the numerals used to identify components of the housing 820, 920, 1020 are incremented by one hundred to identify like features of the housing 720. This number convention generally applies to the remainder of the Figures. Any component disclosed in any embodiment in this specification can be used in other embodiments.

Figure 10C:
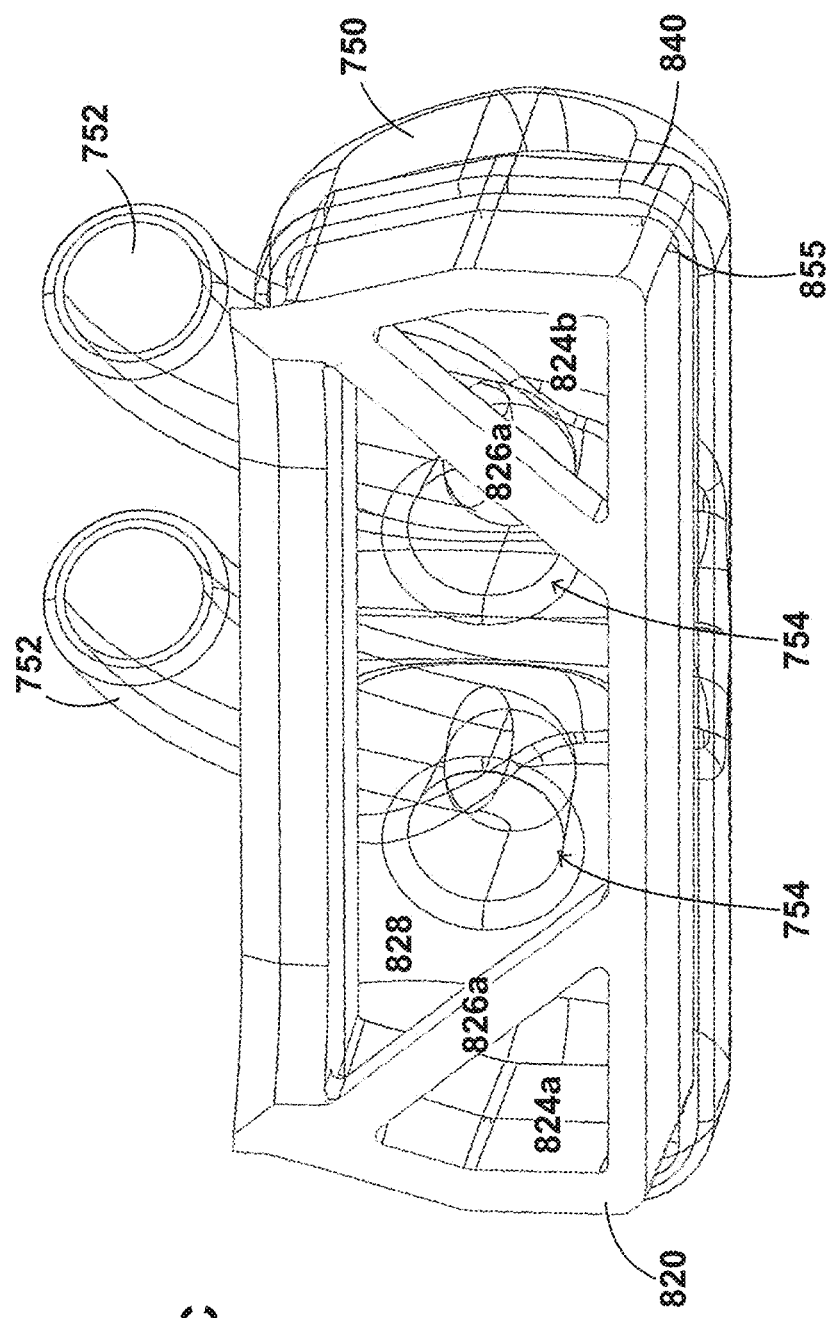

Turning first to the housing 820, FIGS. 10A-10C illustrate an embodiment of the housing 820. In some embodiments, the housing 820 is configured to provide a mixture of airflow from the CPAP and surfactant from the nozzle to the patient. As shown in FIGS. 10A-10C, in some examples, the housing 820 can be divided into a plurality of compartments. As discussed above and in more detail below, the configuration of the housing 820 can provide for improved drug delivery to the patient.

In some examples, the inside of the housing 820 can include a divider 826 that divides the housing 820 to provide a housing airflow entrance 825 with a housing airflow pathway 824 and a housing surfactant entrance 827 with a housing surfactant lumen 828. In some embodiments, the housing airflow entrance 825 is configured to fluidly connect with both the inlet lumen 762 and the outlet lumen 782 of an adaptor (for example the adaptor 700 of FIG. 9A). As discussed with regard to the divider 726 of the housing 720, this can allow inspiratory air from the inlet lumen 762 and expiratory air from the outlet lumen 782 to flow through the housing airflow pathway 824.

Similarly, in some embodiments, the housing surfactant lumen 828 is configured to fluidly connect with the surfactant lumen 712. As discussed above, this can allow surfactant to flow from the surfactant lumen 712 into the housing surfactant lumen 828 without mixing with the inspiratory air from the inlet lumen 762.

FIG. 10B provides a view of the housing 820 from the housing exit 823, wherein the entrance to the housing 820 (the housing airflow entrance 825 and the housing surfactant entrance 827) is oriented upwards. As shown, the divider 826 forms angled portions divider 826a and divider 826b to provide three separate compartments (housing airflow pathway 824 (shown as housing airflow pathway 824a and housing airflow pathway 824b) and housing surfactant lumen 828) for the inspiratory/expiratory airflow and the surfactant flow. As discussed above, the housing 820 near the housing exit 823 includes an undivided portion 829 that allows the inspiratory air from the inlet lumen 762 to mix with the surfactant from the surfactant lumen 712 before being delivered to the patient.

As shown in FIG. 10C, in some embodiments, the cross-section of the housing 820 is asymmetrical. For example, the housing airflow pathway 824 forms a trapezoid from divider 826a and divider 826b. As discussed above, this causes housing surfactant lumen 828 to form housing airflow pathway 824a and housing airflow pathway 824b on either side of the housing airflow pathway 824. As illustrated in FIG. 10C, the centered trapezoidal profile of the housing surfactant lumen 828 can allow for greater delivery of surfactant directly to the nostril lumens 754 of the nasal prongs 752. In some embodiments, airflow from the inlet lumen 762/outlet lumen 782 can pass down the sides of the housing surfactant lumen 828 through housing airflow pathway 824a and housing airflow pathway 824b.

Figure 11B:
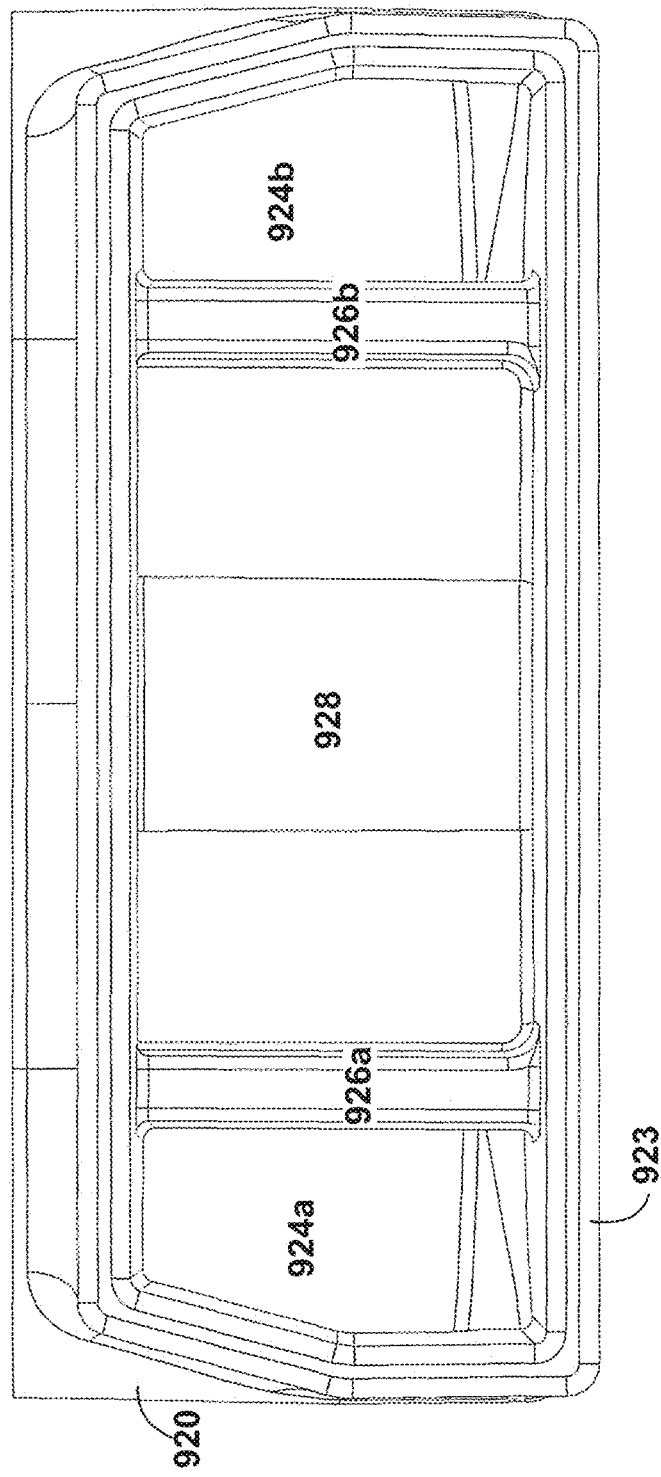
Figure 11C:
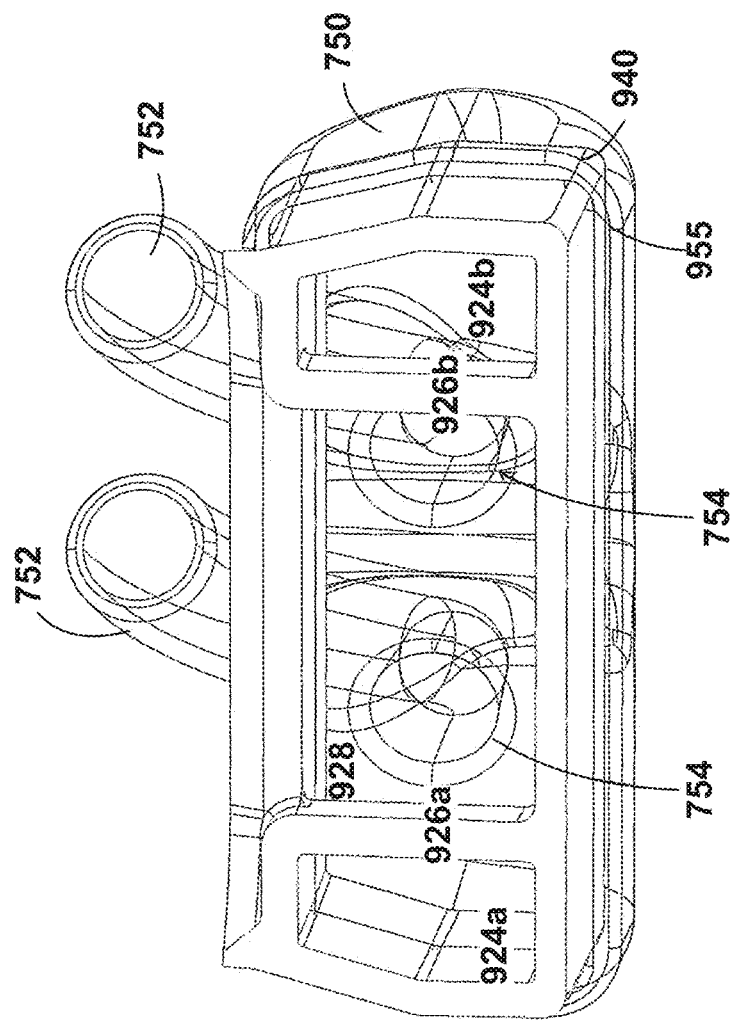

Turning next to the housing 920, FIGS. 11A-11C illustrate an embodiment of the housing 920. In some embodiments, the housing 920 is configured to provide a mixture of airflow from the CPAP and surfactant from the nozzle to the patient. As shown in FIGS. 11A-11C, in some examples, the housing 920 can be divided into a plurality of compartments. As discussed above and in more detail below, the configuration of the housing 920 can provide for improved drug delivery to the patient.

In some examples, the inside of the housing 920 can include a divider 926 that divides the housing 920 to provide a housing airflow entrance 925 with a housing airflow pathway 924 and a housing surfactant entrance 927 with a housing surfactant lumen 928. In some embodiments, the housing airflow entrance 925 is configured to fluidly connect with both the inlet lumen 762 and the outlet lumen 782 of an adaptor (for example the adaptor 700 of FIG. 9A). As discussed with regard to the divider 726 of the housing 720, this can allow inspiratory air from the inlet lumen 762 and outlet lumen 782 to flow through the housing airflow pathway 824.

Similarly, in some embodiments, the housing surfactant lumen 928 is configured to fluidly connect with the surfactant lumen 712. As discussed above, this can allow the surfactant to flow from the surfactant lumen 712 into the housing surfactant lumen 928 without mixing with the inspiratory air from the inlet lumen 762.

FIG. 11B provides a view of the housing 920 from the housing exit 923, wherein the entrance of the housing 920 (the housing airflow entrance 925 and the housing surfactant entrance 927) is oriented upwards. As shown, the divider 926 forms walled divider 926a and divider 926b to provide three separate compartments (housing airflow pathway 924 (shown as housing airflow pathway 924a and housing airflow pathway 924b) and housing surfactant lumen 928) for the inspiratory expiratory airflow and the surfactant flow. As discussed above, the housing 920 near the housing exit 923 includes an undivided portion 929 that allows the inspiratory air from the inlet lumen 762 to mix with the surfactant from the surfactant lumen 712 before being delivered to the patient.

As shown in FIG. 11C, in some embodiments, the cross-section of the housing 920 is asymmetrical. For example, the housing airflow pathway 924 forms a rectangular from the divider 926a and divider 926b. As can be seen in FIG. 11B the divider 926a and 926b are parallel to each other and extend parallel to each other. Each of the dividers 926a and 926b extend vertically from a base of the housing 920. As discussed above, this causes the housing surfactant lumen 928 to form 928a and 928b on either side of the housing airflow pathway 924. As illustrated in FIG. 11C, the rectangular profile of the housing surfactant lumen 928 is centered which can allow for greater delivery of surfactant directly to the nostril lumens 754 of the nasal prongs 752. In some embodiments, airflow from the inlet lumen 762/outlet lumen 782 can pass down the sides of the housing surfactant lumen 928 through housing airflow pathway 924a and housing airflow pathway 924b.

FIGS. 12A-12D illustrates an embodiment of the housing 1020. In some embodiments, as discussed with the other housings above, the housing 1020 is configured to provide a mixture of airflow from the CPAP and surfactant from the nozzle to the patient. As shown in FIGS. 12A-12D, in some examples, the housing 1020 can be divided into a plurality of compartments. As discussed above, and in more detail below, the configuration of the housing 1020 can provide for improved drug delivery to the patient.

In some examples, the housing 1020 can include a divider 1026 that divides the housing 1020 to provide a housing airflow entrance 1025 with a housing airflow pathway 1024 and a housing surfactant entrance 1027 with a housing surfactant lumen 1028. In some embodiments, the housing airflow entrance 1025 is configured to fluidly connect with both the inlet lumen and the outlet lumen from the adaptors (for example inlet lumen 762 and outlet lumen 782). As discussed with regard to the divider 726 of the housing 720, this can allow inspiratory air from the inlet lumen 762 and the expiratory air from the outlet lumen 782 to flow through the housing airflow pathway 1024.

Similarly, in some embodiments, the housing surfactant lumen 1028 is configured to fluidly connect with the surfactant lumen 712. As discussed above, this can allow surfactant to flow from the surfactant lumen 712 into the housing surfactant lumen 1028 without mixing with the inspiratory air from the inlet lumen 762.

FIGS. 12B-12C provide a view of the housing 1020 from the housing exit 1023 wherein the entrance to the housing 1020 (the housing airflow entrance 1025 and the housing surfactant entrance 1027) is oriented upwards. As shown, the divider 1026 forms angled dividers 1026a and 1026b such that the housing airflow pathway 1024 has a curved surface. In some embodiments, this can provide three separate compartments within the housing 1020 (for example, the housing airflow pathway 1024 (shown as housing airflow pathway 1024a and housing airflow pathway 1024b) and housing surfactant lumen 1028) for the inspiratory/expiratory airflow and the surfactant flow. As illustrated in FIG. 12B and discussed above, the housing 1020 near the housing exit 1023 can include an undivided portion 1029 that allows the inspiratory airflow from the inlet lumen 762 to mix with the surfactant from the surfactant lumen 712 before being delivered to the patient.

Figure 12A:
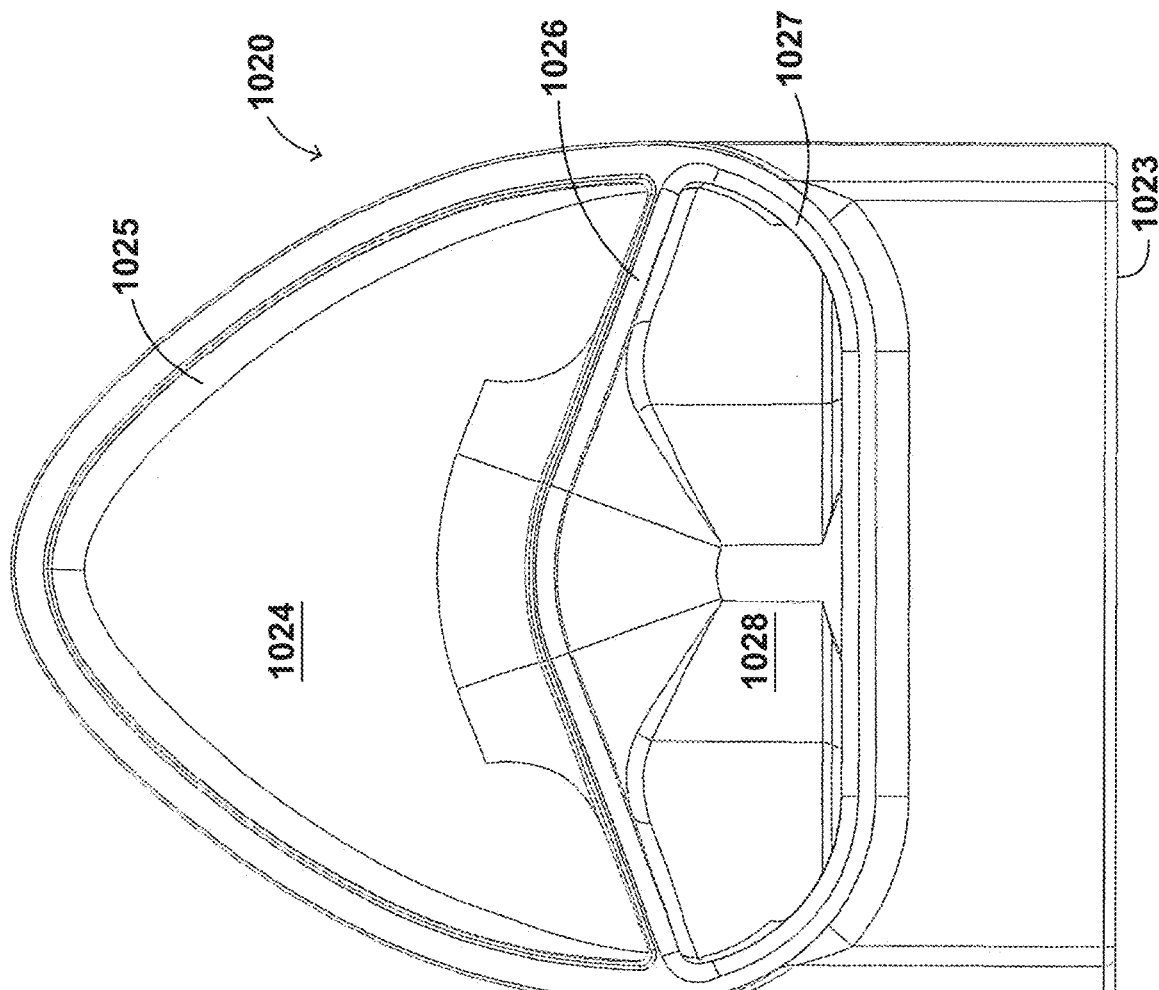
Figure 12D:
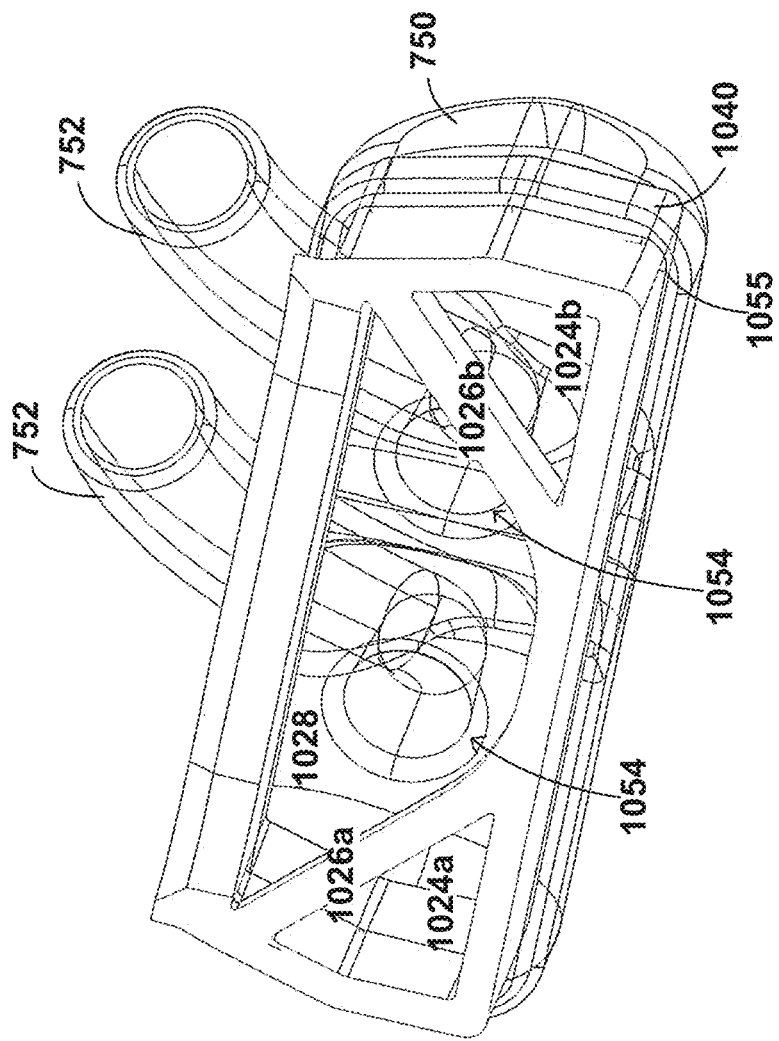

As shown in FIG. 12D, in some embodiments, the cross-section of the housing 1020 is asymmetrical. For example, the housing surfactant lumen 1028 forms a rounded triangle from the dividers 1026a and 1026b. As discussed above, this causes housing airflow pathway 1024 to form a first housing airflow pathway 1024a and a second housing airflow pathway 1024b on either side of the housing surfactant lumen 1028. As illustrated in FIG. 10D, the centered triangular profile of the housing surfactant lumen 1028 can allow for greater delivery of surfactant directly to the nostril lumens 754 of the nasal prongs 752. As can be seen in FIG. 10D, the housing surfactant lumen 1028 is also better aligned with the prongs to provide a more direct flow path for the surfactant and air mixture to the prongs 752. In some embodiments, the rounded cross-section of the housing surfactant lumen 1028 can reduce the amount of surfactant deposited within the housing surfactant lumen 1028. In some examples, airflow from the inlet lumen 762/outlet lumen 782 can pass down the sides of the housing surfactant lumen 1028 through housing airflow pathway 1024a and housing airflow pathway 1024b. The aerosolized surfactant can be received at the surfactant port 710 and be received by the surfactant lumen 1028. The aerosolized surfactant can mix with the incoming gases flow from the housing airflow pathway and then be delivered to a patient via the nostrils. The housing surfactant lumen 1028 is larger in cross sectional area than each of the housing air flow lumens 1024a, 1024b. This helps for an adequate amount of aerosolized surfactant to be received within the undivided section of the housing 1023 to allow adequate mixing and delivery of aerosolized surfactant or other medicaments to the nostrils of the patient via the prongs 752. The cross sectional area of the housing surfactant lumen 1028 being greater than the cross sectional area of the housing air flow lumens 1024a, 1024b also helps to reduce deposition of aerosolized surfactant within the surfactant lumen. The shape of the housing surfactant lumen 1028 may be a diffuser or act as a diffuser as surfactant moves from the surfactant tube 714 and into the housing surfactant lumen. The housing surfactant lumen may flare outwardly as it extends toward the prongs and the undivided portion thereby reducing the velocity of delivered surfactant. This reduced velocity may encourage improved mixing with the airflow and thereby reducing the amount of surfactant deposition.

In some embodiments, the adaptor can include pressure and surfactant lumens that are nested together on the side of the adaptor away from the patient. In some embodiments, the surfactant port or the nozzle in the adaptor can be bifurcated and may optionally include a pressure sensing nozzle that faces the patient. In some examples, the pressure sensing nozzle can provide more accurate pressure sensing. In some embodiments the adaptor any suitable patient interface can be used interchangeably with the adaptor, and in particular with the housing of the adaptor. The various adaptors described herein are described as being suitable for delivering aerosolized surfactant to a patient. The adaptors and patient interfaces described herein can also be used to deliver other aerosolized products such as asthma drugs, or other respiratory treatment medicines or drugs. The adaptors as described herein may also be used to deliver nebulized drugs or medicaments for the treatment of respiratory illness such as for example, COPD (Chronic obstructive pulmonary disease), asthma, cystic fibrosis or other respiratory diseases or illnesses. The adaptor may also be configured to deliver aerosolized water to provide additional humidity therapy.

In some embodiments, the aforementioned disclosed adaptors can include a securement system for retaining, holding, or securing pressure and/or surfactant lumens in position on a patient's face. In some embodiments, the pressure lumen is configured to be fluidly connected to the pressure tube and the surfactant lumen is configured to be fluidly connected to the surfactant tube described herein. In some embodiments, the securement system comprises a two-part releasable attachment or connection arrangement. The releasable connection arrangement acts between a pair of components that are affixed to the patient and the pressure and/or surfactant tube respectively. Several such securement systems are described in Applicant's U.S. application Ser. No. 14/395,047, filed on Apr. 17, 2013.

An example of the attachment mechanism of Applicant's U.S. application Ser. No. 14/395,047 is hereby reproduced as FIGS. 18-20.

Figure 18:
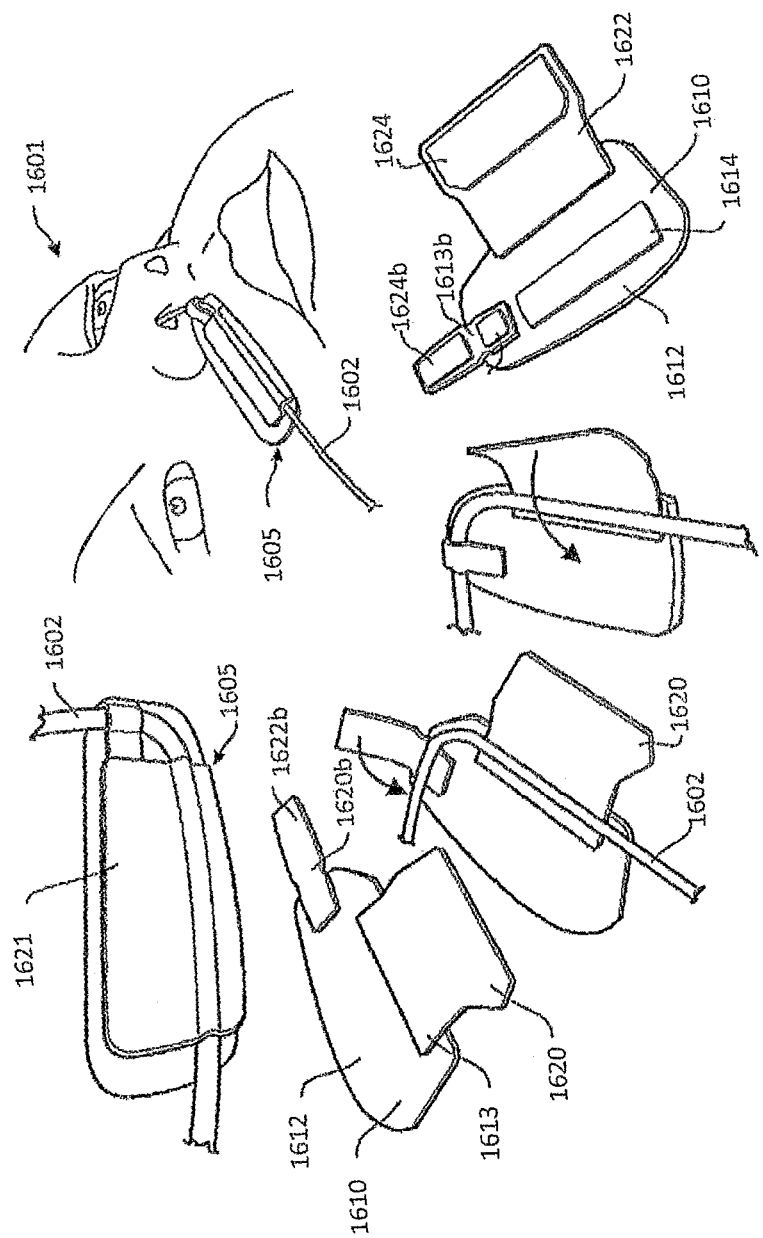
Figure 19:
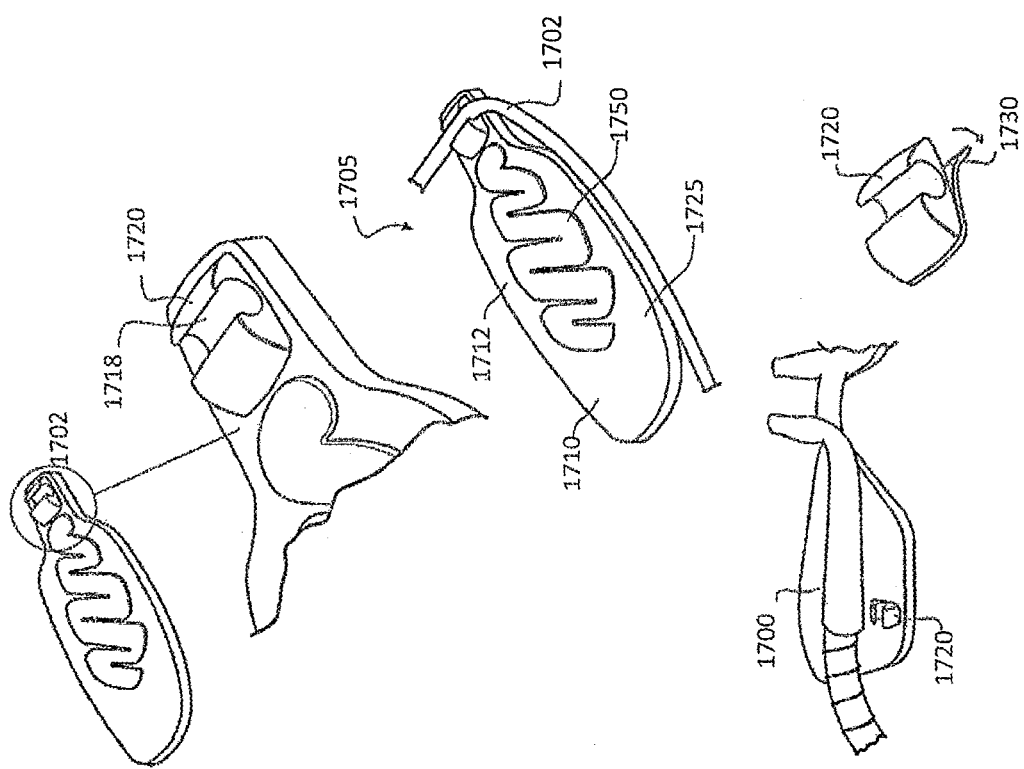
Figure 20:
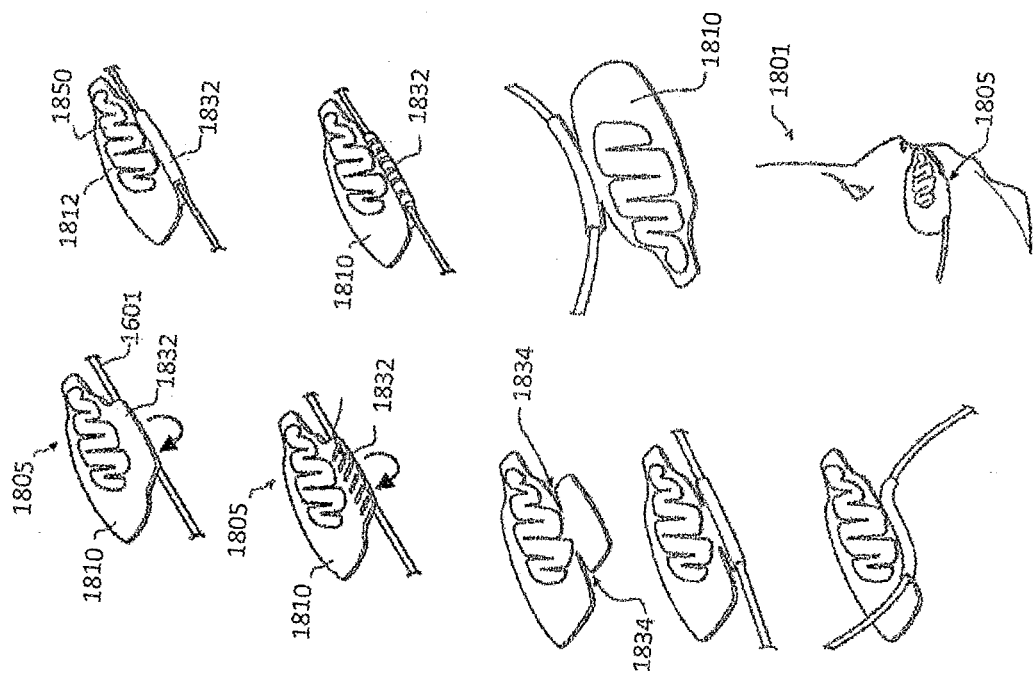

In reproduced FIGS. 18-20, the two-part releasable attachment mechanism can further include structures to retain the pressure and/or surfactant tube. In some embodiments, these structures can be holder, clips, flaps, etc.

For example, as illustrated in FIG. 18, the two-part releasable attachment mechanism can include a panel that is configured to be folded onto the dermal patch so as to retain the tube. The dermal patch 1610 and the panel 1620 are coupled together at an edge region 1613. To couple the first and second parts of the two-part releasable attachment system together, the panel is folded onto the dermal patch to bring the patient side 1622 of the panel adjacent to the interface side 1612 of the dermal patch to couple the first and second parts 1614, 1624 of the two-part connection system together to capture or sandwich the tube 1602 there between.

As another example, FIG. 19 illustrates the two-part releasable attachment mechanism further including a clip for securing a pressure and/or surfactant tube. The dermal patch 1710 for adhering to the skin of the patient can include a securement clip 1720 that is attached to or integrally formed with the dermal patch. The securement clip includes a recess or cavity or channel for receiving the tube 1702. The recess is open so that a section of the tube may be pushed in a lateral direction with respect to a longitudinal axis of the tube into the clip. An end of the tube need not be pushed through the clip for securement. The recess can have a lateral dimension similar to or slightly smaller than a diameter of the tube so that the tube is gripped firmly by the clip. In one embodiment, the clip is releasable from the dermal patch. For example, a two-part connection system as described previously may be applied between the clip and the dermal patch. Alternatively, the clip may be releasably attached to a patient interface 1700.

FIG. 20 illustrates the two-part releasable attachment mechanism having a wing portion that is configured to wrap about and secure the pressure and/or surfactant tube. The securement system 1805 can include a dermal patch 910 for attaching to the face of a patient. The dermal patch comprises a wing portion 932 for wrapping about the tube 2 once the tube has been correctly positioned in the patient's nostril.

The adaptors disclosed herein can also be used with the fixation structures disclosed in Applicant's PCT App. No. PCT/NZ2016/050050, filed on Mar. 30, 2016 which is hereby incorporated by reference. An example of the fixation structures of Applicant's PCT App. No. PCT/NZ2016/050050 is hereby reproduced as FIGS. 21A-21B.

Figure 21A:
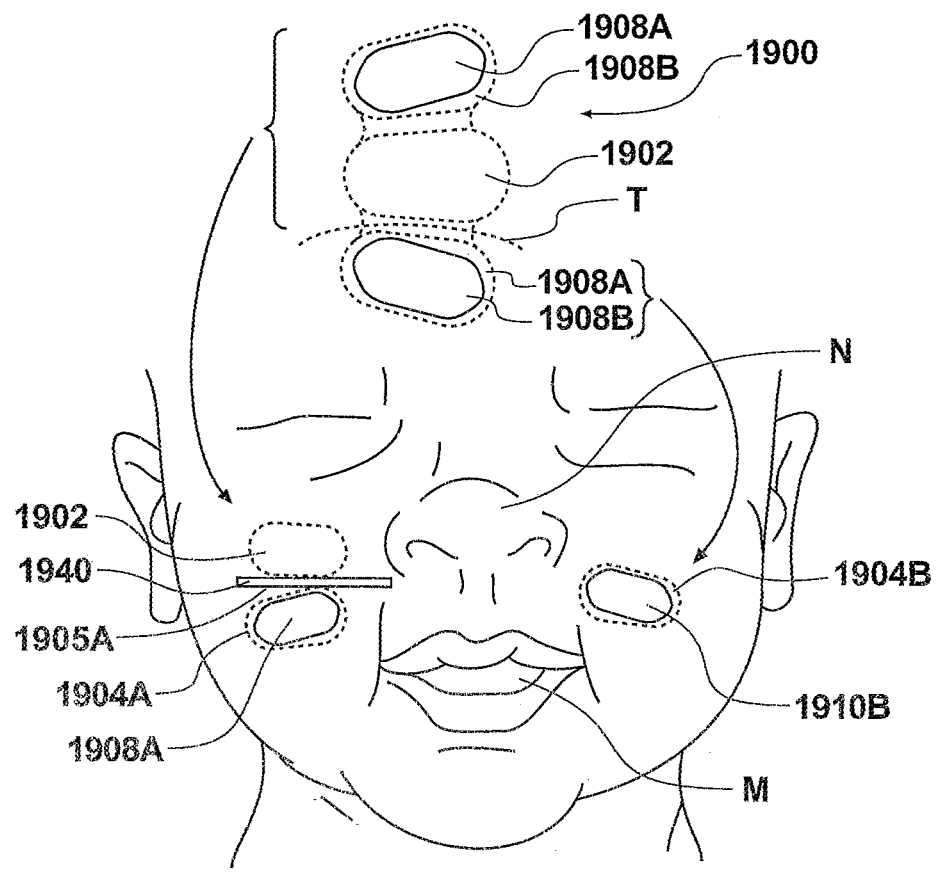
Figure 21B:
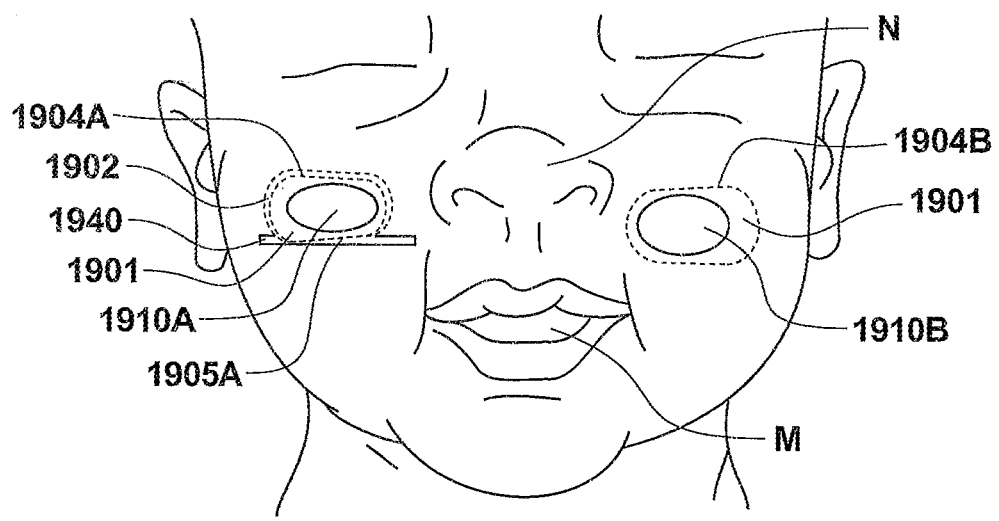

FIGS. 21A-21B illustrates an embodiment of a fixation structure that can be configured to secure the pressure and/or surfactant tube. FIGS. 21A and 21B illustrate the fixation structure assembly having perforated sections that allow for the removal of the fixation structure from the tube to be secure.

A close-up of a face of a patient is shown, with a nose N and mouth M. The fixation structure assembly 1900 may be torn along tear line T, detaching one of the separable extensions 1904B. In the illustrated embodiment, a pair of perforated sections links the body 1902 with one of the separable extensions 1904A, 1904B. The body 1902 and the separable extension 1904A still attached to the body 1902 may be placed on one side of the face, and the detached separable extension 1904B may be adhered to the other side of the face via use of the adhesive portion 1908B, thus exposing the fixation element 1910B of the detached separable extension 604B. The tube 1940 can be placed over the body 1902, and the separable extension 1904A attached to the body 1902 can be folded to cover the tube 1940.

As shown in FIGS. 21A-21B, the tube 1940 can be positioned in the perforated area (for example, the first intermediate region 1905 A) or adjacent the perforated area. This can facilitate quick and simple removal of the fixation structure assembly 1900 from the tube 1940. As a result, the tube 1940 does not necessarily have to be removed as the fixation structure is removed, and a healthcare provider is then not required to reinsert the tube 1940 following removal of the fixation structure assembly 1900, reducing the number of steps required. Positioning the tube 1940 in or near the perforated area can aid in enabling the fixation structure assembly 1900 to be folded and/or to stick to itself. For example, this can aid in the separable extension 1904A being folded over the body 1902.

In some examples, the moulding part-line could also be down the central plane of symmetry of the adaptor (instead of splitting along the threaded connectors). In some examples, the threaded connectors can also be arranged with their axes parallel to the plane of symmetry but offset from the center so as to create space between them. In some examples, this can allow for a more compact arrangement and simpler tooling, with less complex movements. This can also possibly include the pressure port facing longitudinally between them.

It should be noted that various changes and modifications to the presently preferred embodiments described herein will be apparent to those skilled in the art. Such changes and modifications may be made without departing from the spirit and scope of the apparatus and systems of the disclosure and without diminishing its attendant advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

Reference to any prior art in this specification is not, and should not be taken as, an acknowledgement or any form of suggestion that that prior art forms part of the common general knowledge in the field of endeavour in any country in the world.

Wherein the foregoing description reference has been made to integers or components having known equivalents thereof, those integers are herein incorporated as if individually set forth.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The apparatus and system of the disclosure may also be said broadly to consist in the parts, elements and features referred to or indicated in the specification of the application, individually or collectively, in any or all combinations of two or more of said parts, elements or features.

What is claimed is:

1. An adaptor for medicament delivery comprising:
    a tubular body having a first end and a second end, wherein the tubular body comprises:
        an inlet tube having an inlet port at the first end and an outlet at the second end, wherein the inlet port is configured to be connected to an inspiratory conduit for receiving a flow of gases, an outlet tube adjacent to the inlet tube having an outlet port at the first end and an inlet at the second end, wherein the outlet port is configured to be connected to an expiratory conduit for dispensing the flow of gases, and a surfactant delivery tube adjacent to a portion of at least one of the inlet tube and the outlet tube, wherein the surfactant delivery tube comprises an inlet port at the first end and an outlet at the second end, wherein the inlet port of the surfactant delivery tube is configured to connect to a source of medicament;

a housing having a first end and a second end, wherein the first end of the housing is attached to the second end of the tubular body;

a patient interface configured to be connected to the second end of the housing, wherein the patient interface is configured to be in fluid communication with an airway of a patient; and wherein the housing comprises a divider to separate the flow of gases from a flow of medicament, the divider configured to provide a plurality of fluid entryways into an interior of an undivided portion of the housing.

2. The adaptor of claim 1, wherein the housing is permanently attached to the tubular body.

3. The adaptor of claim 1, wherein the tubular body and the housing comprise a plastic.

4. The adaptor of claim 1, wherein at least a portion of the housing is configured to allow the flow of gases to mix with the flow of medicament.

5. The adaptor of claim 1, wherein the flow of medicament comprises an aerosolized surfactant.

6. The adaptor of claim 1, wherein the divider comprises angled sidewalls.

7. The adaptor of claim 6, wherein the divider further comprises a rounded portion connecting the angled sidewalls to improve fluid flow around corners.

8. The adaptor of claim 1, wherein the divider comprises straight walls to form rectangular fluid entryways to the interior of the undivided portion of the housing.

9. The adaptor of claim 1, wherein a cross-section of a portion of the housing in fluid communication with the surfactant delivery tube is greater than a cross-section of a portion of the housing in fluid communication with the inlet tube and the outlet tube, and wherein the greater cross-section of the portion of the housing in fluid communication with the surfactant delivery tube is configured to reduce deposition of medicament within the surfactant delivery tube.

10. The adaptor of claim 1, wherein the patient interface comprises a pair of nasal prongs.

11. The adaptor of claim 10, wherein the pair of nasal prongs are sized to fit the nares of the patient.

12. The adaptor of claim 10, wherein the patient interface is configured to interchangeably attach to a plurality of different nasal prong sizes.

13. The adaptor of claim 1, wherein the patient interface is press-fit onto the second end of the housing.

14. The adaptor of claim 1, wherein the patient interface is removably connected to the second end of the housing.

15. The adaptor of claim 1, wherein the tubular body further comprises a pressure port connected to a pressure sensor, wherein the pressure sensor is configured to measure air pressure flowing through the pressure port.

16. The adaptor of claim 15, wherein the tubular body further comprises a pressure tube connected to the housing.

17. The adaptor of claim 15, wherein the pressure port and the inlet port of the surfactant delivery tube are on opposing sides of the adaptor.

18. The adaptor of claim 1 wherein the tubular body comprises an elongated oval cross-section.

* * * * *